(12) United States Patent
Baranowska-Kortylewicz et al.

(10) Patent No.: US 10,874,752 B2
(45) Date of Patent: Dec. 29, 2020

(54) MIBG ANALOGS AND USES THEREOF

(71) Applicant: Board of Regents of The University of Nebraska, Lincoln, NE (US)

(72) Inventors: Janina Baranowska-Kortylewicz, Omaha, NE (US); Zbigniew P. Kortylewicz, Omaha, NE (US)

(73) Assignee: Board of Regents of The University of Nebraska, Lincoln, NE (US)

( * ) Notice: Subject to any disclaimer, the term of this patent is extended or adjusted under 35 U.S.C. 154(b) by 81 days.

(21) Appl. No.: 15/762,406

(22) PCT Filed: Sep. 23, 2016

(86) PCT No.: PCT/US2016/053497
§ 371 (c)(1),
(2) Date: Mar. 22, 2018

(87) PCT Pub. No.: WO2017/053834
PCT Pub. Date: Mar. 30, 2017

(65) Prior Publication Data
US 2018/0256761 A1      Sep. 13, 2018

Related U.S. Application Data

(63) Continuation of application No. 62/232,491, filed on Sep. 25, 2015.

(51) Int. Cl.
*A61K 51/00* (2006.01)
*A61M 36/14* (2006.01)
*A61K 51/04* (2006.01)
*C12Q 1/68* (2018.01)
*A61K 31/7072* (2006.01)
*C12Q 1/6886* (2018.01)
*C07B 59/00* (2006.01)
*C07D 405/04* (2006.01)
*C07F 9/6571* (2006.01)
*A61P 35/00* (2006.01)
*A61K 9/00* (2006.01)
*A61B 5/055* (2006.01)
*A61B 6/03* (2006.01)

(52) U.S. Cl.
CPC ........ *A61K 51/0491* (2013.01); *A61K 9/0019* (2013.01); *A61K 31/7072* (2013.01); *A61K 51/0459* (2013.01); *A61K 51/0497* (2013.01); *A61P 35/00* (2018.01); *C07B 59/002* (2013.01); *C07B 59/004* (2013.01); *C07D 405/04* (2013.01); *C07F 9/657127* (2013.01); *C12Q 1/68* (2013.01); *C12Q 1/6886* (2013.01); *A61B 5/055* (2013.01); *A61B 6/037* (2013.01)

(58) Field of Classification Search
None
See application file for complete search history.

(56) References Cited

U.S. PATENT DOCUMENTS

2010/0104628 A1   4/2010   Ludeman et al.
2013/0149244 A1   6/2013   Purohit et al.

FOREIGN PATENT DOCUMENTS

WO   2009018088   2/2009
WO   2016078582   5/2016

OTHER PUBLICATIONS

Neumaier et al. Regional workshop on F-18 radiopharmaceuticals, Smolenice, Slovakia, Nov. 25-27, 2001 p. 1-7.*
Fidler et al. (J. Nat. Cancer Inst. 1970, 45, 773-782).*
Macapinlac et al. (J. Nucl. Med. 1996, 37(4 Suppl), 25S-29S).*
Kassis et al. (J. Nucl. Med. 1998, 39, 1148-1154).*
International Search Report and Written Opinion in corresponding PCT Application Serial No. PCT/US2016/053497, dated Feb. 17, 2017.
Extended Search Report in corresponding European Patent Application No. 16849777.4, dated May 7, 2019.
Faraj, et al., "Synthesis and evaluation of new 2',3'-dideoxynucleoside analogs as potential anti-AIDS and anti-herpes drugs", Eur J Med Chem, 1992, vol. 27, 141-148.
Vanheusden, et al., "Thymidine and thymidine-5'-O-monophosphate analogues as inhibitors of *Mycobacterium tuberculosis* thymidylate kinase", Bioorg Med Chem Lett, Sep. 15, 2003, vol. 13, issue 18, 3045-3048.
Zhang, et al., "A new class of 5-fluoro-2'-deoxyuridine prodrugs conjugated with a tumor-homing cyclic peptide CNGRC by ester linkers: synthesis, reactivity, and tumor-cell-selective cytotoxicity", Pharm Res, Mar. 2005, vol. 3, 381-389.

* cited by examiner

*Primary Examiner* — Michael G. Hartley
*Assistant Examiner* — Melissa J Perreira
(74) *Attorney, Agent, or Firm* — Hovey Williams LLP

(57) ABSTRACT

Compounds and compositions for targeting cells expressing norepinephrine transporter, and methods of making and using the same. The compounds comprise MIBG analogs conjugated to active agents for treatment and/or diagnosis of various conditions, including neuroblastoma.

21 Claims, 41 Drawing Sheets

Scheme 2

27: R = I
28: R = Sn(Me)₃
29: R = ¹²⁵I (from 29)

26

30

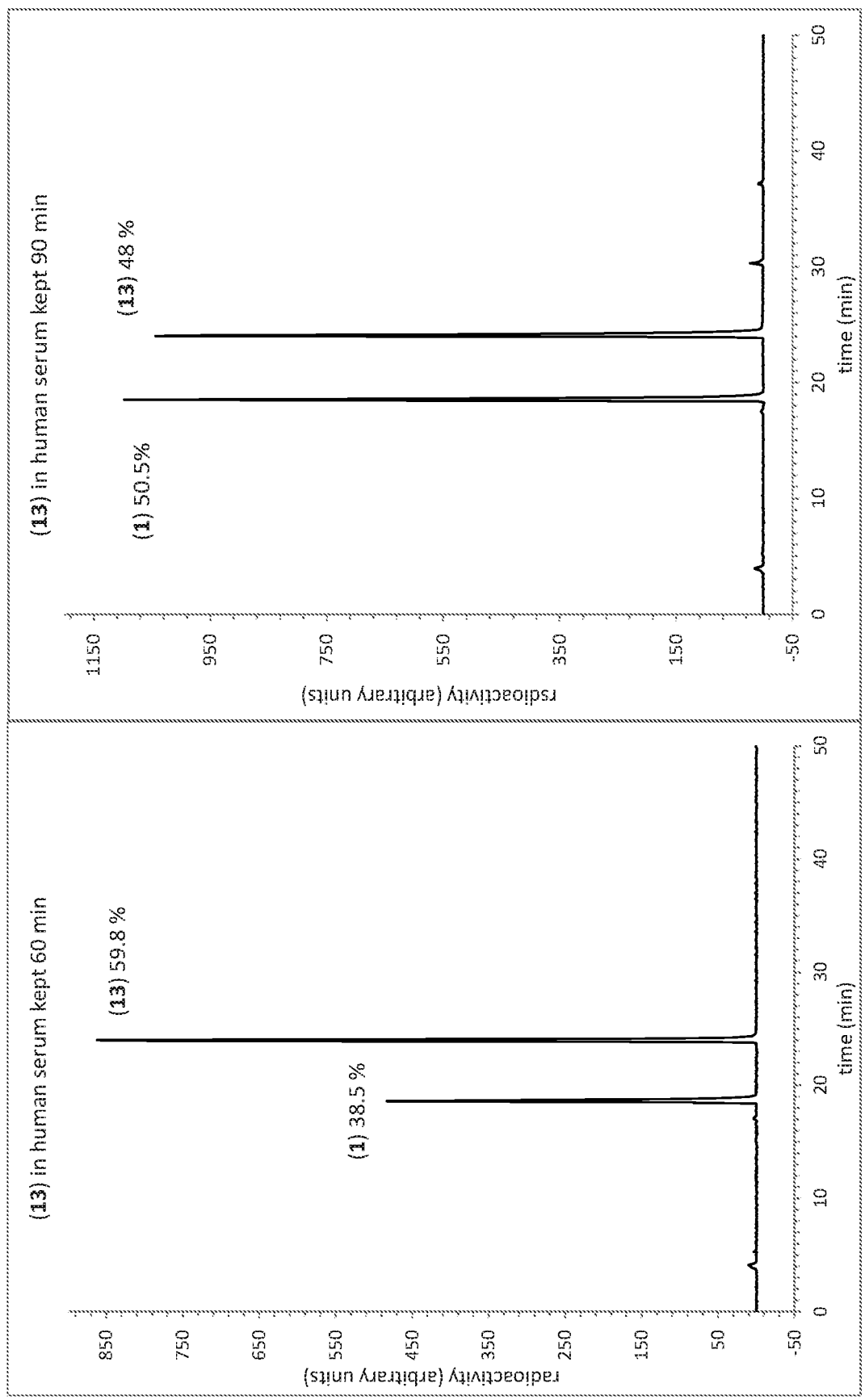

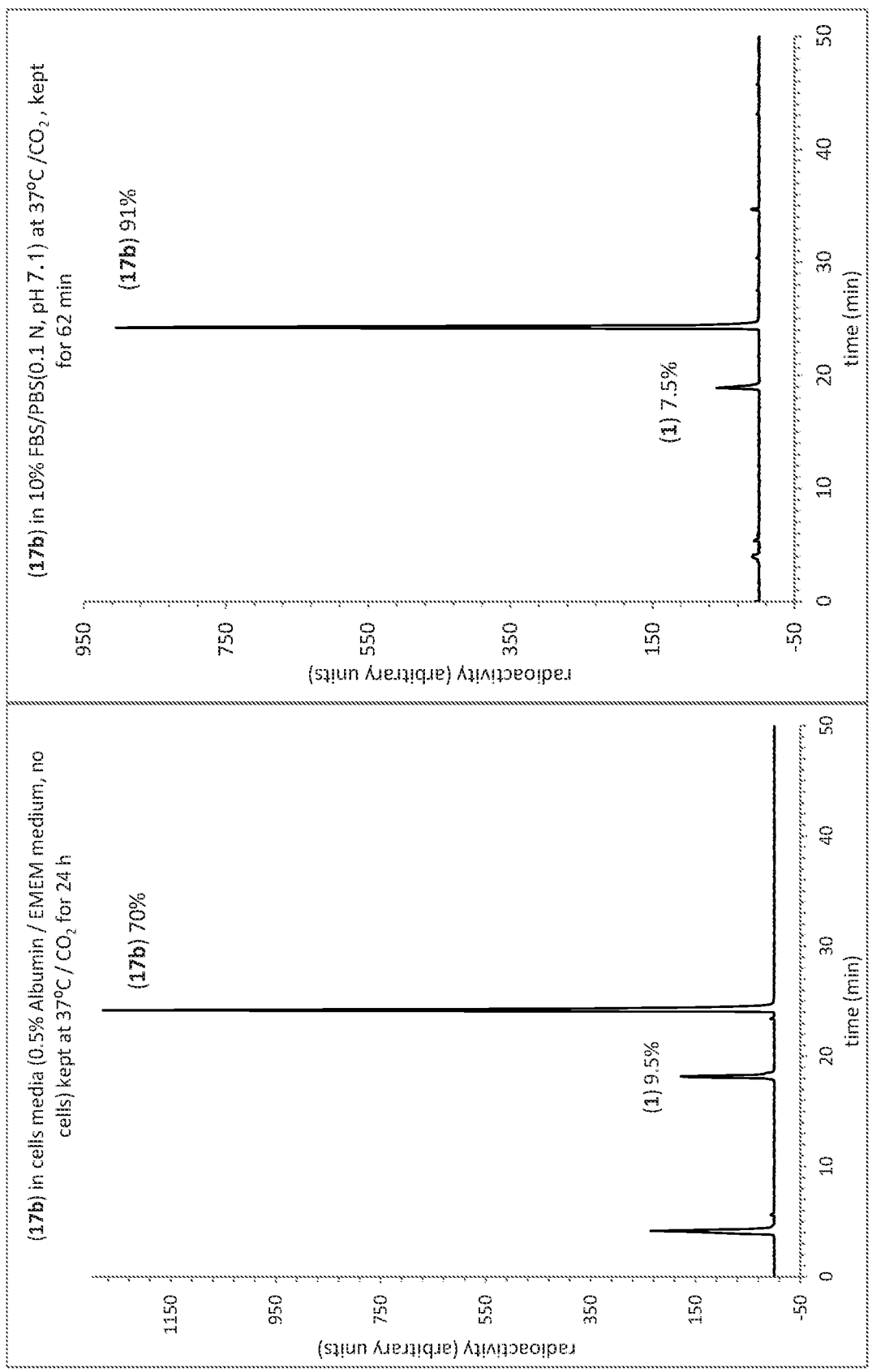

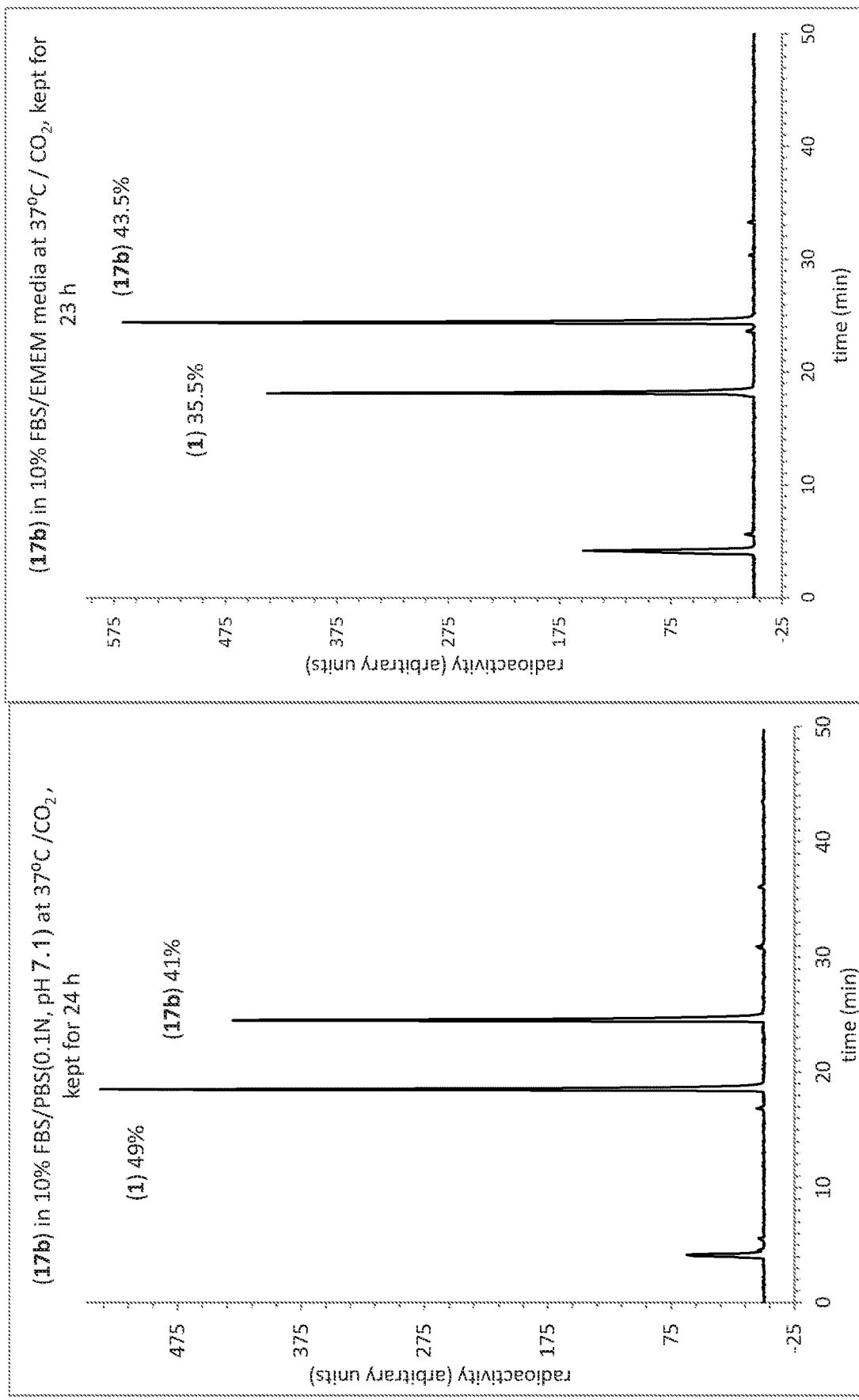

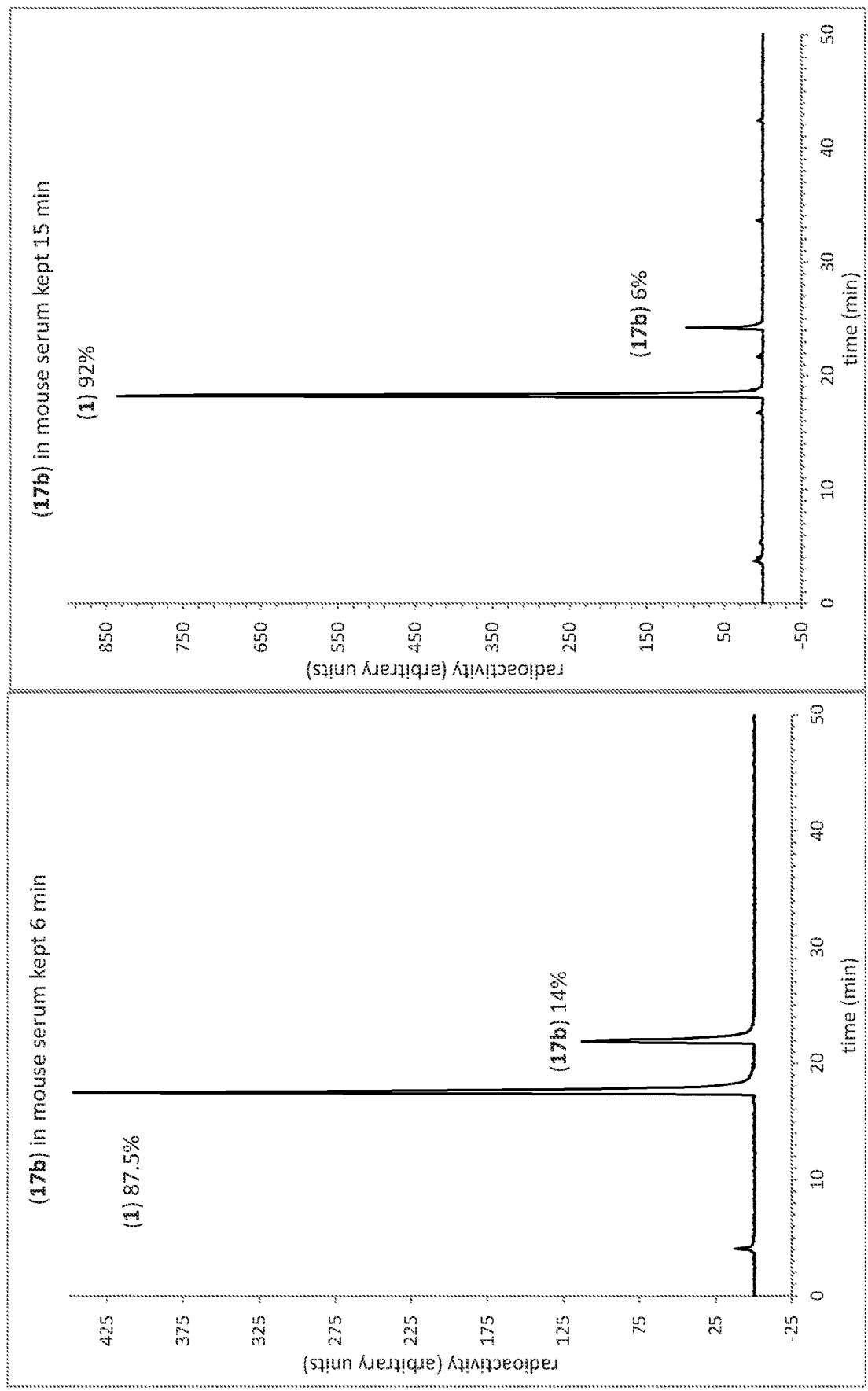

MIBG ANALOGS AND USES THEREOF

CROSS-REFERENCE TO RELATED APPLICATIONS

The present application is the U.S. National Stage of International Patent Application No. PCT/US2016/053497, filed Sep. 23, 2016, which claims the priority benefit of U.S. Provisional Patent Application Ser. No. 62/232,491, filed Sep. 25, 2015, entitled MIBG Analogs and Uses Thereof, each of which is incorporated by reference in its entirety herein.

BACKGROUND OF THE INVENTION

Field of the Invention

The present invention relates to diagnostic and therapeutic compounds for specifically targeting neuroblastoma cancer cells and other cancerous or non-cancerous conditions in which norepinephrine transporter is expressed.

Description of Related Art

Neuroblastoma is the most common extracranial solid tumor in children. It is a disease with pronounced clinical and biological heterogeneity, and notoriously unpredictable clinical outcomes. The 5-year survival rate in these patients is only around 30%. Neuroblastoma is highly radiosensitive. However initial treatment using beta emitters, such as iodine-131, yttrium-90 and lutetium-177 have had minimal success. Many patients diagnosed with neuroblastoma have metastatic disease, refractory disease, or relapse after the initial treatment. Another established treatment involves metaiodobenzylguanidine (MIBG), a structural analog of norepinephrine that is taken up selectively by neuroblastoma cells.

Radiotherapy with $^{131}$I-metaiodobenzylguanidine ($^{131}$IMIBG) is a treatment option for patients with relapsed or refractory neuroblastoma. In the 30 years since its introduction, many clinical studies of $^{131}$IMIBG have been conducted. Published reports indicate that this treatment is relatively safe. However, tumor responses are frequently transient. Even at the maximum tolerated dose of >600 MBq/kg, remissions are of short duration. Hematologic toxicities are the main side effect, although some patients also develop secondary malignancies. $^{131}$IMIBG also appears to damage ovaries, and over 80% of long-term survivors treated with $^{131}$IMIBG develop thyroid disorders.

Some of the reasons for the failure of current radiotherapy are side effects related to the currently-used isotopes and the relatively poor retention of the drug in neuroblastoma cells. For example, the washout of $^{131}$IMIBG from neuroblastoma cells is rapid with the half-life $t_{1/2}$<60 min. In addition, the mean range of $^{131}$I β-particles is ~800 μm. This means that small tumors, <1 mm in diameter, are under-dosed while the decay energy is deposited in the adjacent normal tissues. Based on the current radiotherapies it is evident that these treatments need to be optimized to enhance efficacy of this approach.

There is a significant need for new theranostics for high-risk neuroblastoma that are more effective and less toxic than $^{131}$IMIBG. There is also a need for new treatment and imaging options for other cancers and disease involving the norepinephrine transporter such as neuroendocrine tumors.

SUMMARY OF THE INVENTION

The present invention is broadly concerned with structural analogs of MIBG. As used herein, the terms "MIBG analog" or "analogs of MIBG" refer to second generation MIBG analogs containing norepinephrine transporter-targeted guanidine moieties (derived from MIBG). These moieties can be attached to an active agent to create therapeutic and/or diagnostic conjugates. These conjugates are capable of binding to and being selectively taken up and degraded by cancer cells and other cells having certain markers, and thereby delivering to the cell the active agent. In one aspect, the conjugates can be used to deliver to the cell nucleus a radioisotope capable of being incorporated into the nuclear material, so as to produce a cytotoxic effect and/or to render the cancer cell detectable by nuclear medicine imaging. The compounds of the invention can be safely administered in long-term cancer treatments, without producing significant adverse health effects.

The present invention also relates generally to methods for targeted therapy and medical imaging as applied to cancer treatment and diagnosis, and in particular to conjugates composed of a radiolabeled, cell cycle-dependent active agent chemically coupled to a ligand that targets norepinephrine transporter. The conjugates of the invention are taken up selectively by cancer cells that have norepinephrine transporter and are incorporated into the nucleus of such cells, where they produce a cytotoxic effect and/or are detectable via imaging techniques.

More particularly, in one aspect, therapeutic and/or diagnostic compound are described herein. These compounds are useful for selective targeting of norepinephrine transporter in a cell. The compounds comprising an MIBG analog conjugated to an active agent. The MIBG analog is selected from the group consisting of:

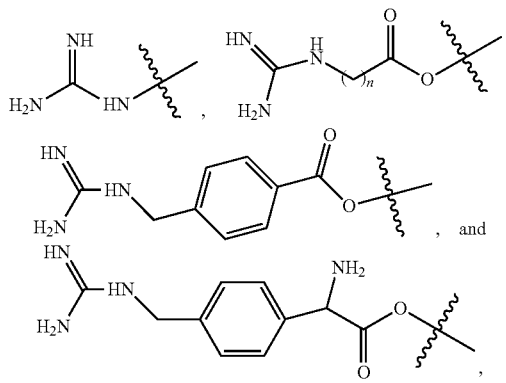

where n is 1-5, and the wavy line indicates the point of attachment to the active agent (e.g., a radiolabeled thymidine analog).

Also described herein are therapeutic and/or diagnostic compositions comprising at least one MIBG analog-active agent conjugate according to the various embodiments described herein. The compositions generally comprise a therapeutically- or diagnostically-effective amount of the conjugate compound, dispersed in a pharmaceutically-acceptable vehicle.

Methods of treating neuroblastoma in a patient in need of such treatment are also described herein, where the neuroblastoma comprises cancer cells characterized by norepinephrine transporter expression. The method comprises administering to the patient a therapeutically effective amount of at least one therapeutic compound comprising an MIBG analog conjugated to an active agent according to the various embodiments described herein.

Also described herein are methods of detecting cells expressing norepinephrine transporter in a subject. The methods generally comprise administering to the patient an effective amount for imaging of at least one diagnostic compound comprising an MIBG analog conjugated to an active agent according to the various embodiments described herein, wherein the active agent comprises a detectable label that generates a detectable signal. Binding between the compound and the norepinephrine transporter expressed by the cells is then detected using a suitable imaging technique to thereby indicate a location of the cells in said subject.

Kits for treating or detecting cells expressing norepinephrine transporter in a subject are also described herein. The kits generally comprise a vessel containing a compound comprising an MIBG analog conjugated to an active agent to the various embodiments described herein; a pharmaceutically acceptable carrier medium; and instructions for use thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8A-FIG. 8M are a set of graphs showing HPLC analysis demonstrating the stability of 5-[$^{125}$I]-Iodo-5'-O-hexanoylguanidino-2'-deoxyuridine (17b);

DETAILED DESCRIPTION

Figure 1A:
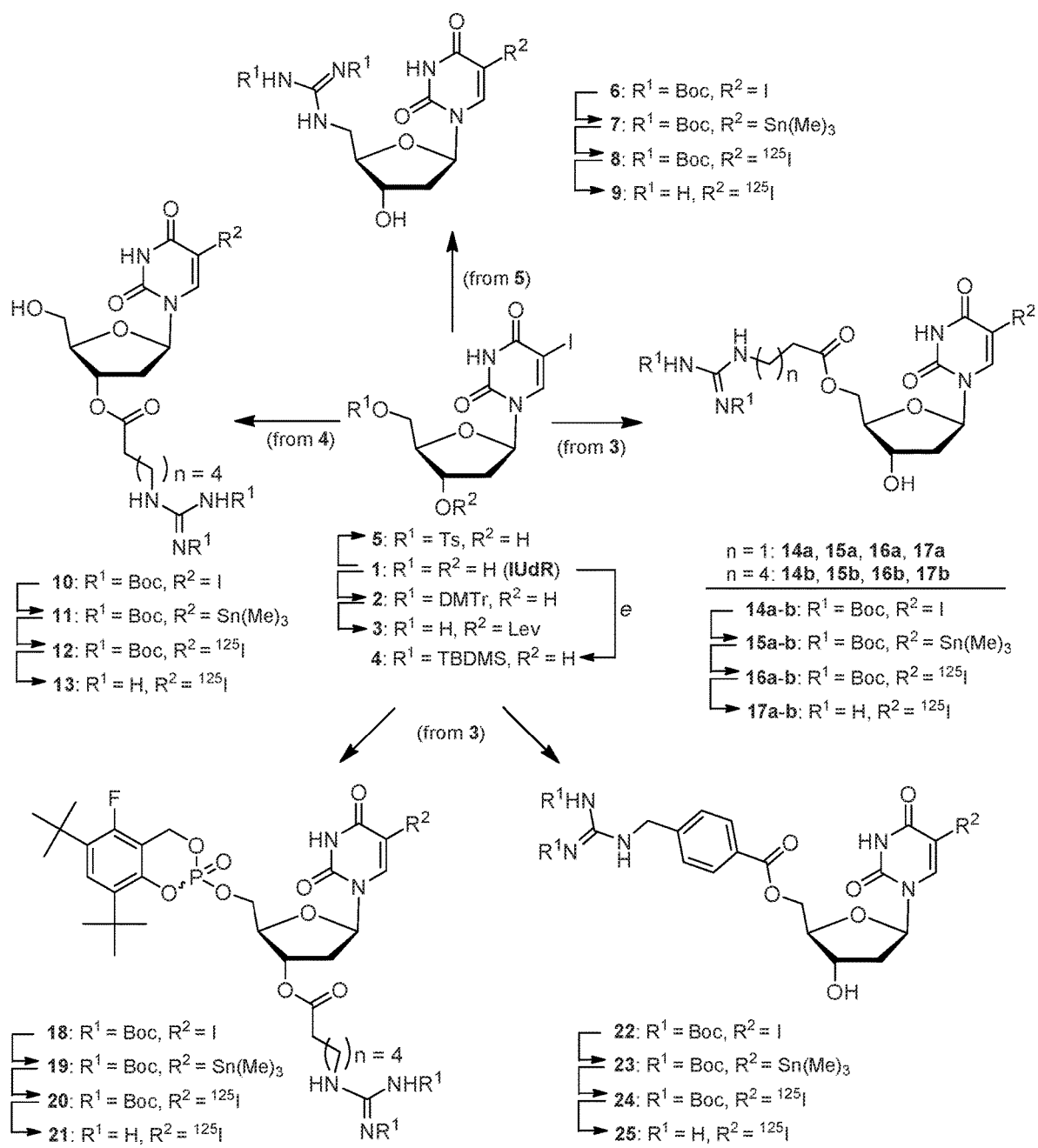
FIG. 1A shows the reaction scheme used to prepare the guanidinoalkyl esters of 5-[$^{125}$I]-iodo-2'-deoxyuridine.

The present invention is concerned with analogs of MIBG, theranostic compound conjugates comprising the MIBG analogs conjugated to an active agent, and methods of making and using the same for targeted treatment and/or imaging of certain cancers and conditions expressing norepinephrine transporter.

In one or more embodiments, analogs of MIBG are provided. In one or more embodiments, the MIBG analogs are conjugated to an active agent. The MIBG analogs are preferably linked to the active agent via a cleavable linking moiety, such as an ester linkage or phosphate linkage. Linkages containing D- or L-amino acids (e.g., phenylglycine), including individual L- or D-amino acid residues and short peptides containing two or more L- or D-amino acid residues, are also contemplated in the invention. The side chain does not need to be a simple aliphatic chain.

Exemplary MIBG analogs attached via cleavable linking moieties include compounds of the formula:

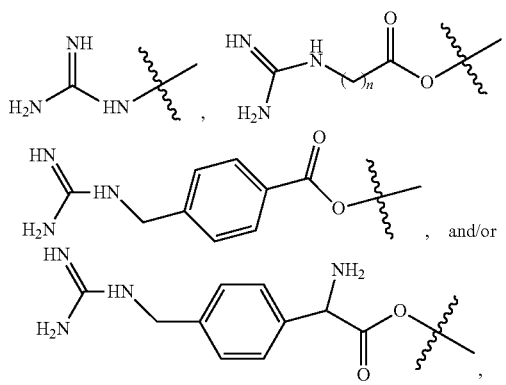

where n is 1-5 (and preferably 1, 2, or 5), and the wavy line indicates the point of attachment to the active agent.

In one or more embodiments, the active agent induces a therapeutic effect against a condition. In one or more embodiments, the active agent is effective for killing cancer cells, and specifically those undergoing DNA replication. In one or more embodiments, the active agent is labeled with a detectable label that generates a detectable signal.

Radiolabeled thymidine analogs, such as radioiodinated iododeoxyuridine (IUdR), are preferred active agents for use in certain embodiments of the invention. These active agents, conjugated to respective MIBG analog(s), are taken up by neuroblastoma cells via the same mechanism as MIBG. After the uptake, the active agent is processed intracellularly. When the cell enters scheduled or unscheduled (e.g., repair) DNA synthesis, the processed active agent participates in the DNA synthesis, is incorporated into the DNA, and kills the cancer cells. The conjugates can be radiolabeled with SPECT- and PET-compatible radionuclides. Therefore, they are appropriate for the individualized and comprehensive treatment strategies that comprise diagnostic imaging followed by a targeted molecular radiotherapy based on the imaging results. In one aspect, radiohalogens are used, such as $^{123}$I, $^{124}$I, $^{125}$I, $^{131}$I, $^{211}$At, $^{18}$F, $^{76}$Br, $^{77}$Br, or $^{80m}$Br.

Thymidine analogs when radiolabeled with an Auger emitter are virtually innocuous when located in the cytoplasm or extracellular spaces and therefore negative side-effects are significantly reduced. However, Auger electron-emitting radionuclides such as iodine-123, iodine-124, and iodine-125 are extraordinarily radiotoxic when either within the structure of DNA or in its immediate vicinity. For example, nearly all of the electron energy associated with the $^{125}$I decay is deposited within a sphere smaller than the cell nucleus. The use of these radioisotopes as active agents is beneficial because they are practically harmless when present in extracellular spaces. Thus, these compounds, if used alone or in combination therapies, will not increase the overall toxicity of the primary treatment, unlike iodine-131, yttrium-90 and lutetium-177.

Furthermore the MIBG conjugates are targeted to and taken up by neuroblastoma cells similar to MIBG, but once inside the cells these conjugates are processed into metabolites that participate in DNA synthesis and thus are retained by the cell more effectively. Exemplary compounds were designed to yield 5-radioiodo-2"-deoxyuridine and/or its 5'-monophosphate, both of which can participate in DNA synthesis.

The thymidine analogs may also be radiolabeled with other non-auger electron-emitting radionuclides, such as alpha-, beta-, and/or gamma-emitters. Unlike Auger electron emitters, these radioisotopes are radiotoxic even when outside the cell. Such isotopes would allow for the irradiation of neighboring cells, i.e., a bystander effect, which is beneficial, particularly if norepinephrine transporter expression is not uniform. The thymidine analog is, for the most part, taken up selectively by dividing malignant tumor cells. For example, radiolabeled IUdR can be used to incorporate iodine radionuclides into DNA in place of thymidine. These cells are located within a niche of nondividing cells, and the radioactive compound(s) can be indefinitely retained within the nucleus of the cancer cell following DNA incorporation. Nondividing cells will not incorporate radiolabeled thymidine analogs into their DNA, and most of the radiolabeled thymidine analogs that is not taken up by cancerous cells will be catabolized/dehalogenated rapidly ($t_{1/2}$ measureable in minutes) and thus, will not incorporate in the DNA of distant non-cancerous dividing cells.

Radiolabeled thymidine analogs, in one embodiment of this invention, may be chemically coupled to a cycloSaligenyl phosphotriester moiety:

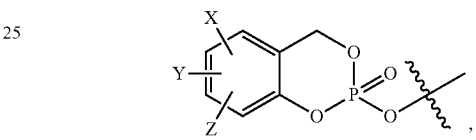

where X represents —H, —F, —Cl, or a substituted or unsubstituted $C_1$-$C_8$ alkyl, or $C_1$-$C_8$ alkoxy group; Y represents —H, a substituted or unsubstituted $C_1$-$C_8$ alkyl, $C_5$-$C_{14}$ aryl, or a $C_5$-$C_{14}$ aryloxy group; and Z represents —H, a substituted or unsubstituted $C_1$-$C_8$ alkyl, $C_5$-$C_{14}$ aryl, or a $C_5$-$C_{14}$ aryloxy group. In preferred embodiments, X is —H or —F, Y is —H or tert-butyl, and Z is —H, —$CH_3$ or tert-butyl.

Furthermore, since the radiolabeled thymidine analog is a small molecule it will not induce an immune response, which permits repeated dosing, continuous infusion, or similar modes of administration.

In one or more embodiments, exemplary active agents include thymidine analogs of the formula:

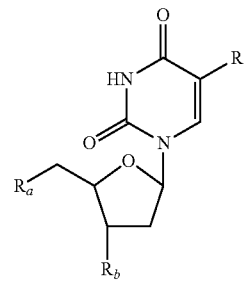

wherein:
R represents a halogen or radiohalogen;
$R_a$ represents —OH, a natural or unnatural L- or D-amino acid residue or a short peptide comprising natural or unnatural L- or D-amino acid residues, cycloSaligenyl phosphotriester moiety (as described above), or a MIBG analog (as described herein), and
$R_b$ represents a substituted or unsubstituted $C_1$-$C_6$ alkoxy, $C_1$-$C_8$ alkanoate group, —OH, a natural or unnatural L- or D-amino acid residue or a short peptide comprising natural or unnatural L- or D-amino acid residues, cycloSaligenyl phosphotriester moiety (as described above), or a MIBG analog (as described above), with the proviso that at least one of the $R_a$ and $R_b$ substituents represents an MIBG analog, as described herein.

Any of the alkyl or alkoxy groups described herein may be optionally substituted by at least one halogen, —OH, —SH, —NH$_2$, $C_1$-$C_4$ monoalkylamino, $C_1$-$C_4$ dialkylamino, —COOH, —CN, —NO$_2$, $C_1$-$C_4$ alkyl, $C_1$-$C_4$ alkoxy or phenyl group, and any of the foregoing aryl, aryloxy, and phenyl groups may be optionally substituted by at least one halogen, —OH, —SH, —NH$_2$, $C_1$-$C_4$ monoalkylamino, $C_1$-$C_4$ dialkylamino, —COOH, —CN, —NO$_2$, $C_1$-$C_4$ alkyl or $C_1$-$C_4$ alkoxy group.

It should be appreciated that chemical formulas depicted above may have one or more asymmetric centers and thus exist as stereoisomers, including diastereomers, with stereocenters named according to the Cahn-Ingold-Prelog system (R/S designation of stereocenters). Although the structural formulas set forth above are represented without regard to stereochemistry, it is intended to include all possible stereoisomers, which may be diastereomeric mixtures, as well as resolved, substantially pure optically active and inactive forms, and pharmaceutically acceptable salts thereof.

Stereoisomers of the compounds used in the practice of this invention can be selectively synthesized or separated into pure, optically-active or inactive form using conventional procedures known to those skilled in the art of organic synthesis. For example, mixtures of stereoisomers may be separated by standard techniques including, but not limited to, resolution of diastereomeric forms, normal, reverse-phase, and chiral chromatography, preferential salt formation, recrystallization, and the like, or by asymmetric synthesis either from enantiomerically or diastereomerically pure starting materials or by deliberate synthesis of target enantiomers or diastereomers. All of the various isomeric forms of the compounds of formulas above are within the scope of this invention, as are pharmaceutically acceptable salts of these compounds. Nonstereoselective syntheses produce the diastereometric mixture of cycloSaligenyl-phosphotriesters. Isomers may be separated by reverse phase HPLC and resolved according to their retention time as the slow and the fast diastereomers, as described in further detail below.

The phrase "enantiomeric excess" or "ee" is a measure, for a given sample, of the excess of one enantiomer over a racemic sample of a chiral compound and is expressed as a percentage. Enantiomeric excess is defined as 100*(er−1)/(er+1), where "er" is the ratio of the more abundant enantiomer to the less abundant enantiomer.

The phrase "diastereomeric excess" or "de" is a measure, for a given sample, of the excess of one diastereomer over a sample having equal amounts of diastereomers and is expressed as a percentage. Diastereomeric excess is defined as 100*(dr−1)/(dr+1), where "dr" is the ratio of a more abundant diastereomer to a less abundant diastereomer. The term does not apply if more than two diastereomers are present in the sample.

Preferably, where the "substantially pure" active agent compound above is provided as a diastereomer, the diastereomer is present at a diastereomeric excess of greater than or equal to about 80%, more preferably, at a diastereomeric excess of greater than or equal to about 90%, more preferably still, at a diastereomeric excess of greater than or equal to about 95%, more preferably still, at a diastereomeric excess of greater than or equal to about 98%, most preferably, at a diastereomeric excess of greater than or equal to about 99%.

As used herein, the term "alkyl" refers to saturated straight and branched chain hydrocarbon radicals, having 1-8 and preferably 1-4 carbon atoms.

The term "aryl" as used herein refers to an aromatic hydrocarbon radical composed of one or more rings and having 5 or 6-14 carbon atoms and preferably 5 or 6-10 carbon atoms, such as phenyl, naphthyl, biphenyl, fluorenyl, indanyl, or the like. Any aryl moiety of a compound described herein may be substituted as described above. The aryl moiety is preferably substituted or unsubstituted phenyl.

The term "halogen" or "halo" as used herein refers to F, Cl, Br, and I.

The term "radiohalogen" as used herein refers to an isotopic form of halogen that exhibits radioactivity. The radiohalogen is preferably selected from the group consisting of $^{123}$I, $^{124}$I, $^{125}$I, $^{131}$I, $^{211}$At, $^{18}$F, $^{76}$Br, $^{77}$Br, and $^{80m}$Br.

The term "alkoxy" refers to alkyl-O—, in which alkyl is as defined above.

The term "aryloxy" refers to the moiety —O-aryl, in which aryl is defined above.

The term "alkanoate" refers to the moiety —O—C(=O)-alkyl, in which alkyl is as defined as above.

The term "monoalkylamino" refers to the moiety —NH(alkyl), in which alkyl is as defined as above.

The term "dialkylamino" refers to the moiety —N(alkyl)$_2$, in which alkyl is as defined as above.

Also in accordance with the invention there are provided compounds of the formula selected from the group consisting of:

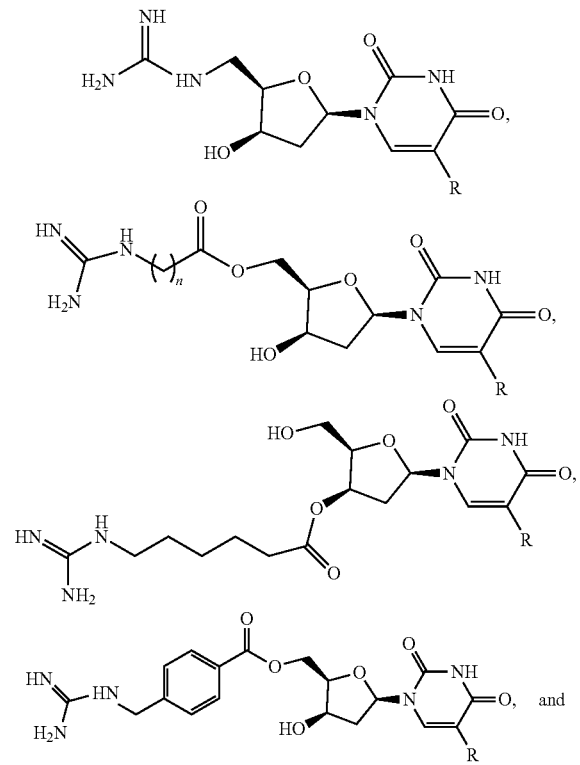

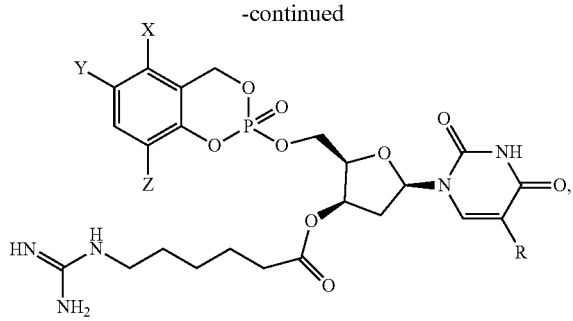

where n is 1-5 (preferably 1, 2, or 5), R is a radiohalogen, X represents H, F, Cl, or a $C_1$-$C_4$ alkyl, or $C_1$-$C_4$ alkoxy group, Y represents H or a $C_1$-$C_4$ alkyl group, and Z represents H or a $C_1$-$C_4$ alkyl group.

Pharmaceutically acceptable salts of any of the foregoing compounds may also be used. The term "pharmaceutically acceptable salts" as used herein refers to salts derived from non-toxic, physiologically compatible acids and bases, which may be either inorganic or organic. Useful salts may be formed from physiologically compatible organic and inorganic bases, including, without limitation, alkali and alkaline earth metal salts, e.g., Na, Li, K, Ca, Mg, as well as ammonium salts, and salts of organic amines, e.g., ammonium, trimethylammonium, diethylammonium, and tris-(hydroxymethyl) methylammonium salts. The compounds of the invention also form salts with organic and inorganic acids, including, without limitation, acetic, ascorbic, lactic, citric, tartaric, succinic, fumaric, maleic, malonic, mandelic, malic, phthalic, salicyclic, hydrochloric, hydrobromic, phosphoric, nitric, sulfuric, methane sulfonic, naphthalene sulfonic, benzene sulfonic, para-toluene sulfonic and similar known, physiologically compatible acids. In addition, when a compound contains both a basic moiety and an acidic moiety, zwitterions ("inner salts") may be formed and are included within the term "salt(s)" as used herein.

These MIBG analog-active agent conjugates are less toxic than the parent compound ($^{131}$IMIBG) and are metabolized in a way that allows for their incorporation into DNA, thereby increasing their retention within the cancer cell. They mimic MIBG in their mechanism of neuroblastoma targeting, however, unlike MIBG they subsequently undergo intracellular processing and their metabolites are efficiently incorporated into the DNA of neuroblastoma cells, which have high proliferation activities, i.e., these of the high-risk and aggressive disease. Moreover, the structure of these drugs, in some aspects, include phosphotriester moieties allowing for a "lock-in" mechanism, which traps the metabolites within the cancer cells, thereby assuring their sustained availability throughout the cell cycle.

Therapeutic and/or diagnostic preparations comprising the conjugates of this invention may be formulated for administration with a biologically acceptable vehicle, which may include the patient's own serum or serum fractions. Other suitable vehicles include liposomes and similar injectable suspensions, saline, activated carbon absorbents, and solutions containing cyclodextrins such as alphadex and betadex. Additionally, IUdR compounds may be derivatized, e.g., by esterification of available hydroxyl groups, with long chain fatty acids to increase the circulation half-life of the compounds. The concentration for diagnostic uses of the conjugate in the chosen vehicle should normally be from about 0.1 mCi/mL to about 10 mCi/mL. The concentration for therapeutic uses of the conjugate in the chosen vehicle should normally be from about 1 mCi/mL to about 100 mCi/mL, and preferably from about 5 to about 20 mCi/mL. These concentrations may vary depending on whether the method of administration is intravenous, intraperitoneal, or intratumoral. In all cases, any substance used in formulating a therapeutic preparation in accordance with this invention should be virus-free, pharmaceutically acceptable, and substantially non-toxic.

As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. It includes any and all solvents, diluents, or other liquid vehicle, dispersion or suspension aids, surface agent agents, isotonic agents, thickening or emulsifying agents, preservatives, and the like as suited for the particular mode of administration desired. Remington: The Science and Practice of Pharmacy, 20th edition, A. R. Genaro et al., Part 5, Pharmaceutical Manufacturing, pp. 669-1015 (Lippincott Williams & Wilkins, Baltimore, Md./Philadelphia, Pa.) (2000)) discloses various carriers used in formulating pharmaceutical compositions and known techniques for the preparation thereof. A pharmaceutically-acceptable vehicle or excipient would naturally be selected to minimize any degradation of the conjugate or other ingredients and to minimize any adverse side effects in the subject, as would be well known to one of skill in the art. Except insofar as any conventional pharmaceutical carrier medium is incompatible with the compounds of the present invention, such as by producing an undesirable biological effect or otherwise interacting in an deleterious manner with any other component(s) of a formulation comprising such compounds, its use is contemplated to be within the scope of this invention. It is noted in this regard that administration of the compounds of this invention with any substance that competes therewith for norepinephrine transporter binding is to be avoided. Pharmaceutically-acceptable ingredients include those acceptable for veterinary use, and will depend on the route of administration.

If necessary, the action of contaminating microorganisms may be prevented by various anti-bacterial and/or anti-fungal agents, such as parabens, chlorbutinol, phenyl, sorbic acid, thimerosal and the like. It will often be preferable to include in the formulation isotonic agents, for example, glucose or sodium chloride, as well as aqueous solutions such as normal (n.) saline (~0.9% NaCl), phosphate buffered saline (PBS), sterile water/distilled autoclaved water (DAW), aqueous dextrose solutions, aqueous glycerol solutions, and the like. Additionally, free-radical scavengers and antioxidants such as ascorbic acid and the like may be employed to allow for a longer storage of the radioactive compound.

The present invention provides methods of using the above-described conjugates or preparations for treating and diagnosing cancers and other conditions comprising cells expressing norepinephrine transporter, especially neuroblastoma. In general, the methods comprise administering the MIBG analog-active agent conjugate to a subject, such as through an intravenous line or other suitable route of delivery. In some aspects, the treatment protocol can also include administration of a sensitizer (i.e., an agent that makes the cells more susceptible to radiation therapy, or uptake of the conjugate). For therapeutic applications, the MIBG analog-active agent conjugate will typically be administered in a therapeutically effective amount. As used herein, a "therapeutically effective" amount refers to the amount that will elicit the biological or medical response of a tissue, system, or subject that is being sought by a researcher or clinician, and in particular elicit a detrimental effect as against the cancer cells (while sparing healthy tissue). One of skill in the art recognizes that an amount may be considered therapeutically "effective" even if the condition is not totally eradicated or prevented, but it or its symptoms and/or effects are improved or alleviated partially in the subject. In general, a therapeutically effective amount will normally be a dose that provides from about 1 mCi (37 MBq)-20 mCi (740 MBq) of radioactivity per kg of the subject's body weight. Advantageously, the conjugates are selectively taken up by the target cells (e.g., neuroblastoma), where they are processed such that the active agent participates in the DNA synthesis process. The targeted delivery of radionuclides to cancer cells in the manner described herein produces strong cytotoxic activity, in that the radionuclide is introduced into the DNA of the multiplying cells, where it induces DNA strand breaks in the double helix. Moreover, by delivering radiolabeled agents to a specific site and relying on mechanisms operational at the site of delivery to release the radiolabeled agent, the usual in vivo degradation pathways are by-passed, bioavailability of the radiolabeled agent is improved, and more tumor cells are exposed to the cell killing effect of the radiation as they enter into the S phase.

The compounds of the invention may be administered as such, or in a form from which the active agent can be derived, such as a prodrug. A prodrug is a derivative of a compound described herein, the pharmacologic action of which results from the conversion by chemical or metabolic processes in vivo to the active compound. Prodrugs include, without limitation, ester, acetal, imine, carbamate, succinate, and phosphate derivatives of the compounds of formula I, above. Other prodrugs may be prepared according to procedures well known in the field of medicinal chemistry and pharmaceutical formulation science. See, e.g., Lombaert et al., J. Med. Chem., 37: 498-511 (1994); and Vepsalainen, Tet. Letters, 40: 8491-8493 (1999).

The method of treating cancer described herein will normally include medical follow-up to determine the effectiveness of the conjugate in eradicating the cancer cells in a patient undergoing treatment. Again, the cytotoxic effects of the methods of the invention are induced only when one or more of the compounds described herein are incorporated into the DNA of rapidly dividing tumor cells. This dependence of radiotoxicity on the participation of the compound in DNA synthesis, in combination with relatively rapid pharmacokinetics, limits the exposure of normal tissue to radiation. In other words, the compound(s) that remain(s) in systemic circulation, or enter(s) normal tissue or organs, is (are) essentially innocuous. Accordingly, the compounds of the invention may be administered frequently and without appreciable adverse effects.

The conjugates can also be used for diagnosis of certain cancers and conditions. The method comprises administering to a subject a diagnostically effective amount of labeled conjugate, and then imaging the cancer cells using SPECT or PET imaging depending on the radionuclide used. A diagnostically effective amount of the conjugate for diagnostic applications will generally be an amount sufficient to provide between 0.1 mCi and 10 mCi of radioactivity. For the determination of norepinephrine expression, the imaging can commence immediately after the administration. To detect DNA uptake, imaging may begin 1 hour after administration. Notably, when using longer lived radioisotopes, imaging can occur at least daily for 7 days or longer to assess the tumor growth kinetics.

This method can be adapted to diagnose and track disease progression for neuroblastoma or other cancers involving overexpression of norepinephrine transporter, such as gastrointestinal neuroendocrine tumors, such as carcinoid and pancreatic islet cell tumors. For example, it can be used to pinpoint the location of the main neuroblastoma tumor as well as to see if the cancer has spread to other areas of the body such as the bones, bone marrow, liver, lymph nodes, lungs, and the like.

The analogs of the present invention can also be used for diagnostic imaging using scintigraphic imaging techniques and tracking of disease progression for other diseases that involve norepinephrine such as cardiovascular diseases including but not limited to heart failure, myocardial ischemia, and diabetes and neurologic diseases including but not limited to psychiatric disorders, attention deficit hyperactivity disorder, Parkinson' disease, and dementia with Lewy bodies. The analogs of the present invention can also be used to estimate cardiac sympathetic innervations. For example, the analog conjugates can be administered to a patient as an imaging agent for cardiac sympathetic imaging using suitable imaging technics. For example, SPECT images of the heart allow evaluation of the regional sympathetic activity based upon uptake and distribution of the imaging agent, where reduction in sympathetic nervous function in the heart is measured by reduced myocardial uptake of the MIBG analog (and is an indicator of poor prognosis for heart failure patients). Likewise, imaging to detect uptake of the analogs can be performed to identify areas of myocardial infarction, and/or areas of acute and/or chronic ischemia, which are characterized by decreased uptake of the MIBG analogs. Essentially, existing techniques related to using radiolabeled MIBG for various cardiovascular conditions can be adapted for use with the inventive MIBG analog-active agent conjugates. In such techniques, the MIBG analog is administered to the subject, followed by sequential imaging of the thorax over a period of time to establish a baseline (first image, e.g., at 15 minutes post-administration) and a delayed image (second image, e.g., at 4 hours post-administration). Comparison of the two images provides information regarding uptake, storage, and release of the analog, which indicate activity and functional capabilities of the imaged tissues, and even allows calculation of various diagnostic parameters known to those in nuclear medicine.

The determination of an appropriate dose of conjugate, either therapeutic or diagnostic, for a particular patient will, of course, be determined based on the type and stage of the patient's cancer and the judgment of the attending medical oncologist or radiologist, as the case may be. For both therapeutic and diagnostic applications, the conjugates useful in the method of the invention can be imaged in vitro, ex vivo, and in vivo using various imaging techniques depending upon the moiety attached to the compound which enables the imaging. For instance, by labeling a compound of the method of the invention with $^{19}$F, the compound could be imaged in vitro, ex vivo, and in vivo using magnetic resonance spectroscopy (MRS). For methods of the invention that utilize radiolabeled compounds, those methods could utilize scintigraphic imaging techniques such as positron emission tomography (PET) or single photon emission computed tomography (SPECT).

As used herein, the expression "tumor activity", refers to a tumor's presence, progression, regression or metastasis in a subject, or to a reduction of tumor size due to therapeutic intervention. As used herein, the expression, "tumor size", includes all methods of quantifying the size of a tumor which include, but are not limited to, weight, mass, and volume of the tumor ex vivo and in vivo. Therefore, "baseline tumor size", as used herein, refers to the size of the tumor at or near the time of initial diagnosis, and prior to any form of treatment, so as to provide a starting point from which changes, or lack thereof, to the tumor's size can be quantified.

As used herein, the term "diagnosis" or "diagnostic", includes the provision of any information concerning the existence, non-existence or probability of a malignant tumor or a tumor composed of cancer cells in a patient. It further includes the provision of information concerning the type or classification of the disorder or of symptoms which are or may be experience and in connection with it. It encompasses prognosis of the medical course of the condition.

A kit comprising a vessel containing a conjugate, above, and a pharmaceutically acceptable carrier medium is also provided. The kit may optionally include one or more of catheter tubing, syringe, antibacterial swabs, all antiseptically packaged, as well as instructions for practicing the above-described methods.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

The following examples describe the synthesis of the various conjugates of the present invention, as well as biological testing of certain of the conjugates. These examples are provided for illustrative purposes only and are not intended to limit the scope of the invention in anyway.

EXAMPLES

The following examples set forth methods in accordance with the invention. It is to be understood, however, that these examples are provided by way of illustration and nothing therein should be taken as a limitation upon the overall scope of the invention.

Example 1

Synthesis

Figure 1B:
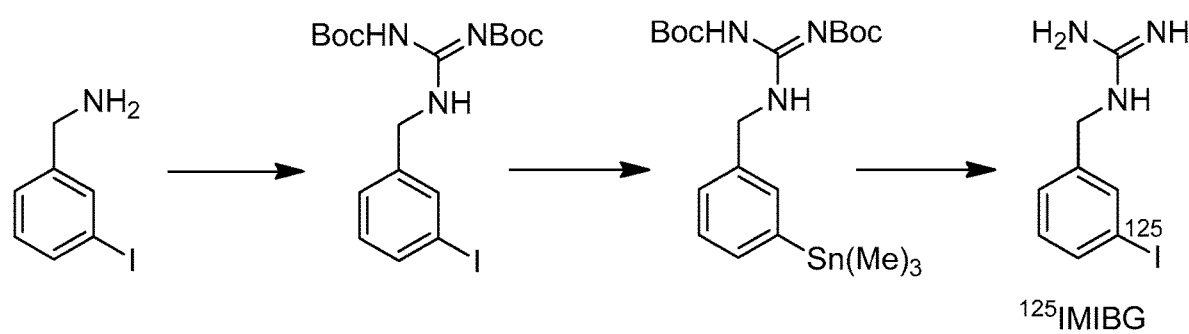
FIG. 1B shows the reaction scheme used to prepare 3-[$^{125}$I]-iodobenzylguanidine (30)
Figure 1B:
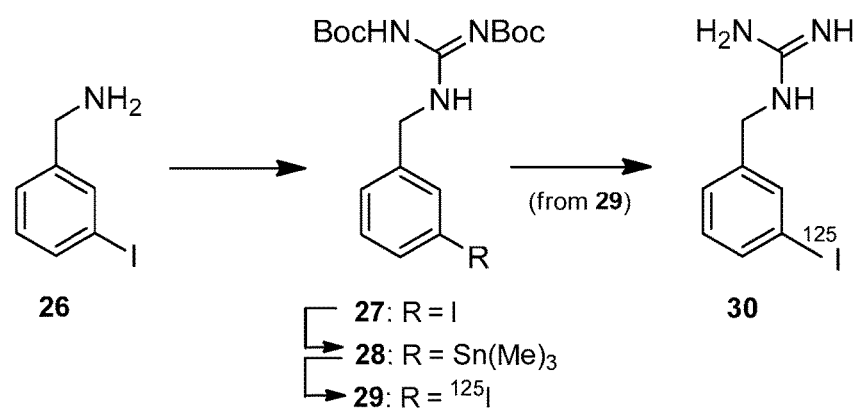

A single radioiodination method (Scheme 1 and 2) was used to prepare the guanidinoalkyl esters of 5-[$^{125}$I]-iodo-2'-deoxyuridine: 13, 17a-b, 21, 25, along with of 5-[$^{125}$I]-iodo-5'-N-guanidino-2',5'-dideoxyuridine (9) and 3-[$^{125}$I]-iodobenzylguanidine (30) (See FIGS. 1A and 1B). The process involved three consecutive steps: the initial preparation of nonradioactive iodo analogues, with subsequent stannylation of attained iodides to the corresponding stannanes and the non-carrier-added electrophilic iodo destannylation of resultant organotin precursors, ultimately leading to the target [$^{125}$I]-iodinated products. This well proven radioiodination sequence, based on modified Stille coupling procedure, served efficiently in this example.

The synthesis of nonradioactive iodo analogues is described herein. A suitably protected derivative of IUdR (1) was reacted at first with the corresponding N-Boc-protected amino acid (using DCC/DMPA activation), the amine group of the resulting amino ester of IUdR was deprotected, and the guanidinylation of the free amino group was performed with N,N'-bis(tert-butyloxycarbonyl)-N''-trifluoromethane-sulfonyl guanidine.

In preparation of 5-iodo-5'-N—[N',N''-bis(tert-butyloxycarbonyl)guanidino]-2',5'-dideoxyuridine (6), the necessary 5-Iodo-5'-amino-2',5'-dideoxyuridine was initially attained from 5-iodo-5'-O-p-tolylsulfonyl-2'-deoxyuridine (5) in three steps: first, 5-iodo-5'-O-p-tolylsulfonyl-2'-deoxyuridine (5) was reacted with lithium azide, to give 5-iodo-5'-azido-2',5'-dideoxyuridine; second, the 5-iodo-5'-azido-2',5'-dideoxyuridine was reacted with triphenylphosphine; and third, the product was hydrolyzed with concentrated ammonium hydroxide. Somewhat higher yield of 5-iodo-5'-amino-2',5'-dideoxyuridine was gained, however, starting from 5'-azido-2',5'-dideoxyuridine, which hydrogenated to 5'-amino-2',5'-dideoxyuridine, and reacting with mercuric acetate and a crude 5-mercuriacetate of 5'-amino-2',5'-dideoxyuridine iodinated with elemental iodine. To acquire guanidinoalkyl ester (10), IUdR (1) was 5'-O-silylated with TBDMSCl in pyridine to yield (4) (in 79%), which was reacted with 6-N-Boc-aminohexanoic acid. The 5'-O-position of the product was deprotected using 2% TBAF/THF, the N-Boc-group was cleaved in 20% TFA/MeCN, and the guanidinylation of the freed amino group furnished (10) in 67% of the overall yield.

Preparations of guanidino esters (14a), (14b) and (22), all began with 5-iodo-3'-O-levulinyl-2'-deoxyuridine (3), obtained from 5-iodo-5'-O-trityl-2'-deoxyuridine (2) in the reaction with 4-oxopentanoic acid (DCC/DMAP activation, ~78% yield) and followed by the cleavage of trityl group with ZrCl$_4$ in CH$_3$CN. The 3'-O-Lev protected deoxyuridine (3) was then used in similarly carried out reactions with: Boc-β-alanine, 6-(Boc-amino)-caproic acid, and with 4-(Boc-aminomethyl)benzoic acid, to yield correspondingly: 5-iodo-5'-O-(3-N-Boc-aminopropionyl)-, 5-iodo-5'-O-(6-N-Boc-aminohexanonyl)-, and 5-iodo-5'-O-[4-(N-Boc-aminomethyl)-benzoyl]-derivatives of 3'-levulinyl-2'-deoxyuridine. These, after elimination of the N-Boc amino protection, guanidinylation, and final cleavage of the 3'-O-Lev group, gave the target guanidinoalkyl esters, in satisfactory yields: (14a) (73%), (14b) (69%), and (22) (67%).

Formation of guanidino ester (18), started with 5-iodo-5'-O-[cyclo-3,5-di(tert-butyl)-6-fluorosaligenyl]-2'-deoxyuridine monophosphate, attained via phosphorus(III) route, in two steps: first, 5-iodo-3'-O-levulinyl-2'-deoxyuridine (3) was coupled with cyclo-3,5-di(tert-butyl)-6-fluoro chlorophosphite in the presence of N,N-diisopropylethylamine; and second, the generated phosphite, oxidized directly with tert-butyl hydroperoxide, furnished the expected cyclosaligenyl deoxyuridine, which again, after cleavage of 3'-O-Lev group and the subsequent reaction with 6-(Boc-amino)caproic acid, gave 5-iodo-5'-O-[cyclo-3,5-di(tert-butyl)-6-fluorosaligenyl]-3'-O-(6-N-Boc-aminohexanonyl)-2'-deoxyuridine monophosphate. Removal of N-Boc protecting group, followed by the guanidinylation, led to the guanidinoalkyl ester (18) in 79% overall yield.

Organotin precursors were obtained through stannylations of iodides with hexamethylditin, catalyzed by bis-(triphenylphosphine)palladium(II) dichloride in the presence of triethylamine. Reactions were carried out under nitrogen in refluxed dioxane or ethyl acetate, depending on the solubility of starting iodoester. In order to achieve ≥98% purity of separated stannanes, the successive HPLC purifications were often necessary. However once purified, anhydrous samples of stannanes stored with the exclusion of light under nitrogen at –20° C. did not decompose excessively (≤6% by the HPLC analysis) and were suitable for the immediate [$^{125}$I]-iododestannylation. Elevated hydrophobicities of stannanes, always outweighing hydrophobicities of matching iodides, allowed for a complete separation of the trimethyltin precursor excess from the [$^{125}$I]-iodinated product in a single HPLC purification, even when a large volume of the crude reaction mixture was loaded onto the column. The non-carrier-added [$^{125}$I]-iodinations were conducted within a range of 22.2-148 MBq in acetonitrile, using ~100 μg of stannane, a solution of hydrogen peroxide to oxidize sodium [$^{125}$I]-iodide, and TFA to acidify the reaction mixtures. HPLC analyses indicated consistently high radiochemical yields of 80-92% and radiochemical purity of ≥95%, across the series of prepared [$^{125}$I]-iodides. The inevitable proton destannylated side product (2-6%), detected in every crude reaction mixture, originated primarily from older (often stored up to six months), frozen samples of stannanes, and its level was increasing along with the storage time. The HPLC co-injections of the [$^{125}$I]-iodinated products with corresponding non-radioactive iodo analogues were performed to confirm the identity of radioiodinated compounds. Characterizations of all nonradioactive compounds were carried out by means of $^1$H, $^{13}$C, $^{119}$Sn and $^{31}$P NMR and high-resolution mass spectrometry, and scrupulous HPLC analyses.

The synthesis details of all required 5'-O-, 3'-O-(N-tert-butyloxycarbonyl)-aminoalkyl esters of IUdR and N,N'-bis(tert-butyloxycarbonyl)-3-iodobenzylguanidine (26), along with the HPLC monitoring, separation and analysis of the products in conducted radioiodinations, as well as the stability determination of target compounds, and comprehensive HPLC analysis of compounds 3 through 30 are delineated in Example 2.

Example 2

Experimental and Analysis

Materials and Methods

Chemicals and reagents purchased from commercial suppliers were used without further purification, unless explicitly indicated. Solutions of sodium [$^{125}$I]iodide in 1×10$^{-5}$ NaOH (pH 8-11), with specific activities of 79735 GBq/mmol were obtained from PerkinElmer (Billerica, Mass.). Radioactivity was measured with Minaxi γ-counter (Packard, Waltham, Mass.) and a dose calibrator (CapIntec Inc., Ramsey, N.J.). Analytical TLC was carried out on precoated with a 0.2 mm layer of silica plastic plates (normal phase Merck 60 F$_{254}$), and spots were visualized with either short wave UV or iodine vapors. Flush column chromatography was performed using Merck silica gel 60 (40-60 μM) as the stationary phase. Compounds were resolved and their purity evaluated by the HPLC analyses conducted on Gilson (Middleton, Wis.) and ISCO (Lincoln, Nebr.) systems, with 5-μm, 250×4.6 mm analytical columns, either Columbus C8 (Phenomenex, Torrance, Calif.) or ACE C18 (Advanced Chromatography Technologies, www.ace-hplc.com). Columns protected by guard filters were eluted at a rate of 0.8 mL/min with various gradients of CH$_3$CN (10-95%) in water, with or without TFA (0.07%, w/v). Two variable wavelength UV detectors were used, UVIS-205 (Linear, Irvine, Calif.) and UV116 (Gilson), jointly with the sodium iodide crystal Flow-count radioactivity detector (Bioscan, Washington, D.C.), connected to the outlet of the UV detector. Both signals were monitored and analyzed simultaneously.

All the target nonradioactive compounds were found to be ≥98% pure by the rigorous HPLC analysis, with the integration of a peak area (detected at 220 and/or 280 nm). Radioiodinated products were identified and evaluated through the independently prepared non-radioactive reference compounds, by comparing UV signals of the non-radioactive standards with signals from radio-TLC($R_f$) and radio-HPLC ($t_R$) of the radioactive products. Before testing the biological activities and stability, each final target compound was once again purified by HPLC using linear gradient of EtOH (0-70%) in phosphate buffer (100 mM, pH 6.1) to eliminate the presence of TFA and CH$_3$CN in tested samples. NMR spectra were recorded at ambient temperature in (CD$_3$)$_2$SO or CDCl$_3$ on a Varian INOVA 500 MHz NMR instrument spectrometer (Palo Alto, Calif.) and chemical shifts are given as δ (ppm) relative to TMS internal standard, with J reported in Hertz. Deuterium exchange and decoupling experiments were performed to further assist signals assignments of protons. $^{119}$Sn NMR spectra were recorded with proton decoupling. High resolution (ESI-HR) positive ion mass spectra were acquired on an LTQ-Orbitrap mass spectrometer with electrospray ionization (ESI). Samples were dissolved in 70% methanol. Two μL aliquots were loaded into a 10-μL loop and injected with a 5 μL/min flow of 70% acetonitrile, 0.1% formic acid. FAB high-resolution (FAB-HR) mass spectra analyses (positive ion mode, 3-nitrobenzyl alcohol matrix) were performed by the Washington University Mass Spectrometry Resource (St. Louis, Mo.).

The Tr group was cleaved as follows: the crude product, dissolved in MeCN (10-20 mL), and ZrCl$_4$ (1.2-1.6 molar equiv) was added. The mixture was stirred at room temperature for about 1 h (TLC monitoring). The solvent was evaporated in a vacuum, and the residue was treated with EtOAc (50 mL) and water (50 mL). The organic layer was washed with brine, dried over MgSO$_4$, and the residue purified on a silica gel column.

The cleavage of 3'-O-Lev group: the crude product was dissolved in pyridine (2 mL) and added to a stirred, cooled (on an ice-water bath) solution of hydrazine hydrate (1.5 mL) in pyridine (3 mL) containing acetic acid (2.2 mL). The stirring continued for 5 min, then water (40 mL) and EtOAc (50 mL) were added. The organic layer was separated and washed with 10% aqueous solution of NaHCO$_3$ (20 mL), water (20 mL), dried over MgSO$_4$, and evaporated. The residue was purified on a silica gel column.

General Procedure A. Preparations of -3'-O- and -5'-O—[(N,N'-bis(tert-butyloxycarbonyl)-N'''-alkylcarboxy)guanidino] esters of 5-Iodo-2'-deoxyuridine: (10), (14a-b), (18), (22)

At first, the Boc group of each starting 5-iodo-3'-O- or -5'-O—(N-tert-butyloxycarbonyl)aminoalkylcarboxy)-2'-deoxyuridine was cleaved with ~15% TFA in DCM or MeCN. When the reaction was completed (monitoring by TLC), the mixture was evaporated under vacuum at room temperature, and the resulting oily residue was treated with 15 mL of EtOAc/hexane (1:1) and sonicated briefly a few times. The solvent was carefully decanted from the formed solid, the product washed with Et$_2$O and drawn off again. This washing procedure was repeated, and then the remaining TFA salt was kept under vacuum to dry. A resulting crude TFA salt of 5-iodo-3'-O- or 5-iodo-5'-O-aminoalkylcarboxy-2'-deoxyuridine (1.0 molar equiv) was suspended in DCM, placed on an ice bath, and to the stirred mixture TEA (1.05 molar equiv) was added, immediately followed by N,N'-bis (tert-butoxycarbonyl)-N'''-trifluoromethanesulfonyl guanidine (1.1 molar equiv). The mixture was stirred for 5 min, and to a resulting clear solution a second portion of TEA (1.0 molar equiv) added. Stirring continued for 2-6 h (TLC monitoring) at room temperature. Upon the completion, an excess of amines and triflic amide were removed by aqueous workup with 5% citric acid and saturated brine. Organic phase was dried over MgSO$_4$, filtered, and evaporated. The crude products were purified on a silica gel column with gradients of MeOH in DCM or EtOAc in hexanes. In preparations conducted with 3'-O-levulinyl-protected deoxyuridines, the resulting solid was directly dissolved in pyridine (2 mL) and added to a stirred, cooled (on an ice-water bath) solution of hydrazine hydrate (1.5 mL) in pyridine (3 mL), containing acetic acid (2.2 mL). The stirring continued for ~5 min, and water (40 mL) and EtOAc (50 mL) were added. The organic layer was separated, washed with 10% aqueous solution of NaHCO$_3$ (20 mL), water (20 mL), dried over MgSO$_4$, and evaporated.

General Procedure B. Preparations of Trimethyltin Precursors: (7), (11), (15a-b), (19), (23), and (28)

Stirred solution of each 5-iodo-3'-O-, or 5-iodo-5'-O—[(N,N'-bis(tert-butyloxycarbonyl)-N'''-alkylcarboxy)guanidino]-2'-deoxyuridine: (10), (14a-b), (18), (22), 5-Iodo-5'-N—[N',N''-bis(tert-butyloxycarbonyl)guanidino]-2',5'-dideoxyuridine (6), or N,N'-bis(tert-butyloxycarbonyl)-3-iodobenzylguanidine (26) (1.0 equiv), in ethyl acetate or dioxane (depending on solubility), containing hexamethylditin (1.25-1.70 equiv), triethylamine (2-4 equiv) and dichloro-bis-(triphenylphosphine) palladium II catalyst (0.10 equiv), was gently refluxed under a nitrogen atmosphere, until the starting iodide was detectable (1-3 h). The reaction progress was checked often by TLC. After cooling to ambient temperature, the mixture was freed from the remaining catalyst by filtration through a thin pad of silica (washed with EtOAc/hexanes, 2:1) and evaporated. Two major products were always present: the corresponding trimethylstannane (with high TLC mobility), isolated in 30-62% yield and the deiodinated starting iodide (slower on TLC). The crude products were separated and purified by repeating a silica gel column chromatography, with the various gradients of EtOAc in hexanes (2-5:10) and/or MeOH in DCM or CHCl$_3$ (0.4-0.7:10). In order to reach ≥98% purity of the stannylated products, the successive HPLC purifications were often required. However once purified, anhydrous samples of stannanes (~100 μg) stored for up to six months, with the exclusion of light under nitrogen at −20° C., did not decompose excessively (≤6% by the HPLC analysis), and were suitable for the immediate iododestannylation.

General Procedure C. Preparations of [$^{125}$I]-Radioiodinated-3'- and -5'-Guanidino-N-alkylcarboxy Esters of 5-[$^{125}$I]-Iodo-2'-deoxyuridine (13, 17a-b, 21, 25), 5-[$^{125}$I]-Iodo-5'-N-guanidino-2',5'-dideoxyuridine 9 and 3-[$^{125}$I]-Iodobenzyl-guanidine (30)

Into a glass tube containing the selected tin precursor: (7), (11), (15a-b), (19), (23) or (28) (~100 μg, 0.1-0.2 μmol) in MeCN (50 μL), a solution of Na$^{125}$I/NaOH (10-50 μL, 22.2-148 MBq) was added, followed by a solution of 30% H$_2$O$_2$ in water (5 μL) and 2 min later, a solution of TFA (50 μL, 0.1 N in MeCN). The resulting mixture, briefly vortexed and/or sonicated, was left for 15 min at room temperature and then quenched with a solution of Na$_2$S$_2$O$_3$ (90-100 μg) in water (60 μL). At this point, one of the two pathways was implemented. Under the first pathway, the reaction mixture was taken up into a syringe and the reaction tube washed twice with a solution of MeCN/H$_2$O (50 μL, 1:1-3, determined by the trimethylstannane solubility). The reaction mixture and washes were combined, injected onto the HPLC system and separated on the C8 or C18 reverse phase column with a linear gradient of MeCN in water. Eluted fractions with one of radioiodinated products: (8), (12), (16a-b), (20), (24), (29) were pooled, evaporated with a stream of dried nitrogen or else were dissolved in dry MeCN (~18.5 MBq/mL) for further analysis or storage. Next, to remove the Boc-protective groups from guanidine, neat TFA (100 μL) was added to a dried residue of [$^{125}$I]-iodinated product and the resulting mixture was heated in a sealed vial at 65-85° C. for 20-35 min. After cooling, the mixture diluted with CH$_3$CN (200 μL) was evaporated repetitively with a stream of nitrogen, each time leaving ~20 μL of the liquid in the reaction vial, to prevent sticking and losses of the product to the walls of the vial. This process was repeated at least three times, to ensure that an excess of TFA was evaporated.

The residue was then dissolved in a solution of 50% MeCN in water, injected onto the HPLC system, and separated on the C18 reverse phase column with a gradient of MeCN in water, with both solvents containing 0.07% TFA (v/v), as the eluant. Under the second pathway, if the initial separation of Boc-protected radioiodinated product was not essential, a crude radioiodination mixture, quenched with a solution of Na$_2$S$_2$O$_3$, was evaporated with a stream of dried nitrogen, and/or kept under a high vacuum, then was directly treated with neat TFA at elevated temperature, and separated using HPLC, as described previously. To fully eliminate the presence of TFA and CH$_3$CN, the combined HPLC fractions containing a separated product were evaporated with a stream of nitrogen, and to the residue, ethanol (80 μL) was added, followed by potassium phosphate buffer (100 μL, 100 mM PB, pH 6.1). The resulting mixture was injected again on HPLC reverse phase column and eluted with a linear gradient of EtOH in potassium phosphate buffer. In every HPLC separation or analysis of radiolabeled products, the eluate from a column was monitored with a radioactivity detector connected to the outlet of the UV detector (detection at 220 and 280 nm). Solutions containing the product were reconstituted in a preferred solvent and the required concentration, and then filtered through a sterile (Millipore 0.22 μm) filter into a sterile evacuated vial. Identities of the radiolabeled products were confirmed through the evaluation of the UV signals of nonradioactive iodo-analogs (prepared independently) with the UV signals of radioactive compounds, and/or by comparing $R_f$ obtained from the radio-TLC and $t_R$ from the radio-HPLC analysis. All radiolabeled products, if kept in a solution overnight at ambient temperature, were purified one more time shortly before conducting further experiments, although the HPLC analysis rarely indicated less than 95% of the radiochemical purity.

5-Iodo-5'-N—[N',N"-bis(tert-butyloxycarbonyl)guanidino]-2',5'-dideoxyuridine (6)

This compound was prepared by direct guanidinylation of 5-Iodo-5'-amino-2',5'-dideoxyuridine with N,N'-bis(tert-butyloxycarbonyl)-N"-trifluoromethanesulfonyl guanidine in the presence of triethylamine. The starting 5-Iodo-5'-amino-2',5'-dideoxyuridine was acquired using known methods, with a few modifications applied.

Method A:

The 5-iodo-5'-O-p-tolylsulfonyl-2'-deoxyuridine (5) was reacted with lithium azide, to afford 5-iodo-5'-azido-2',5'-dideoxyuridine, which was treated with triphenylphosphine and a crude product hydrolyzed with concentrated ammonium hydroxide. These initial preparations proceeded as follows:

5-Iodo-5'-O-p-tolylsulfonyl-2'-deoxyuridine (5)

To a stirred solution of 5-iodo-2'-deoxyuridine (5.32 g, 15 mmol) in dried pyridine (100 mL) placed in an ice bath, p-toluenosulfonyl chloride (3.10 g, 16 mmol) was added in small portions. The resulting clear mixture was kept at 5° C. overnight. An additional p-toluenosulfonyl chloride (0.5 g, 2.6 mmol) was added and the stirring continued for another 10 h at room temperature. The mixture was then treated with ethanol (50 mL), evaporated under reduced pressure, and triturated with ice-water. The crude product was filtered off, treated with hot toluene (70 mL), then cooled, filtered, and dried. Recrystallization from ethanol yielded 3.62 g (47%) of the product. $R_f$ value 0.64 (DCM/MeOH, 10:1), 96.7% pure by HPLC analysis at 280 nm. mp 163-165° C. dec. $^1$H NMR (DMSO-d$_6$, 500 MHz) δ 11.63 (s, 1H, NH), 7.98 (s, 1H, H6-uridine), 7.84-7.76 (m, 2H, H2-Ph, H6-Ph), 7.71-7.58 (m, 3H, H3-Ph, H4-Ph, H5-Ph), 6.17 (dd, H1', $^3J_{1',2'}$=6.42 Hz, $^3J_{1',2''}$=4.60 Hz), 4.21-4.16 (m, H3', OH), 3.87-3.48 (m, 3H, H4', H5'), 2.23-2.09 (m, 2H, H2') ppm.

5-Iodo-5'-azido-2',5'-dideoxyuridine

A mixture of (5) (3.12 g, 6.52 mmol) and lithium azide (0.49 g, 9.8 mmol) in DMF (40 mL) was heated to ~70° C. for 2 h with stirring. After cooling, the solvent was evaporated to dryness under reduced pressure, and to the residue treated with 50% aqueous ethanol, Dowex 50 (H$^+$) resin (12 g) was added. The mixture was stirred at room temperature for 1 h and then was filtered, and solvents were evaporated in a vacuum. The formed white solid was collected and recrystallized from 2-propanol to afford 1.66 g (67%) of the product (95.8% pure by HPLC analysis at 280 nm). mp 186-187° C. dec. $^1$H NMR (DMSO-d$_6$, 500 MHz) δ 10.87 (s, 1H, NH), 7.79 (s, 1H, H6-uridine), 5.97 (dd, H1', $^3J_{1',2'}$=6.45 Hz, $^3J_{1',2''}$=4.65 Hz), 3.87-3.76 (m, 1H, H4'), 3.72-3.64 (m, 2H, H3', OH), 2.29-2.11 (m, 2H, H2'), 2.02-1.89 (m, 2H, H5') ppm.

5-iodo-5'-amino-2',5'-dideoxyuridine

Triphenylphosphine (1.68 g, 6.41 mmol) and 5-iodo-5'-azido-2',5'-dideoxyuridine (1.52 g, 4.01 mmol) were stirred in dried pyridine (25 mL) at room temperature for 1 h. Concentrated ammonium hydroxide (3 mL) was added and the stirring continued for the next 2 h. The solvent was evaporated under reduced pressure at 35° C. The residue was treated with 1N ammonium hydroxide (100 mL) and briefly sonicated, then extracted with diethyl ether (3×60 mL) and filtered, to remove the excess of unreacted triphenylphosphine and triphenylphosphine oxide. The extracts were filtered again and evaporated to dryness in a vacuum at 30° C. The solid residue was extracted with hot ethanol (3×50 mL), cooled, sonicated and a formed solid was collected by filtration, washed with ethanol/diethyl ether (1/1) and dried, to afford 0.72 g (51%) of a pure product (98.8% pure by HPLC analysis at 280 nm). mp 200-203° C. dec. $^1$H NMR (DMSO-d$_6$, 500 MHz) δ 11.42 (s, 1H, NH), 7.81 (s, 1H, H6-uridine), 6.04 (t, H1', $^3J_{1',2'}$=6.40 Hz), 5.44 (bs, 2H, NH$_2$), 4.02-3.85 (m, 1H, H4'), 3.62-3.56 (m, 2H, H3', OH), 3.11-2.74 (m, 2H, H5', H5"), 2.32-2.18 (m, 2H, H2') ppm.

To a stirred solution of the 5-iodo-5'-amino-2',5'-dideoxyuridine (1.91 g, 5.39 mmol) in 30 mL of dioxane/water (12:1), N,N'-bis(tert-butyloxycarbonyl)-N"-trifluoromethane-sulfonyl guanidine (2.11 g, 5.39 mmol) was added, followed by TEA (750 μL, 5.4 mmol). The stirring continued for 6 h, dioxane was evaporated, water (60 mL) added, and the mixture extracted with DCM (2×40 mL). The organic phase was washed with brine, then dried over MgSO$_4$, and evaporated. The residue of a crude product was purified on a silica gel column (DCM/MeOH, 10:0.4), followed by a second silica gel purification (EtOAc/n-hexanes, 2:1) to yield (6) (2.57 g, 79%) as colorless foam. HPLC analysis: 1) $t_R$=19.89 min (98.2% pure at 254 nm) on Columbus C8 column, eluted at the rate of 0.8 mL/min, with 45% MeCN in water for 30 min and then with a linear gradient of MeCN from 45 to 95% over 30 min. 2) $t_R$=34.56 min, (98.2% pure at 280 nm) on ACE C18 100 Å, (5 μm, 4.6×250 mm) column eluted at the rate of 0.8 mL/min with a linear gradient of MeCN in water from 10 to 95% over 35 min, then 95% MeCN for 25 min. $^1$H NMR (CDCl$_3$, 500 MHz) δ: 11.40 (s, 1H, NH-uridine), 9.13 (bs, 1H, NH), 8.07 (t, 1H, NH, J=5.85 Hz), 7.81 (s, 1H, H6-uridine), 6.08 (dd, 1H, H1', $^3J_{1',2'}$=6.4 Hz, $^3J_{1',2''}$=4.8 Hz), 4.31-4.25 (m, 2H, H3', C3'-OH), 3.78-3.73 (m, 2H, H4', H5'), 3.63-3.59 (m, 1H, H5"), 2.24-2.18 (m, 1H, H2'), 2.13-2.06 (m, 1H, H2"), 1.51 (s, 9H, 3×CH$_3$—BocN'), 1.47 (s, 9H, 3×CH$_3$—BocN") ppm. $^{13}$C NMR (CDCl$_3$, 100 MHz) δ: 162.44 (C4), 159.79 (C1-Boc-N'), 157.69 (C1-Boc-N"), 152.96 (C2), 149.66 (C-guanidine), 144.18 (C6), 118.28 (C5), 84.68 (C1'), 84.29 (C4',), 77.25 (C2-Boc-N'), 77.01 (C2-Boc-N"), 73.54 (C3'), 67.05 (C5'), 38.92 (C2'), 28.15 (C3-Boc-N'), 28.11 (C3-Boc-N") ppm.

Method B:

The 5'-hydroxyl group of 2'-dexyuridine was tosylated, the product was treated with lithium azide and obtained 5'-azido-2',5'-dideoxyuridine hydrogenated, to afford 5'-amino-2',5'-dideoxyuridine, which was later reacted with mercuric acetate, and a crude 5-mercuriacetate of 5'-amino-2',5'-dideoxyuridine was iodinated with elemental iodine in ethanol. The relevant preparations were carried out as follows:

5'-Azido-2',5'-dideoxyuridine

A mixture of 5'-O-p-tolylsulfonyl-2'-deoxyuridine (3.21 g, 8.40 mmol) and sodium azide (1.40 g, 21.5 mmol) in 50 mL of DMF was stirred at 90° C. for 3 h. After the cooling and filtration, the solvent was evaporated under reduced pressure at 40° C., and the residue of a crude product was purified on a silica gel column (DCM/MeOH, 10:1.1) to yield a white solid (1.92 g, 90%). Recrystallization from EtOH/H$_2$O produced white crystals: mp 140-141° C., 95.8% pure by HPLC analysis at 280 nm. $^1$H NMR (DMSO-d$_6$, 500 MHz) δ 11.04 (s, 1H, NH), 8.92 (d, 1H, H6-uridine, J=5.52 Hz), 6.12-5.96 (m, 2H, H1', H5-uridine), 4.12-3.91 (m, 1H, H4'), 3.66-3.57 (m, 2H, H3', OH), 2.37-2.16 (m, 2H, H2'), 1.91-1.54 (m, 2H, H5', H5") ppm.

5'-Amino-2',5'-dideoxyuridine

A solution of 5'-azido-2',5'-dideoxyuridine (2.1 g, 8.3 mmol) in EtOH/H2O (1/1) mixture was hydrogenated (30 psi) in the presence of palladium catalyst (0.2 g, 10% Pd/C) at room temperature for 2 h. The catalyst was filtered off and the solvent evaporated under reduced pressure to give 1.81 g (96%) of a product as a solid residue, which was recrystallized from EtOH: mp 190-192° C., 98.8% pure by HPLC analysis at 280 nm. $^1$H NMR (DMSO-d$_6$, 500 MHz) δ 10.62 (s, 1H, NH), 9.32 (d, 1H, H6-uridine, J=5.50 Hz), 6.11-5.88 (m, 2H, H1', H5-uridine), 4.05-3.86 (m, 1H, H4'), 3.77-3.55 (m, 2H, H3', OH), 2.91-2.64 (m, 2H, H5', H5"), 2.37-2.16 (m, 2H, H2') ppm.

5-iodo-5'-amino-2',5'-dideoxyuridine

To a solution of 5'-Amino-2',5'-dideoxyuridine (1.48 g, 6.51 mmol) in 115 mL of 0.5M acetate buffer (pH 6.0), mercuric acetate (5.50 g, 17.25 mmol) was added, and the mixture was stirred at ~55° C. for 20 h. The mixture was diluted with water (150 mL), cooled to room temperature, a solution of iodine (4.65 g, 18.3 mmol) in ethanol (62 mL) was added, and the stirring continued for 2 h. The mixture was extracted with DCM (5×60 mL), a volume of the aqueous phase reduced (~100 mL), and it was applied on a ion exchange resin column (2×30 cm, Dowex 50 H$^+$), first eluted with water (200 mL), and the product was washed out with 1N NH$_4$OH (120 mL). The product, which crystallized during the solvent evaporation, was filtered off (1.31 g, 79% yield) and recrystallized from EtOH/water. The analytical data of this product were identical with records reported for a product obtained in Method A.

5-Trimethylstannyl-5'-N—[N',N"-bis(tert-butyloxycarbonyl)guanidino]-2',5'-dideoxyuridine (7)

General Procedure B was carried out twice with 520 mg, 0.873 mmol and 712 mg, 1.196 mmol of 5-Iodo-5'-N—[(N', N"-bis-Boc)-guanidinyl]-2',5'-dideoxyuridine (6) in EtOAc, containing: hexamethylditin 486 mg (1.48 mmol) and 670 mg (2.05 mmol) respectively, TEA (300 μL, 2.15 mmol), and the palladium catalyst (30 mg, 0.043 mmol), to give (7) (680 mg) in 52% average yield. The final HPLC purification (160 mg, ~11 mg per injection) was done on a semi preparative Columbus C18, 100 Å (10×250 mm) column, eluted at 2.2 mL/min with 55% MeCN in water for 20 min, then a linear gradient of MeCN from 55-95% over 15 min and 95% MeCN kept further 30 min. HPLC analysis: 1) t$_R$=30.02 min (97.3% pure at 280 nm) on ACE C18 100 Å, (5 μm, 4.6×250 mm) column, eluted at 0.8 mL/min with 50% MeCN in water for a 20 min, then with a linear gradient from 50-95% of MeCN over 15 min and 95% MeCN continued for next 30 min. 2) t$_R$=47.06 min (98.4% pure at 280 nm), using the same column and the elution rate; eluent: solvent A water, solvent B CH$_3$CN; 45% B for 30 min, then a linear gradient of B to 95% over 30 min, continued for 30 min. $^1$H NMR (CDCl$_3$, 500 MHz) δ: 10.62 (bs, 1H, NH-uridine), 9.05 (bs, 1H, NH), 8.31 (t, 1H, NH, J=5.72 Hz), 7.49 (s, 1H, H6-uridine, $^3$J$_{Sn,H}$=19.5 Hz), 5.98 (dd, 1H, H1', $^3$J$_{1',2'}$=6.2 Hz, $^3$J$_{1',2"}$=4.6 Hz), 4.21-4.15 (m, 1H, H4'), 3.78-3.73 (m, 2H, H3',OH3'), 3.63-3.59 (m, 1H, H5"), 2.34-2.28 (m, 1H, H2'), 2.19-2.04 (m, 1H, H2"), 1.44 (s, 9H, 3×CH$_3$-t-Bu), 1.41 (s, 9H, 3×CH$_3$-t-Bu), 0.32 (s, 9H, 3×CH$_3$, $^2$J$_{Sn,H}$=29.5 Hz) ppm. $^{13}$C NMR (CDCl$_3$, 100 MHz) δ: 165.64 (C4), 160.46 (C-guanidine), 158.39 (C1-Boc-N'), 156.16 (C1-Boc-N"), 150.86 (C2), 143.38 (C6), 112.73 (C5), 86.79 (C1'), 85.19 (C4',), 79.75 (C2-Boc-N'), 75.31 (C2-Boc-N"), 71.64 (C3'), 67.05 (C5'), 38.92 (C2'), 28.15 (C3-Boc-N'), 28.11 (C3-Boc-N"), −7.15 (3×CH$_3$—Sn) ppm. $^{119}$Sn NMR (CDCl$_3$, 100 MHz) δ=−1.47 ppm.

5-[$^{125}$I]-iodo-5'-N—[N',N"-bis(tert-butyloxycarbonyl)guanidino]-2',5'-dideoxyuridine (8)

A total of four radioiodinations were carried out according to General Procedure C, with ~100 μg of stannane (7) and Na$^{125}$I/NaOH, within the 18.5-77.7 MBq range, to give overall 140.6 MBq of (8). An average yield of the purified product was 84%. The HPLC purification of a crude reaction mixture proceeded on ACE C8 100 Å (5 μm, 4.6×250 mm), eluted at 0.8 mL/min initially with 45% MeCN in water for 30 min, then with a linear gradient of MeCN from 45 to 95% MeCN over 30 min, and 95% MeCN was held for 15 min longer. The product (8) eluted within 19.5-22.0 min after the injection and was collected in three fractions. An excess of unreacted stannane (7), eluting between 46.5-49.0 min, was completely separated from the product. Two HPLC co-injections of purified (8) and nonradioactive analog (6) (Bioscan NaI(T) detector and UV signal at 220/280 nm) confirmed the same mobility of both compounds: 1) t$_R$=20.1 min, ACE C8 100 Å (5 μm, 4.6×250 mm), eluted at 0.8 mL/min at first with 45% MeCN in water for 30 min, then a linear gradient of MeCN from 45 to 95% MeCN over 30 min and kept at 95% MeCN for 15 min. 2) t$_R$=37.4 min, ACE C18 100 Å (5 μm, 4.6×250 mm), eluted at 0.8 mL/min of the eluant: a linear gradient of MeCN in water from 5 to 95% over 60 min, then kept at 95% MeCN for 30 min.

5-[$^{125}$I]-Iodo-5'-N-guanidino-2',5'-dideoxyuridine (9)

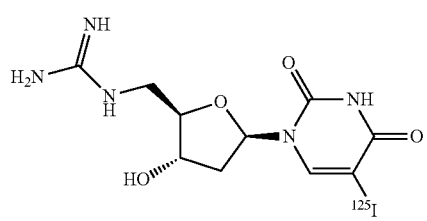

[9]

Figure 2:
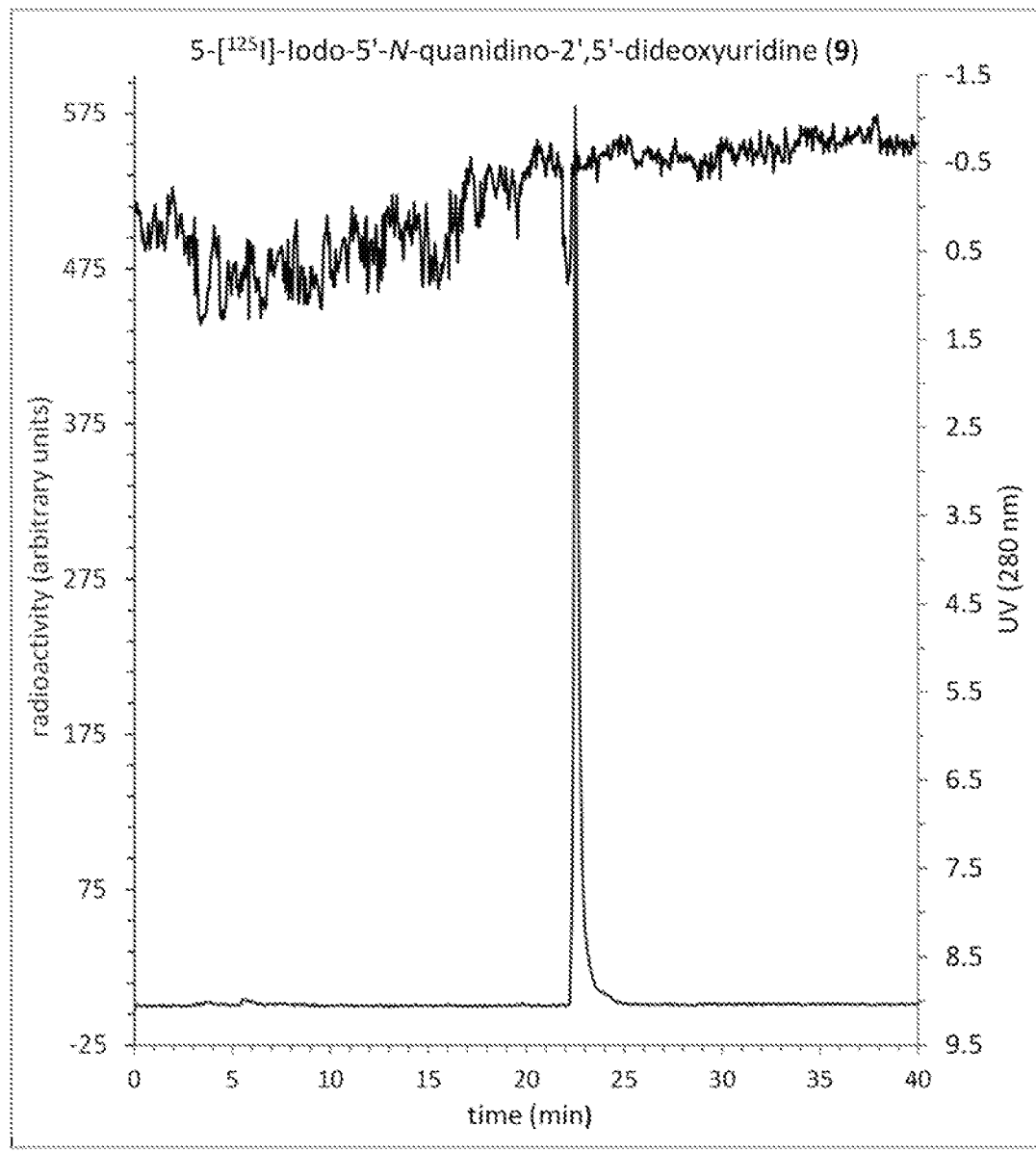
FIG. 2 is a graph showing the results of an HPLC analysis of purified 5-[$^{125}$I]-Iodo-5'-N-guanidino-2',5'-dideoxyuridine (9)
Figures 3A, 3B:
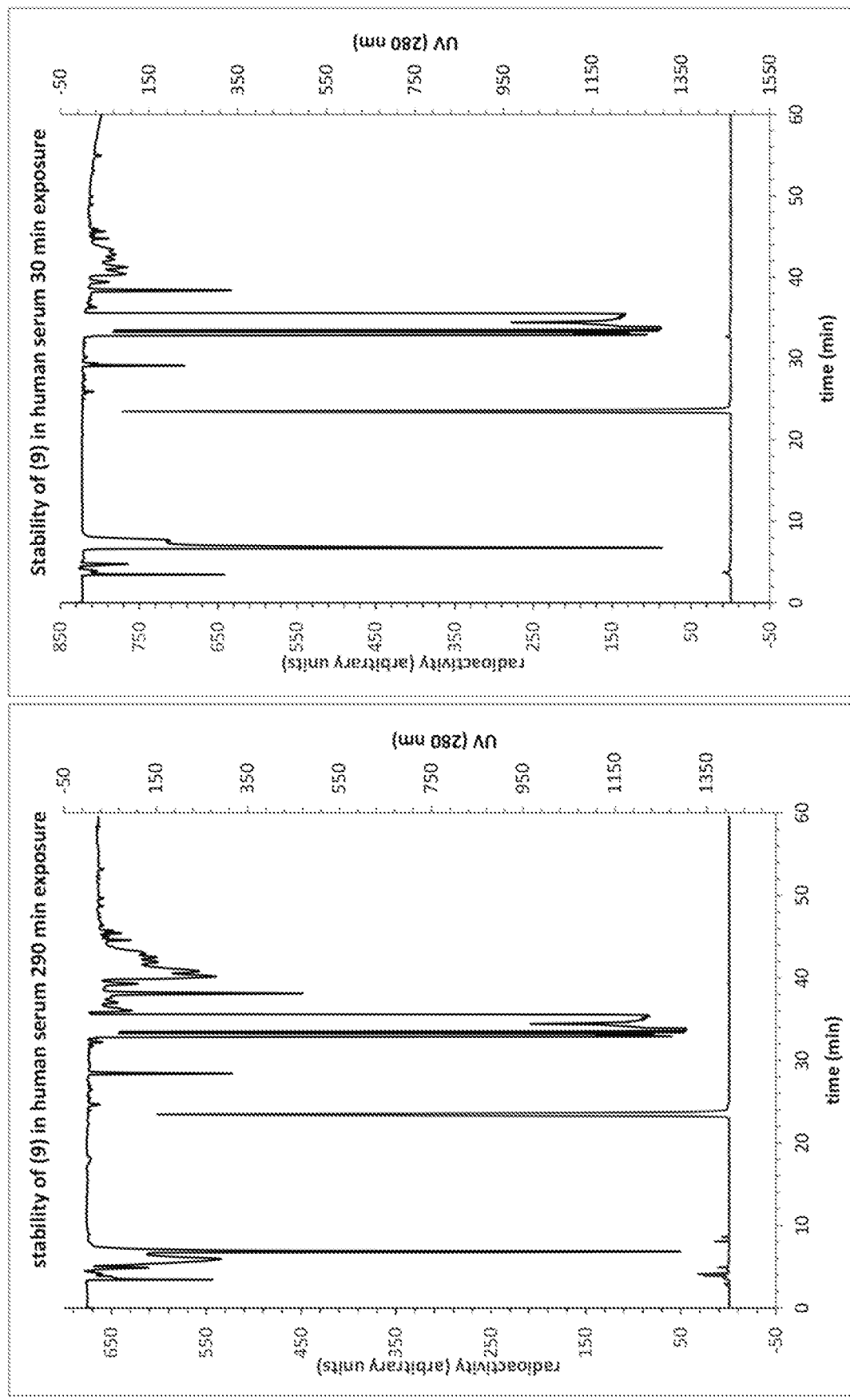
FIG. 3A is a graph showing HPLC analysis of 5-[$^{125}$I]-Iodo-5'-N-guanidino-2',5'-dideoxyuridine (9) in human serum at 290 minutes of incubation.
FIG. 3B is a graph showing HPLC analysis of 5-[$^{125}$I]-Iodo-5'-N-guanidino-2',5'-dideoxyuridine (9) in human serum at 30 minutes of exposure.
Figures 3C, 3D:
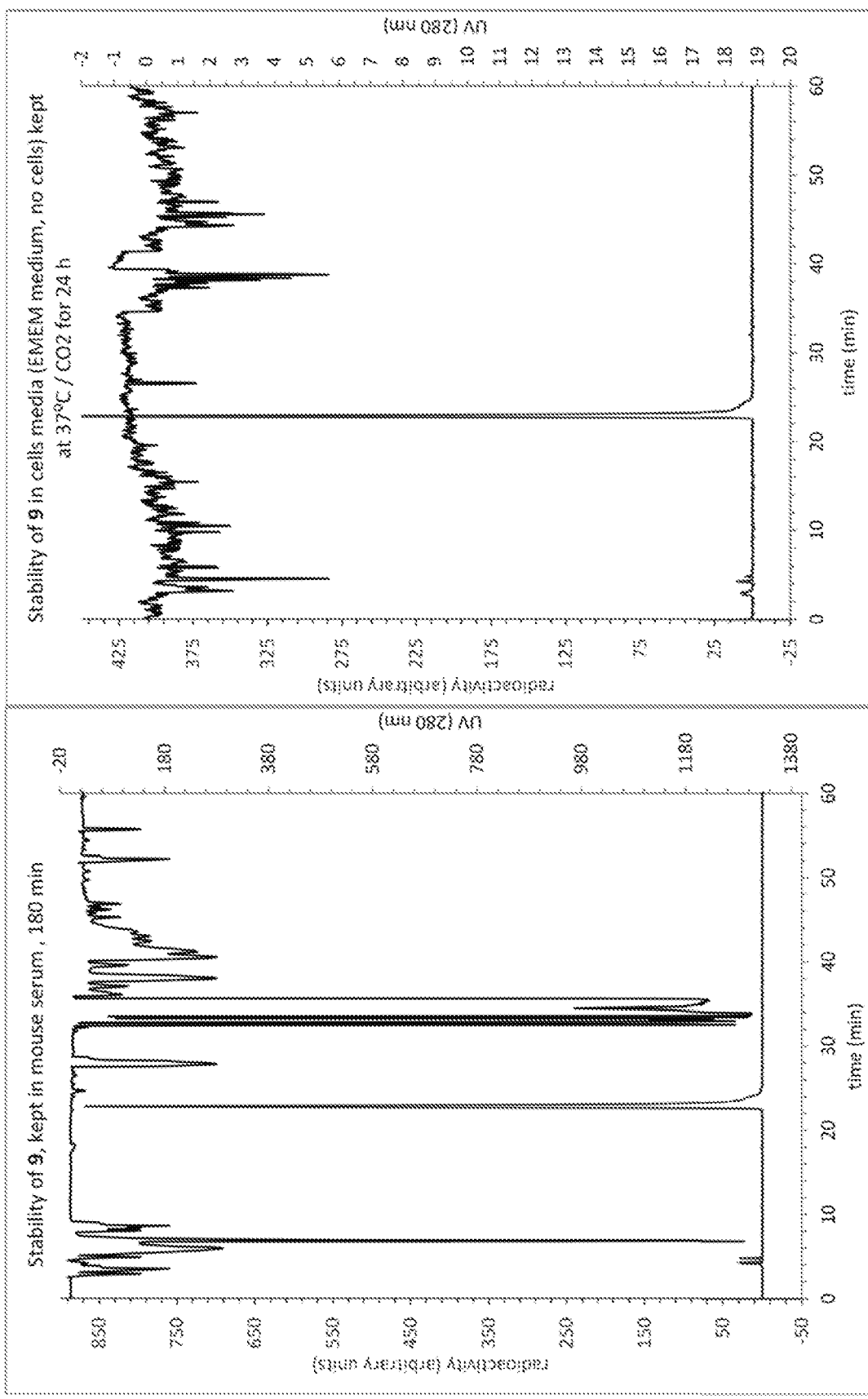
FIG. 3C is a graph showing HPLC analysis of 5-[$^{125}$I]-Iodo-5'-N-guanidino-2',5'-dideoxyuridine (9) in mouse serum at 180 minutes of exposure.
FIG. 3D is a graph showing HPLC analysis of 5-[$^{125}$I]-Iodo-5'-N-guanidino-2',5'-dideoxyuridine (9) in cells media kept at 37° C./CO$_2$ for 24 hours.
Figures 4A, 4B:
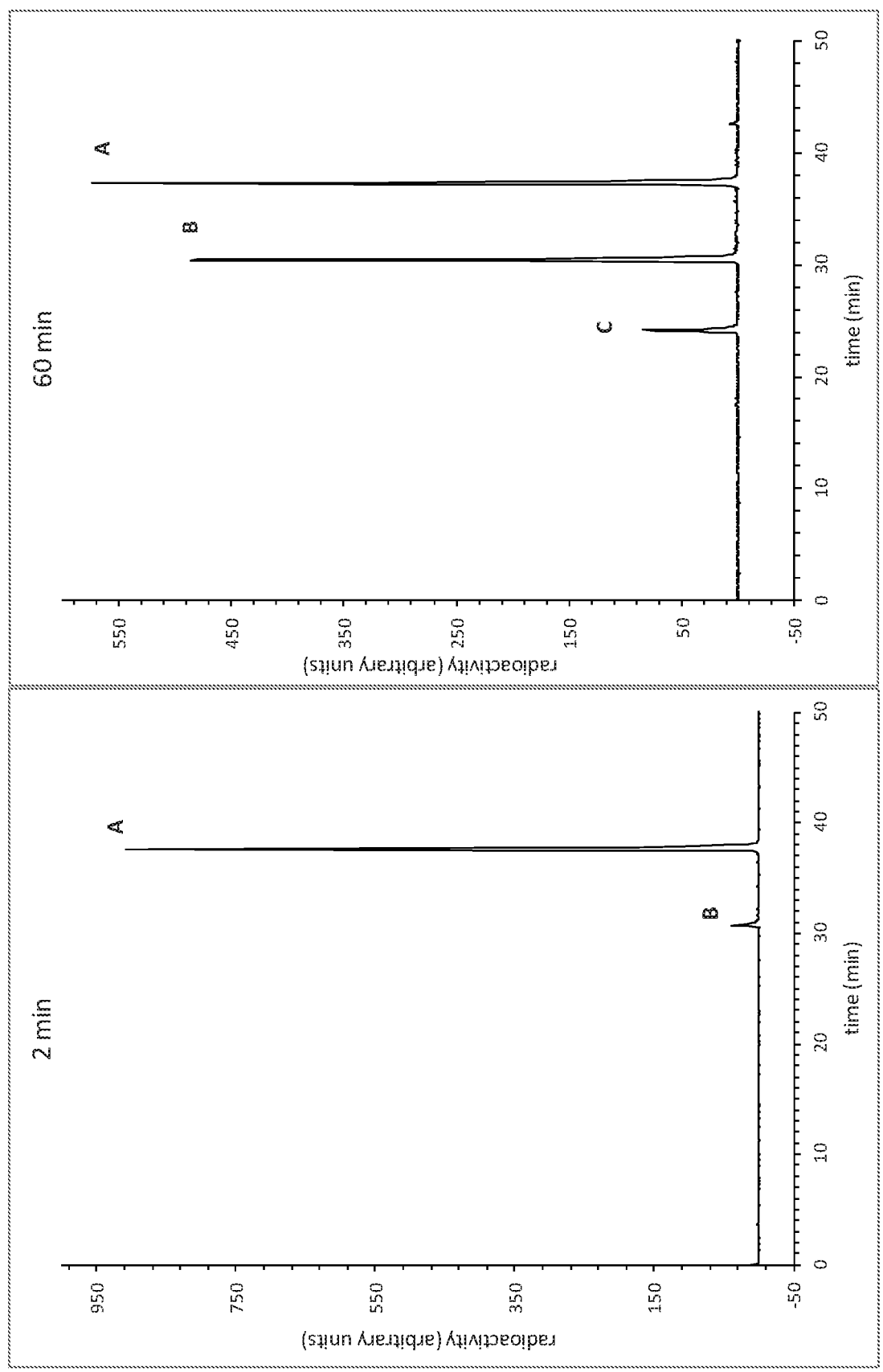
FIG. 4A is a graph showing HPLC analysis of deprotection of 5-[$^{125}$I]-Iodo-3'-O—[(N,N'-bis(tert-butyloxycarbonyl)-N''-hexanoyl)guanidino]-2'-deoxyuridine (12) at room temperature at 2 minutes.
FIG. 4B is a graph showing HPLC analysis of deprotection of 5-[$^{125}$I]-Iodo-3'-O—[(N,N'-bis(tert-butyloxycarbonyl)-N''-hexanoyl)guanidino]-2'-deoxyuridine (12) at room temperature at 60 minutes.
Figures 4C, 4D:
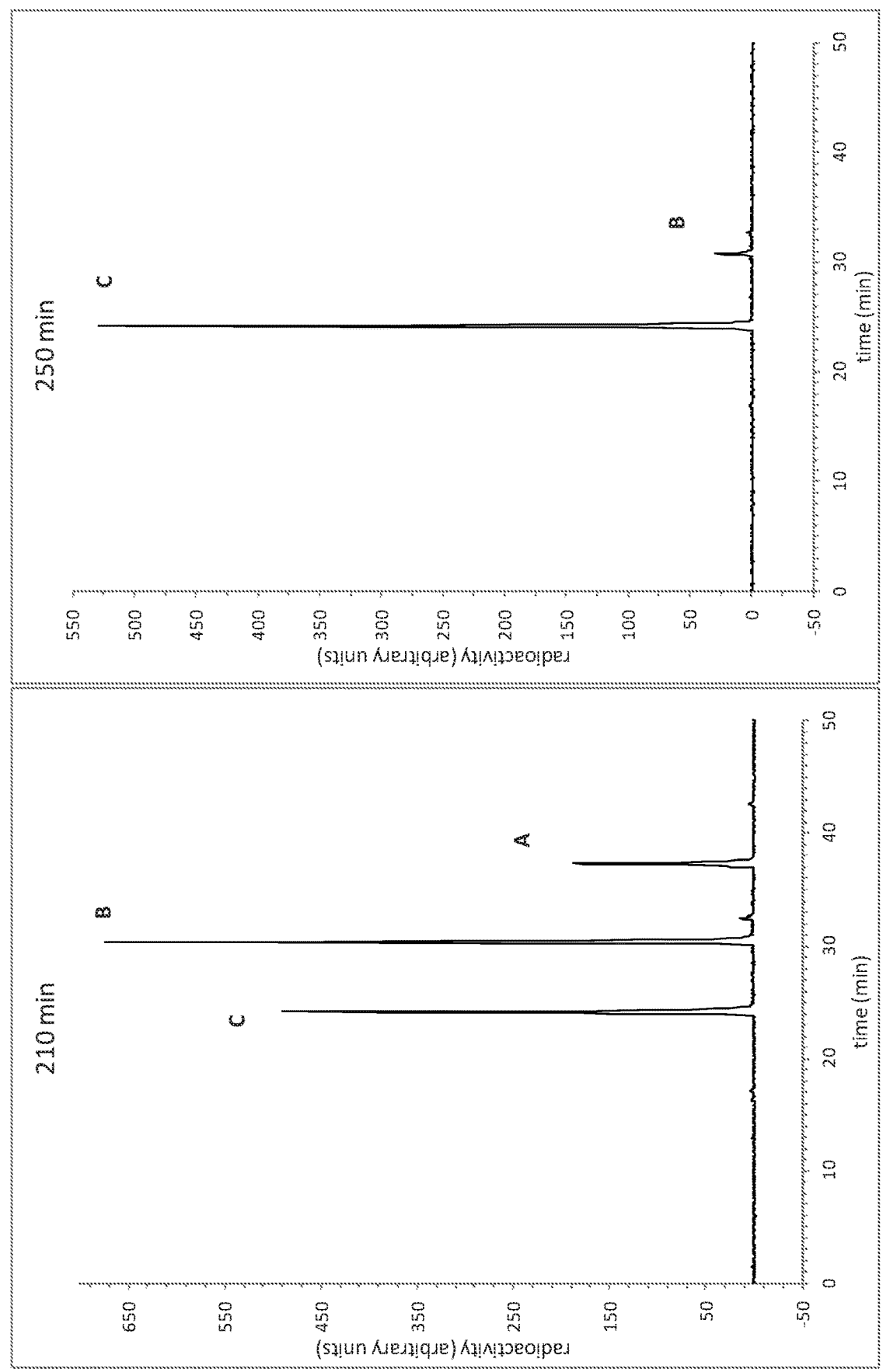
FIG. 4C is a graph showing HPLC analysis of deprotection of 5-[$^{125}$I]-Iodo-3'-O—[(N,N'-bis(tert-butyloxycarbonyl)-N''-hexanoyl)guanidino]-2'-deoxyuridine (12) at room temperature at 210 minutes.
FIG. 4D is a graph showing HPLC analysis of deprotection of 5-[$^{125}$I]-Iodo-3'-O—[(N,N'-bis(tert-butyloxycarbonyl)-N''-hexanoyl)guanidino]-2'-deoxyuridine (12) at room temperature at 250 minutes.

Applying General Procedure C, the crude radioiodination reaction mixture of (7), or dried residue of purified (8) was treated with TFA (neat) and kept at 75° C. for 15 min, to completely cleave Boc-protection of guanidine. The deprotection progress (removal of Boc protecting groups) of (8), using a solution of 40% TFA in MeCN, was monitored by HPLC at room temperature and was completed within 70 min. Progress of deprotection was also monitored on HPLC (Bioscan NaI(T) detector), using ACE C18 100 Å (5 μm, 4.6×250 mm) column, eluted at 0.8 mL/min with 5% MeCN in water for 10 min, followed by a linear gradient of MeCN from 5 to 95% MeCN over 30 min and held for 15 min, wherein both solvents contained 0.07% TFA (v/v). An average yield of the purified (9) was 91%. The product ($t_R$=10.4 min, ≥98% radiochemical purity, Bioscan NI(T)/UV 280 nm) eluting within 9.5-12.0 min after injection was collected in three fractions, which were combined, evaporated, and added to the tube containing the product residue 80 μL of ethanol, followed by potassium phosphate buffer (100 μL, 100 mM PB, pH 6.1). The resulting solution of (9) was injected again on an HPLC system equipped with Luna CN (5μ, 4.5×250 mm) and a reverse phase column eluted at 0.8 mL/min with the two consecutive gradients of EtOH in potassium phosphate buffer (100 mM PB, pH 6.1): 0 to 5% in 10 min; and 10 to 60% over the next 30 min. The product was collected within 21.5-23.0 min after the injection. HPLC analysis: $t_R$=22.5 min (≥98% radiochemical purity, Bioscan NI(T)), as shown in FIG. 2.

Stability Evaluation of 5-[$^{125}$I]-Iodo-5'-N-guanidino-2',5'-dideoxyuridine (9)

Incubations: into a solution (1980 μL) of serum (mouse, human) or cells media, a sample of (9), (370-740 kBq) in 20 μL of 25% EtOH/PB (100 mM, pH 6.1) was added; the resulting mixture was briefly vortexed and kept (up to 6 h) at ambient temperature. At each time point, a volume of 1 mL was withdrawn and analyzed by HPLC.

Preparation of samples: a sample (1 mL) from each incubated mixture with compound (9) was treated with MeCN (1 mL), vortexed, and centrifuged (2,000 rpm, 15 min). Aliquots of supernatant (500 μL) were acidified to pH~6 with 0.05 N TFA (2-8 μL). The excess of MeCN was evaporated with a stream of nitrogen and water (100 μL) added. A mixture was passed through a 0.2μ filter and each sample (~100 μL, 62.5-130 kBq) injected on HPLC system.

HPLC analysis of incubated mixtures: proceeded on Luna CN (5μ, 4.5×250 mm) column; eluent: solvent A potassium phosphate buffer (100 mM, pH 6.1), solvent B EtOH; all samples were eluted at 0.8 mL/min, initially with a gradient of EtOH from 0 to 5% for 10 min, then from 5 to 60% over next 30 min, detecting the radioactivity (Bioscan NaI(T)) and UV 280 nm. The HPLC results are shown in FIGS. 3A-3D.

Preparation of 5-Iodo-3'-O—[N,N'-bis(tert-(butyloxycarbonyl)-N"-hexanoyl)-guanidino]-2'-deoxyuridine (10)

In the preparation of (10), starting 5-Iodo-2'-deoxyuridine (1) (IUdR) was initially 5'-O-silylated with TBDMSCl in pyridine, to yield 5-iodo-5'-O-tert-butyldimethylsilyl-2'-deoxyuridine (4) (5'-TBDMS-IUdR) in 79% yield. After that, (4) was reacted with 6-N-Boc-aminohexanoic acid (using DCC/DMPA activation), and the product was directly desilylated with 2% TBAF in THF to furnish 5-iodo-3'-O-(6-N-Boc-aminohexanoyl)-2'-deoxyuridine, which after removal of the N-Boc amino protecting group in 20% TFA/MeCN and subsequent guanidinylation of the free amino group with N,N'-Bis(tert-butyloxycarbonyl)-N"-trifluoromethanesulfonyl guanidine (as described below), led to the guanidinoalkyl ester (10) in 67% yield.

5-Iodo-5'-O-tert-butyldimethylsilyl-2'-deoxyuridine (4)

A mixture of IUdR (2.54 g, 7.17 mmol) and TBDMSCl (1.35 g, 8.97 mmol) in 25 mL of pyridine was stirred at room temperature overnight. Methanol (2 mL) was added and the solvent removed under reduced pressure. The residue was dissolved in DCM (30 mL), washed with water, dried over MgSO$_4$, filtered, and the solution evaporated. A crude product was purified by column chromatography on a silica gel with a gradient of MeOH in DCM (0.3-0.7:10) to give 2.65 g (79% yield) of compound (4); $R_f$ value 0.54 (DCM/MeOH, 10:0.5). $^1$H NMR (DMSO-d$_6$, 500 MHz) δ 11.57 (s, 1H, NH), 7.78 (s, 1H, H6-uridine), 6.07 (dd, H1', $^3J_{1',2'}$=5.45 Hz, $^3J_{1',2''}$=4.45 Hz), 5.32 (d, 1H, OH), 3.83-3.74 (m, 1H, H3'), 3.72-3.64 (m, 4H, H4', H5'), 2.24-2.12 (m, 2H, H2'), 0.91 (s, 9H, H3-TBDMS), 0.17 (s, 6H, H1-TBDMS) ppm. $^{13}$C NMR (DMSO-d$_6$, 100 MHz) δ: 162.82 (C4), 158.75 152.26 (C2), 140.18 (C6), 109.37 (C5), 86.49 (C1'), 84.24 (C4'), 73.37 (C3'), 64.47 (C5'), 39.52 (C2'), 29.06 (C3-TBDMS), 25.11 (C2-TBDMS), −5.02 (C1-TBDMS) ppm.

5-Iodo-3'-O-(6-N-Boc-aminohexanoyl)-2'-deoxyuridine

To a solution of TBDMS-IUdR (4) (2.52 g, 5.38 mmol), 6-N-Boc-aminohexanoic acid (1.31 g, 5.66 mmol), and DMAP (0.173 g, 1.42 mmol) in 25 mL of DCM, dicyclohexylcarbodiimide (1.17 g 5.65 mmol) was added at room temperature. The reaction mixture was stirred for 3 h (TLC monitoring), filtered, and the solvent removed under reduced pressure. The residue was purified by column chromatography on a silica gel, using a gradient of MeOH in DCM (0.3-0.5:10). Fractions containing a product were combined, evaporated, and to a residue dissolved in THF (15 mL), a solution of tetrabutylammonium fluoride (1M, 0.5 mL) in THF was added. The mixture was then stirred for 5 h at room temperature, the solvent evaporated under reduced pressure, and the reaction mixture purified by column chromatography on a silica gel with a gradient of MeOH in DCM (0.5-0.7:10) to give 1.95 g (64% yield) of the title compound; $R_f$ value 0.43 (DCM/MeOH, 10:0.5). $^1$H NMR (DMSO-d$_6$, 500 MHz) δ 11.64 (s, 1H, NH), 8.09 (s, 1H, H6-uridine), 7.85 (bd, 1H, NH-Boc, J=4.7 Hz), 6.18 (dd, H1', $^3J_{1',2'}$=6.45 Hz, $^3J_{1',2''}$=4.40 Hz), 5.35-5.18 (m, 2H, H3',OH), 3.86-3.74 (m, 4H, H4', H5"), 3.19-3.12 (2H, H6-Hex), 2.34-2.27 (m, 2H, H2'), 2.20-2.12 (2H, H2-Hex), 1.85-1.64 (2H, H3-Hex), 1.57-1.51 (2H, H5-Hex), 1.38 (s, 9H, H3-Boc), 1.33-1.28 (2H, H4-Hex) ppm. $^{13}$C NMR (DMSO-d$_6$, 100 MHz) δ: 172.85 (C1-Hex), 161.86 (C4), 155.56 (C1-Boc-N), 150.16 (C2), 140.38 (C6), 110.16 (C5), 84.59 (C1'), 83.74 (C4'), 79.46 (C2-Boc), 74.87 (C3'), 62.27 (C5'), 40.47 (C6-Hex), 34.64 (C2-hex), 38.72 (C2'), 29.63 (C5-Hex), 28.47 (C3-Boc), 26.19 (C4-Hex), 24.27 (C3-Hex) ppm.

General Procedure A was carried out with the 5-iodo-3'-O-(6-N-Boc-aminohexanoyl)-2'-deoxyuridine (1.12 g, 1.97 mmol), the Boc protecting group was cleaved, and the separated TFA salt reacted immediately with 0.82 g (2.10 mmol) of N,N'-bis(tert-butoxycarbonyl)-N"-trifluoromethanesulfonyl guanidine. A residue of the crude product was purified by chromatography on a silica gel column using a gradient of MeOH in DCM (10:0.3-0.5) to give 938 mg of (10) in 67% yield. $R_f$ value 0.42 (DCM/MeOH, 10:0.4).

HPLC Analysis of 5-Iodo-3'-O—[N,N'-bis(tert-(butyloxycarbonyl)-N"-hexanoyl)-guanidino]-2'-deoxyuridine (10)

HPLC analysis: $t_R$=29.9 min (≥96.6% pure at 280 nm) on ACE C18 100 Å, (5 μm, 4.6×250 mm) column, at the elution rate of 0.8 mL/min with a linear gradient of MeCN in water from 40 to 95% over 45 min, then 95% MeCN kept for 15 min. $^1$H NMR (DMSO-$d_6$, 500 MHz) δ: 11.61 (s, 1H, NH-uridine), 8.32 (bs, 1H, NH), 8.16 (t, 1H, NH, J=5.52 Hz), 8.06 (s, 1H, H6-uridine), 6.28 (dd, 1H, H1', $^3J_{1',2'}$=6.40 Hz, $^3J_{1',2''}$=4.85 Hz), 5.15-4.87 (m, 2H, H3', OH), 4.19-4.02 (m, 1H' H4'), 3.77-3.56 (m, 4H, H5', H2-Ac), 2.89-2.76 (m, 2H, H6-Hex)' 2.58-2.46 (m, 1H, H2'), 2.38-2.29 (m, 1H, H2"), 1.72-1.64 (m, 2H, H3-Hex), 1.61-1.54 (m, 2H, H5-Hex), 1.52 (s, 9H, H3-BocN'), 1.46 (s, 9H, H3-BocN"), 1.36-1.29 (m, 2H, H4-Hex) ppm. $^{13}$C NMR (DMSO-$d_6$, 100 MHz) δ: 172.75 (C1-Hex), 162.82 (C4), 158.75 (C1-Boc-N'), 156.66 (C1-Boc-N"), 153.46 (C2), 149.52 (C-guanidine), 142.48 (C6), 110.27 (C5), 85.19 (C1'), 84.44 (C4'), 80.83 (C2-Boc-N'), 79.72 (C2-Boc-N"), 74.67 (C3'), 61.41 (C5'), 41.34 (C2-hex), 40.47 (C6-Hex), 37.74 (C2'), 31.81 (C5-Hex), 28.38 (C3-Boc-N'), 28.33 (C3-Boc-N"), 26.51 (C4-Hex), 24.73 (C3-Hex) ppm.

HPLC analysis: $t_R$=45.5 min 98.2% pure at 254 nm) on Columbus C18 100 Å, (5 μm, 4.6×250 mm) column, at the elution rate of 0.8 mL/min with a linear gradient of MeCN in water from 10 to 95% over 60 min, then 95% MeCN kept for 15 min.

HPLC Purification and Analysis of 5-Trimethylstannyl-3'-O—[(N,N'-bis(tert-(butyloxycarbonyl)-N"-hexanoyl) guanidino]-2'-deoxyuridine (11)

This compound was prepared twice according to General Procedure B and a crude product was purified by repeating a silica gel column chromatography and using a gradient of MeOH in DCM (0.3-0.5:10) to give (11) (89 mg and 136 mg) in 37% and 41% yield. $R_f$ value 0.47 (DCM/MeOH, 10:0.4). Specifically, stannylation of 5-Iodo-3'-O—[(N,N'-bis(tert-(butyloxycarbonyl)-N"-hexanoyl)guanidino]-2'-deoxyuridine was conducted two times, with 230 mg (0.324 mmol) and repeated with 316 mg (0.445 mmol) of (10), and hexamethylditin 160 mg (0.488 mmol) and 219 mg (0.668 mmol) respectively, in the presence of the palladium catalyst (25 mg, 0.036 mmol) and TEA (200 μL, ~1.4 mmol). A crude product was purified on a silica gel column using a gradient of MeOH in DCM (0.3-0.5:10) to give (11) (89 mg and 136 mg) in 37% and 41% yield accordingly. $R_f$ value 0.47 (DCM/MeOH, 10:0.4). HPLC analyses: $t_R$=36.8 min (95.91% pure at 220/280 nm) on ACE C18 100 Å, (5 μm, 4.6×250 mm) column, eluted at the rate of 0.8 mL/min with a linear gradient of MeCN in water, from 40 to 95% over 50 min, then 95% MeCN was kept for further 20 min. $^1$H NMR (DMSO-$d_6$, 500 MHz) δ: 11.66 (s, 1H, NH-uridine), 8.72 (bs, 1H, NH), 8.37 (t, 1H, NH, J=5.48 Hz), 7.76 (s, 1H, H6-uridine, $^3J_{Sn,H}$=19.2 Hz), 6.32 (dd, 1H, H1', $^3J_{1',2'}$=6.45 Hz, $^3J_{1',2''}$=4.80 Hz), 4.95-4.81 (m, 1H, H4'), 4.39-4.22 (m, 1H' H3'), 3.77-3.64 (m, 3H, H5',OH), 2.89-2.77 (m, 2H, H6-Hex), 2.59-2.42 (m, 3H, H2', H2-Hex), 2.38-2.29 (m, 1H, H2"), 1.70-1.63 (m, 2H, H3-Hex), 1.58-1.50 (m, 2H, H5-Hex), 1.41 (s, 9H, H3-BocN'), 1.37 (s, 9H, H3-BocN"), 1.30-1.27 (m, 2H, H4-Hex), 0.27 (s, 9H, 3×SnCH$_3$, $^2J_{Sn,H}$=29.2 Hz) ppm. $^{13}$C NMR (DMSO-$d_6$, 100 MHz) δ: 173.18 (C1-Hex), 163.37 (C4), 160.15 (C1-Boc-N'), 158.29 (C1-Boc-N"), 153.49 (C2), 149.57 (C-guanidine), 142.28 (C6), 110.22 (C5), 85.89 (C1'), 84.34 (C4'), 80.89 (C2-Boc-N'), 79.87 (C2-Boc-N"), 74.55 (C3'), 61.49 (C5'), 41.16 (C6-hex), 40.47 (C2-Hex), 37.74 (C2'), 31.87 (C5-Hex), 28.39 (C3-Boc-N'), 27.39 (C3-Boc-N"), 26.55 (C4-Hex), 24.73 (C3-Hex), −7.85 (3×CH$_3$—Sn) ppm. $^{119}$Sn NMR (CDCl$_3$, 100 MHz) δ=−1.67 ppm.

After a lengthy period of storage of stannane (11) (~six months) the successive HPLC purification was required, to allow for the immediate radioiododestannylation. Purification of (11) (12-15 mg per injection) was done on a semi preparative Columbus C18 column (10×250 mm) eluted at 2.3 mL/min with 40% MeCN in water for 30 min, then a linear gradient of MeCN 40-95% over 10 min and 95% MeCN kept for 30 min. Purified (11) was collected amid 24.5-26 min after the injection. HPLC analysis of purified stannane (11) used directly in the following radioiodinations: $t_R$=24.28 min (≥97.91% pure at 220/280 nm) on ACE C18 100 Å, (5 μm, 4.6×250 mm) column, eluent: solvent A water, solvent B CH$_3$CN; 40% B for 30 min, then a linear gradient of B from 40 to 95% over 10 min, then 95% B for 30 min, the rate of elution of 0.8 mL/min.

5-[$^{125}$I]-Iodo-3'-O—[(N,N'-bis(tert-(butyloxycarbonyl)-N"-hexanoyl)-guanidino]-2'-deoxyuridine (12)

Standard radioiodination (General Procedure C) of stannane (11) (~100 μg) was carried out two times, with 40.7 and 57.4 MBq of Na$^{125}$I/NaOH, to give overall 82 MBq of (12). An average yield of the isolated product was 85%. A crude reaction mixture was separated and purified by HPLC on Jupiter C18 100 Å (5 μm, 4.6×250 mm) column eluted at the rate of 0.8 mL/min, using a linear gradient of MeCN in water from 40 to 95% over 45 min., then 95% MeCN was held for further 25 min. The main radioactivity peak (33 MBq, 81%) was collected in three fractions (2.5 mL vol.) within 29.3-30.8 min after the injection (480 uL, 40.7 MBq) of the crude reaction mixture. An excess of unreacted tin precursor (11) was eluting between 35.9-36.8 min. was fully separated, from the product. HPLC analysis of separation of (12) from the reaction mixture: $t_R$=29.90 min, (≥98% radiochemical purity, Bioscan NI(T)/UV 280 nm).

Combined fractions containing the purified product (12) (33 MBq, 81% yield) were evaporated, reconstituted in MeCN (~3 MBq/mL) and a volume of 5 uL (277.5 kBq) was injected on the column, eluted at the rate of 0.8 mL/min, using a linear gradient of MeCN in water from 40 to 95% over 45 min, and then held at 95% for 15 min.

Elimination of Boc Protecting Groups of 5-[$^{125}$I]-Iodo-3'-O—[(N,N'-bis(tert-butyloxycarbonyl)-N"-hexanoyl)guanidino]-2'-deoxyuridine (12) at Room Temperature The deprotection of (12) (a solution of 962 kBq in 250 μL of 40% TFA/MeCN) was tested initially at room temperature. Cleavage of both Boc guanidine protecting groups was completed within ~250 min. The deprotection progress was monitored on HPLC (Bioscan NaI(T) detector), using ACE C18 100 Å (5 μm, 4.6×250 mm) column, eluted at 0.8 mL/min with a linear gradient of MeCN in water (0-95% over 50 min). Both solvents contained 0.07% TFA (v/v), 50 μL samples (~192 kBq) were injected periodically on the HPLC system. The deprotection (HPLC monitoring) of (12) to (13), in a solution of 40% TFA in MeCN at room temperature required 250 min. The results are shown in the graphs of FIG. 4A-4D, where A=5-[125I]-odo-3'-O—[(N,N'-bis(tert-(butyloxycarbonyl)-N"-hexanoyl)guanidino]-2'-deoxyuridine (12), B=5-[125I]-Iodo-3'-O—[N-(tert-(butyloxycarbonyl)-N'-hexanoyl)guanidino]-2'-deoxyuridine, and C=5[125I]-Iodo-3'-O—(N-hexanoylguanidino)-2'-deoxyuridine (13).

5-[$^{125}$I]-Iodo-3'-O-hexanoylguanidino-2'-deoxyuridine (13)

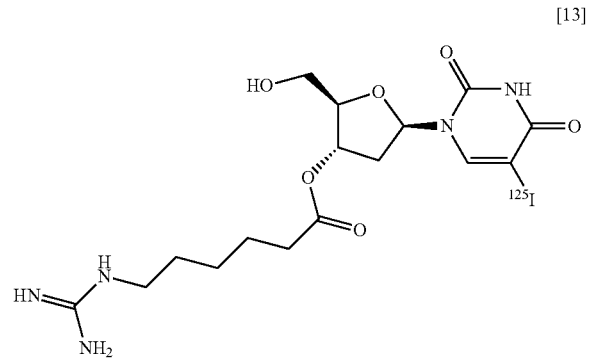 [SMILES: N=C(N)NCCCCCC(=O)O[C@H]1C[C@H](n2cc([125I])c(=O)[nH]c2=O)O[C@@H]1CO]

[13]

Figure 5:
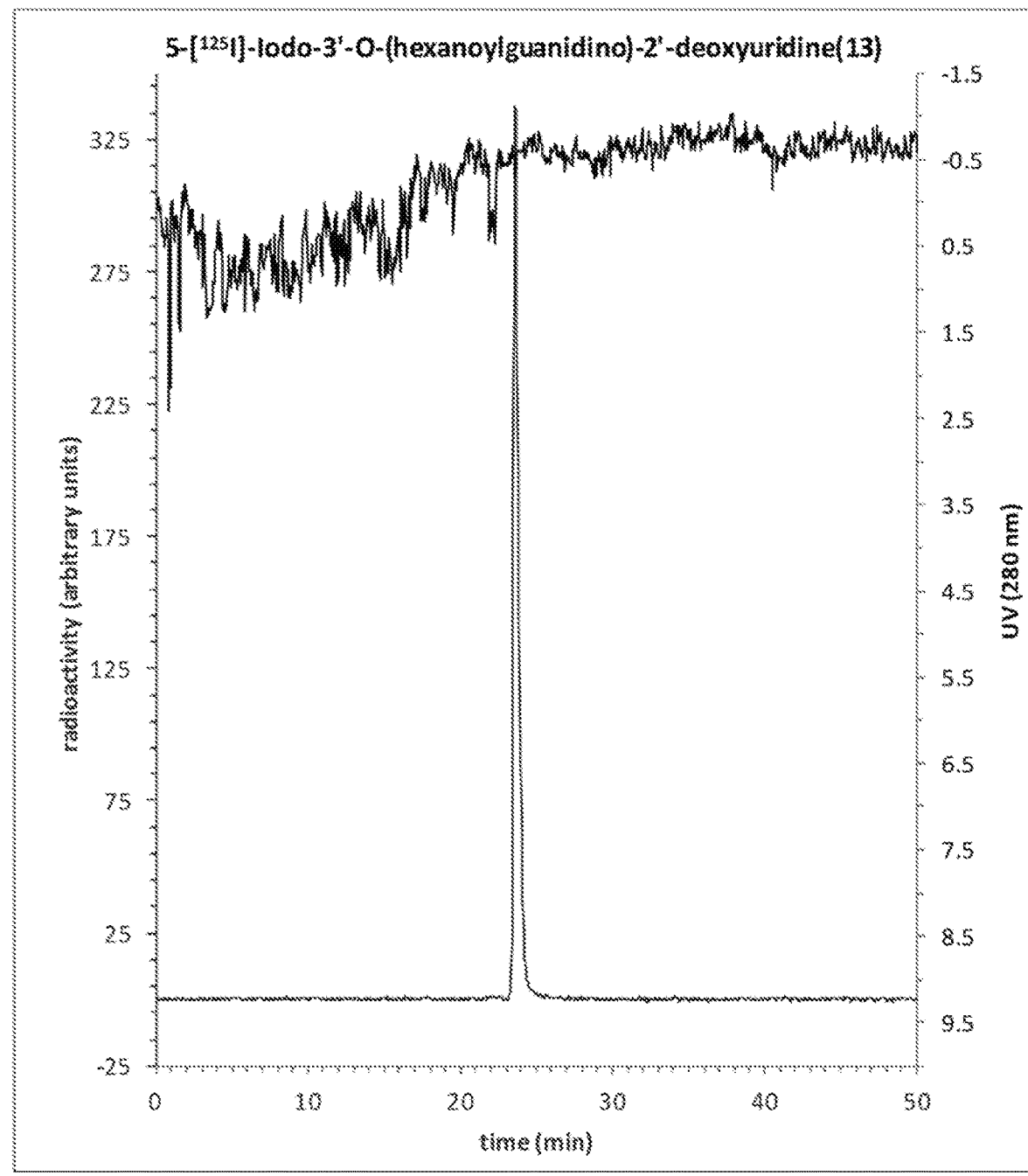
FIG. 5 is a graph showing the results of an HPLC analysis of purified 5-[$^{125}$I]-Iodo-3'-O-hexanoylguanidino-2'-deoxyuridine (13)

A treatment of (12) (dried residue, 21.8 MBq) with neat TFA (30 µL) at 75° C. accelerated the elimination of the guanidine Boc-protection and was completed in 20 min. An average yield (from four preparations) of the purified (13) was 89%. Product (19.37 MBq, first preparation) was separated on ACE C18 100 Å (5 µm, 4.6×250 mm) column, eluted at 0.8 mL/min with a linear gradient of MeCN from 0 to 95% over 50 min and 95% MeCN kept for an additional period of 20 min, both solvents contained 0.07% TFA (v/v); $t_R$ 23.67 min (≥98% radiochemical purity, Bioscan/UV 280 nm). The product eluting within 23.2-24.5 min after the injection was collected in three fractions, which were combined and evaporated. To eliminate the presence of TFA and MeCN in the sample, ethanol (80 µL) was added to a portion of the product residue (9.1 MBq), followed by potassium phosphate buffer (100 µL, 100 mM PB, pH 6.1). The resulting solution was injected again on HPLC system equipped with Luna CN (5, 4.5×250 mm) column and eluted at the rate of 0.8 mL/min with 15% EtOH in potassium phosphate buffer (100 mM PB, pH 6.1) for a period of 10 min, then with a linear gradient of 15 to 50% EtOH in PB over a 20 min period. The product (8.2 MBq, 90%) was collected within 19.3-22.5 min after the injection ($t_R$=19.9 min, ≥97% radiochemical purity Bioscan), as shown in FIG. 5.

Stability Assessment of 5-[$^{125}$I]-Iodo-3'-O-(hexanoylguanidino)-2'-deoxyuridine (13)

Incubations: into a solution (1980 µL) of serum (mouse, human), buffer or cells media, a sample of (13), (240.5-388.5 kBq) in 15-20 µL of 25% EtOH/PB (100 mM, pH 6.1) was added; the resulting mixture was briefly vortexed and kept (up to 24 h) at ambient temperature or inside the incubator (37° C., ~5% CO$_2$). At each time point, a volume of 1 mL was withdrawn, the extract of sample prepared and analyzed by HPLC.

Preparation of extracts: a sample (1 mL) from each incubated mixture with compound (13) was treated with MeCN (1 mL), vortexed and centrifuged (2,000 rpm, 15 min). The supernatant was removed and the radioactivity measured. Aliquots of supernatant (250-500 µL) were acidified to pH~6 with 0.05 N TFA (2-8 µL). The excess of MeCN was evaporated with a stream of nitrogen and water (100 µL) added. A mixture was passed through a 0.2µ filter and each sample (~100 µL, 111-185 kBq) injected on the HPLC system.

analysis of extracts: proceeded on ACE C18 100 Å (5 µm, 4.6×250 mm) column; eluted at 0.8 mL/min with a linear gradient of MeCN from 0 to 95% over 50 min and 95% MeCN was kept for a period of further 20 min, detecting the radioactivity (Bioscan NaI(T)). Both solvents contained 0.07% TFA (v/v).

Figures 6A, 6B:
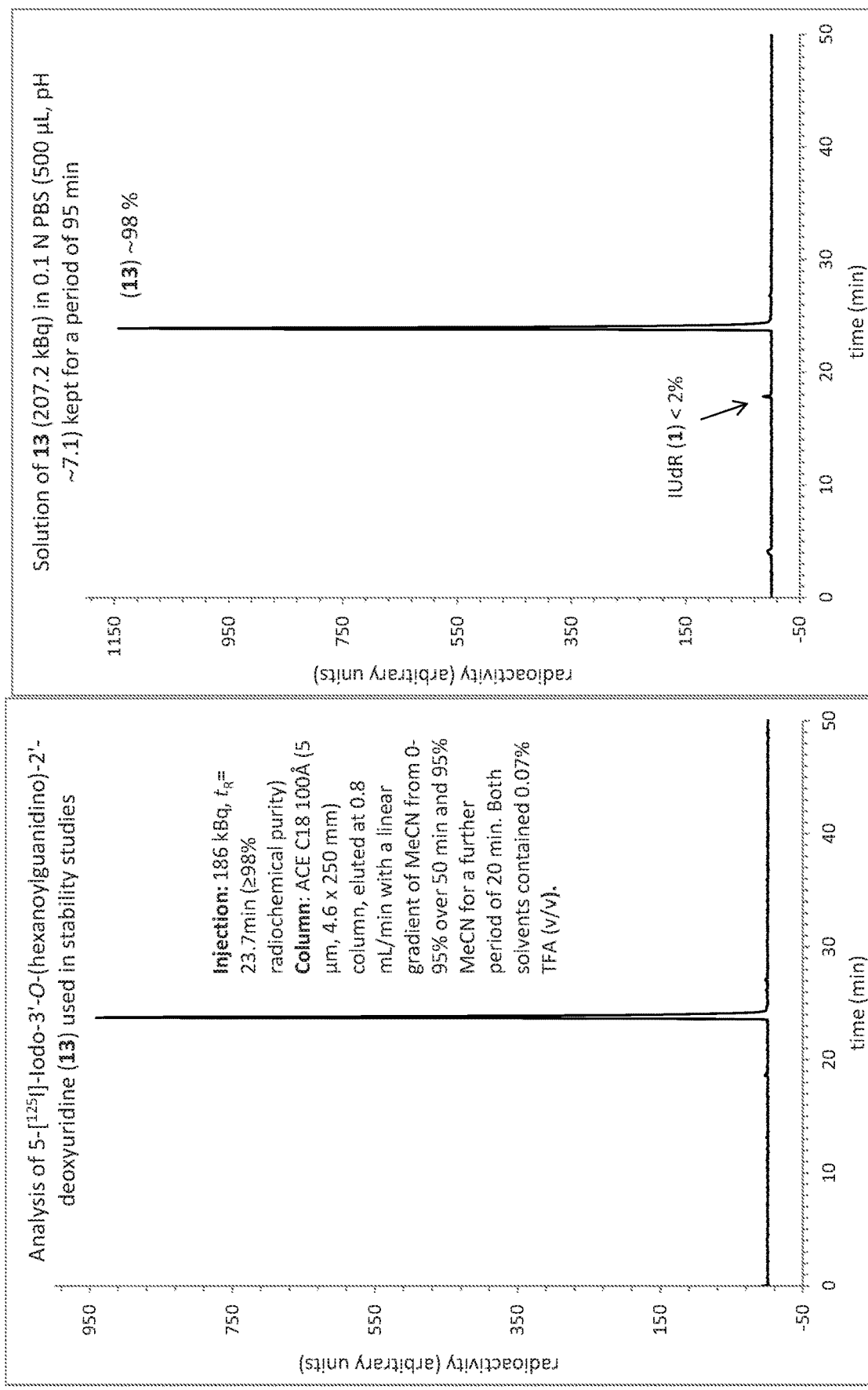
FIG. 6A-FIG. 6N are a set of graphs showing HPLC analysis demonstrating the stability of 5-[$^{125}$I]-Iodo-3'-O-hexanoylguanidino-2'-deoxyuridine (13)
Figures 6C, 6D:
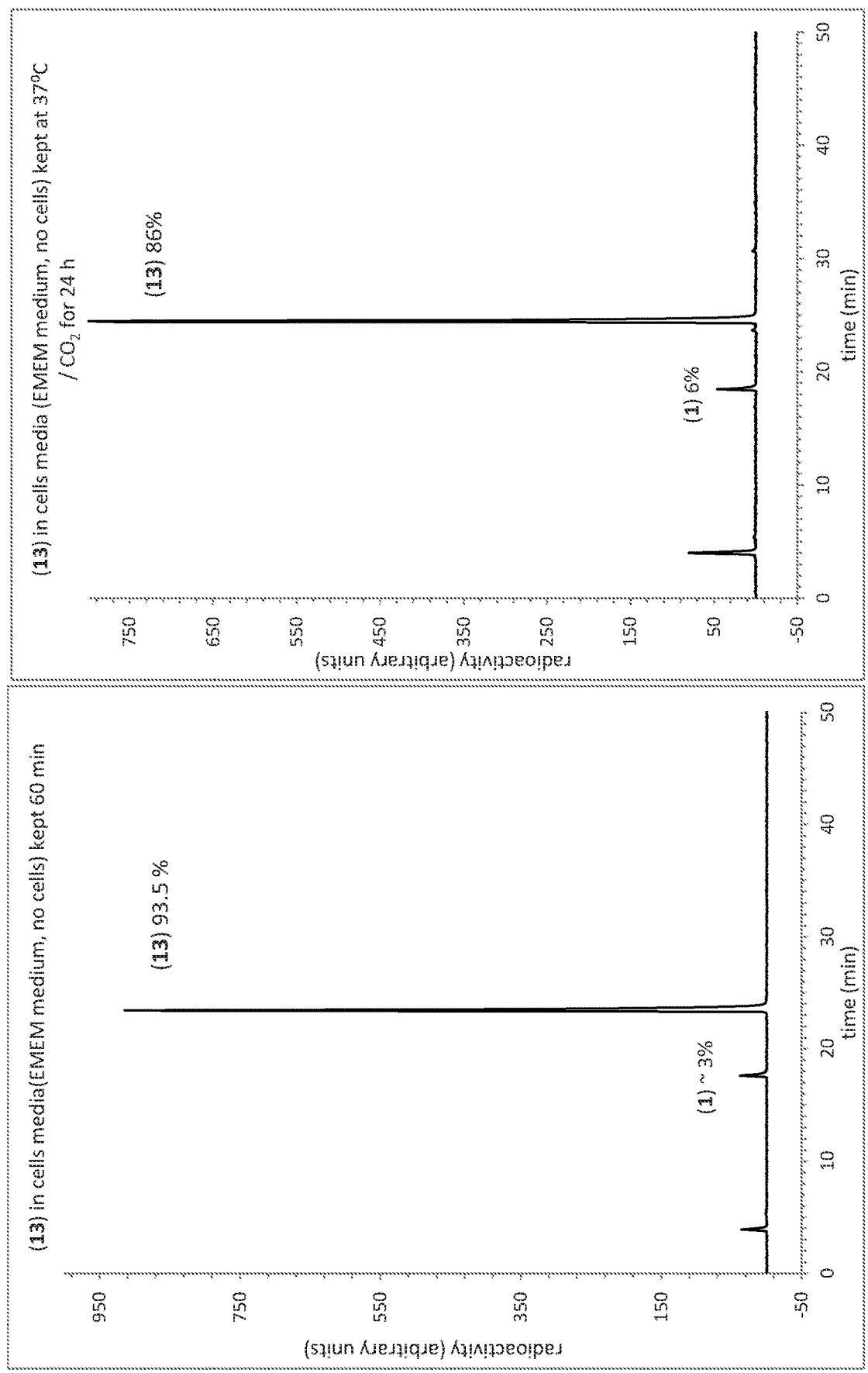
Figures 6E, 6F:
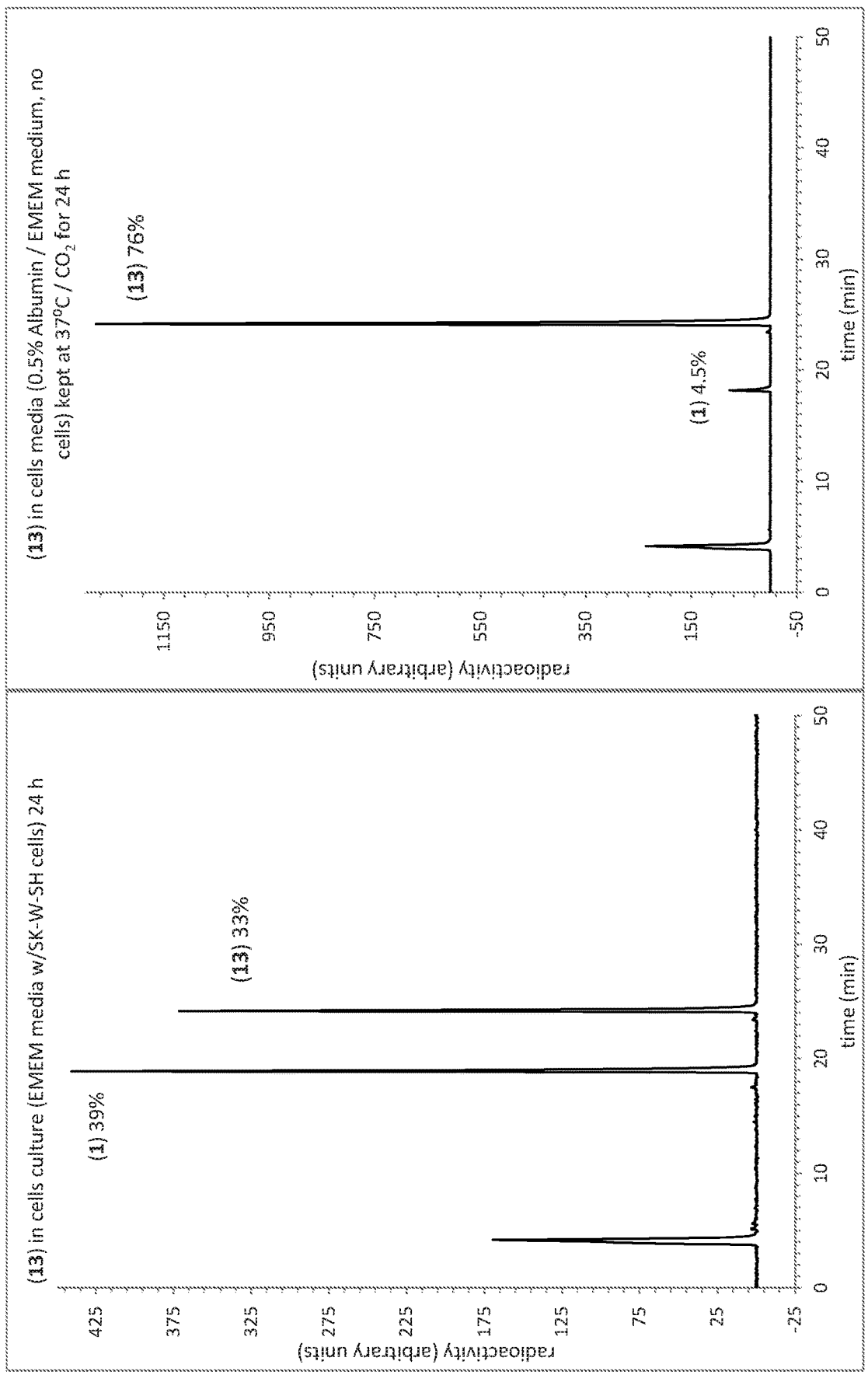
Figures 6G, 6H:
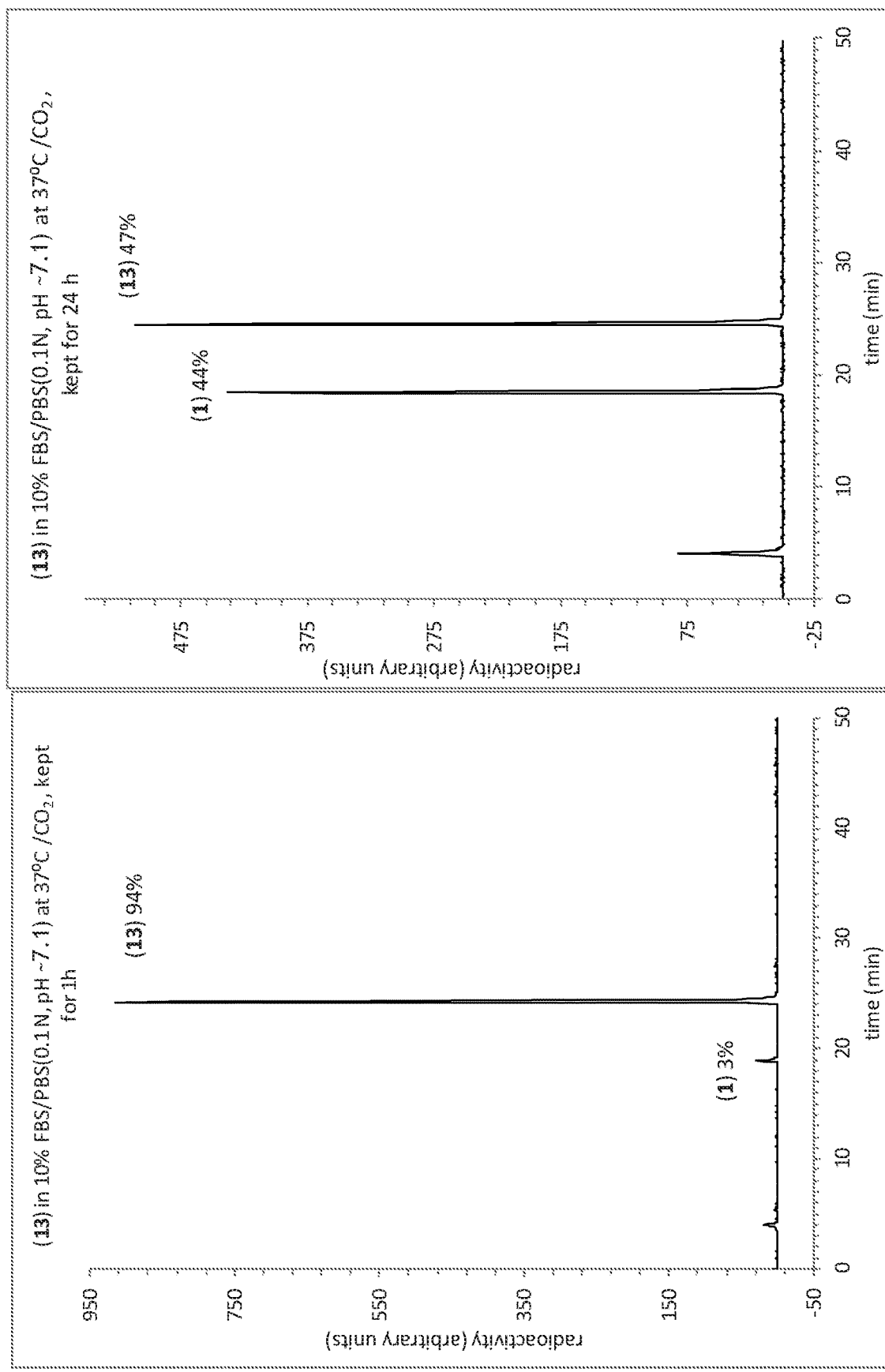
Figures 6I, 6J:
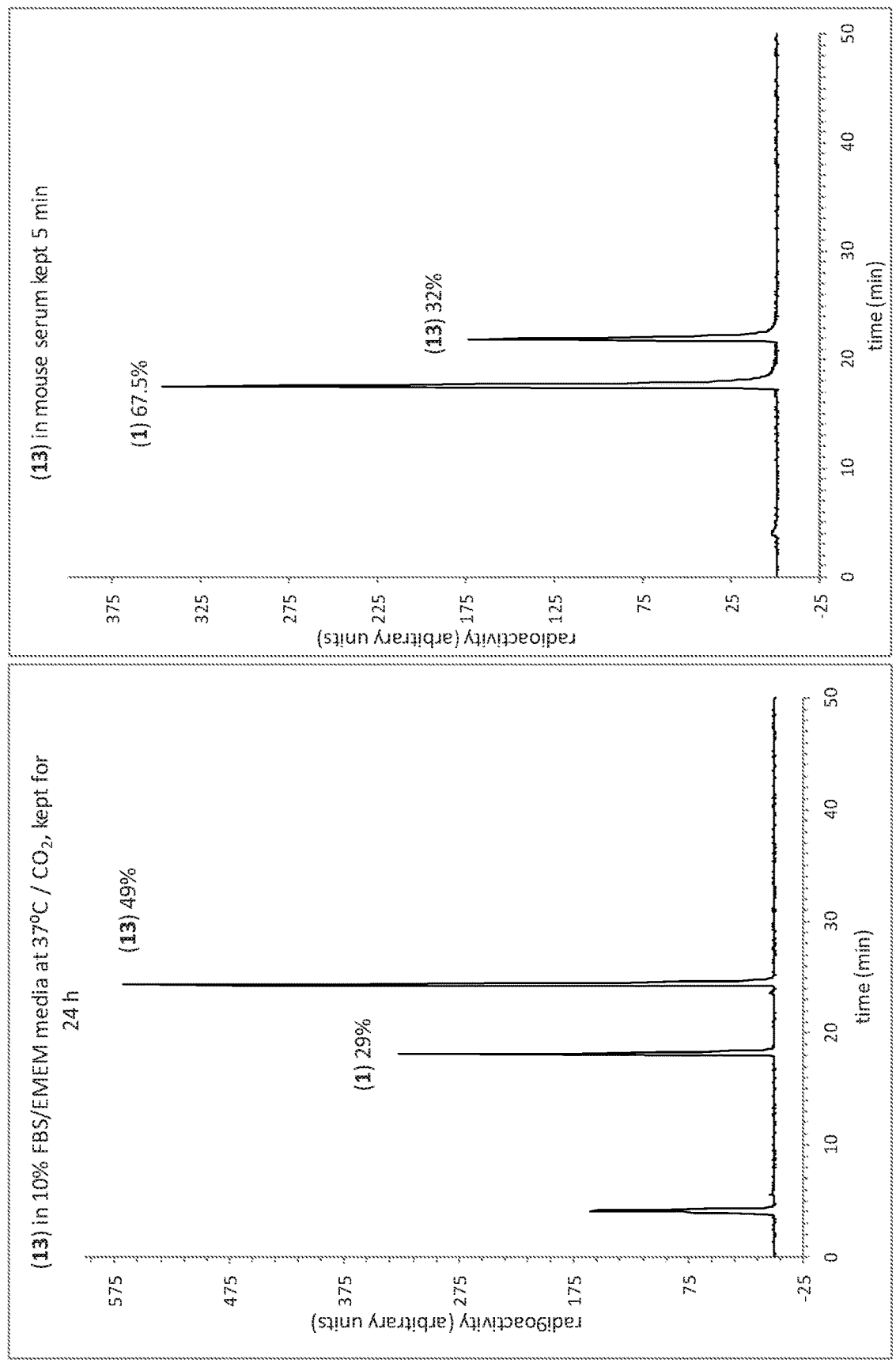
Figures 6K, 6L:
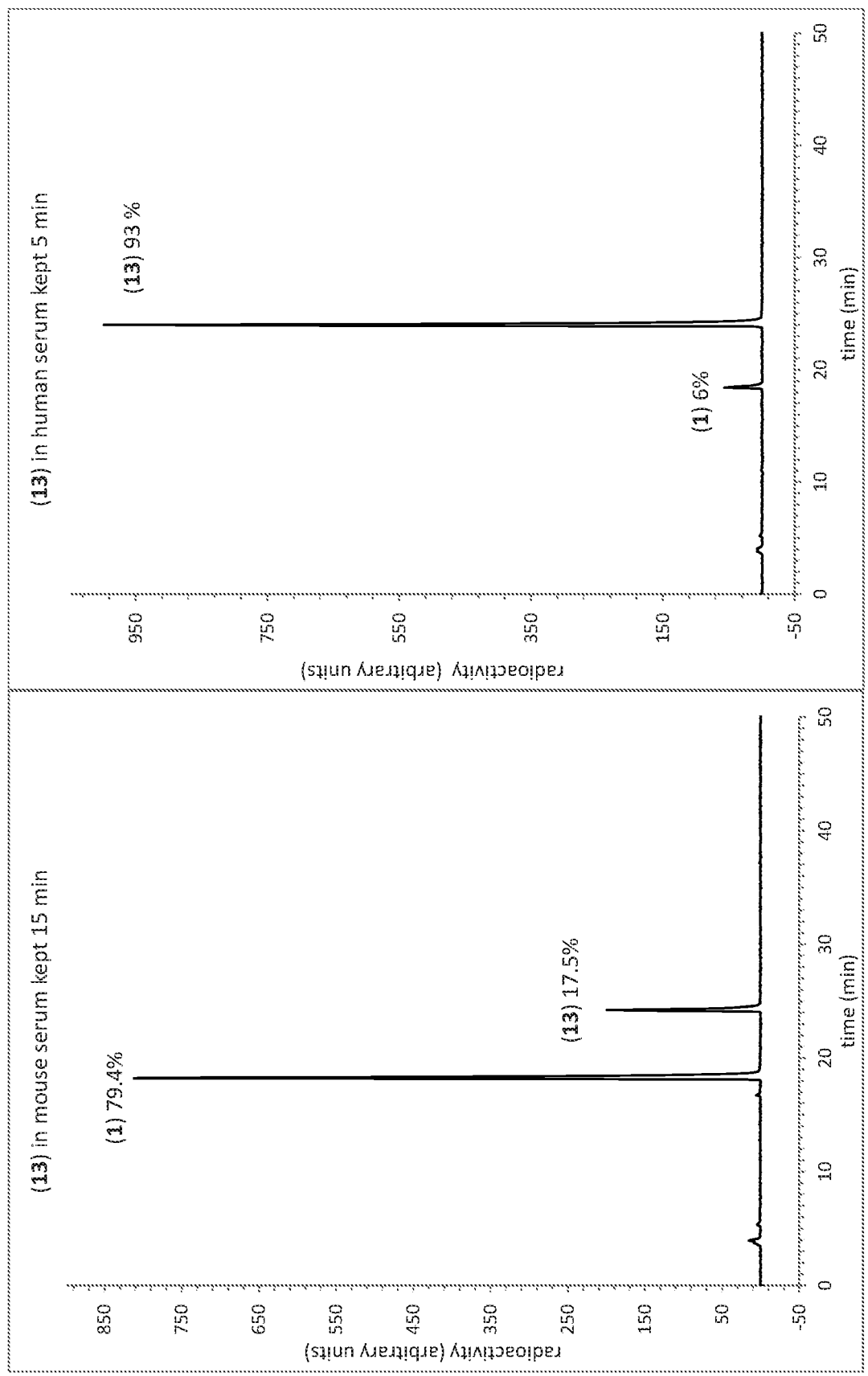
Figures 7A, 7B:
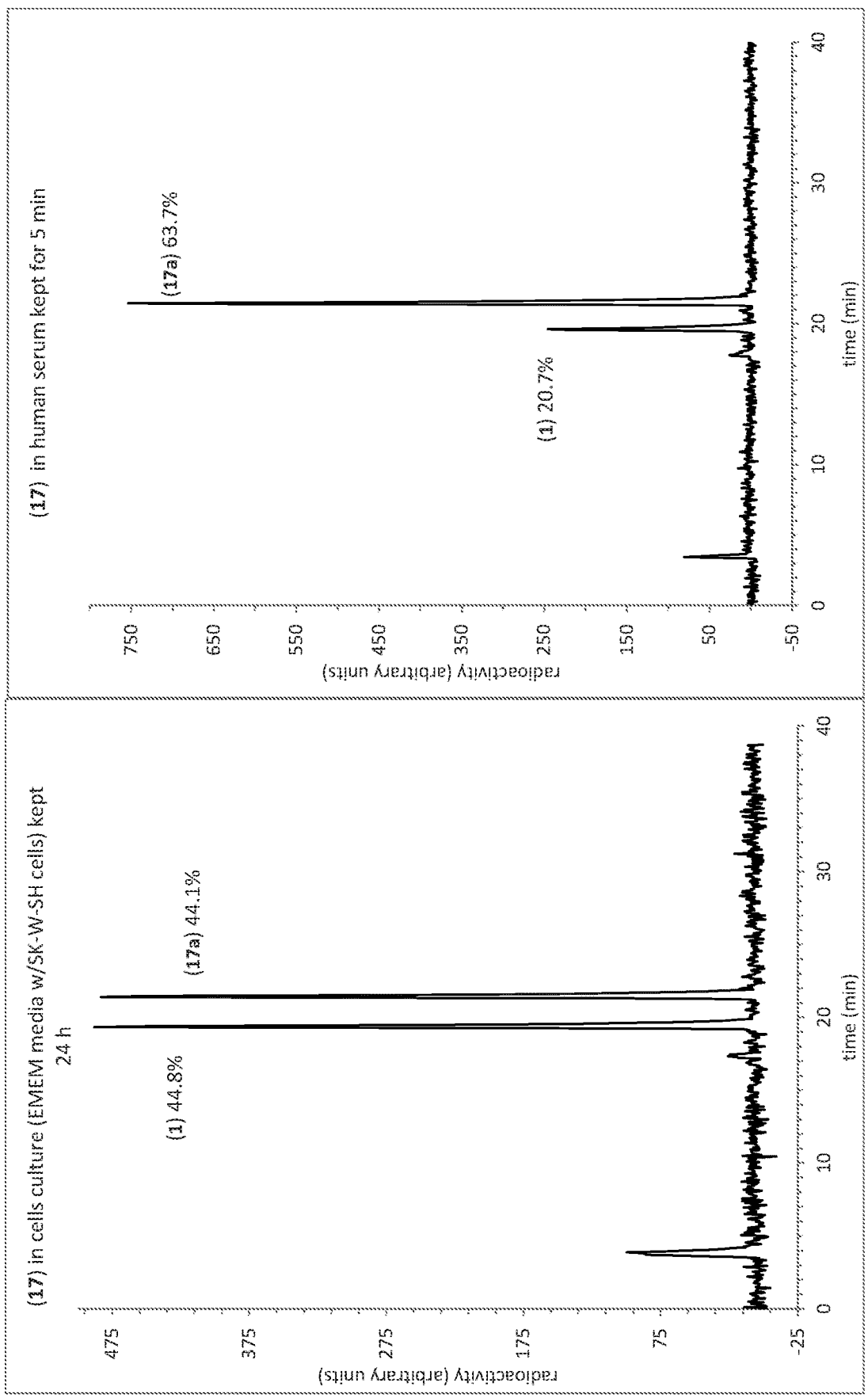
FIG. 7A-FIG. 7D are a set of graphs showing HPLC analysis demonstrating the stability of 5-[$^{125}$I]-Iodo-3'-O-(hexanoylguanidino)-2'-deoxyuridine (17a)
Figures 7C, 7D:
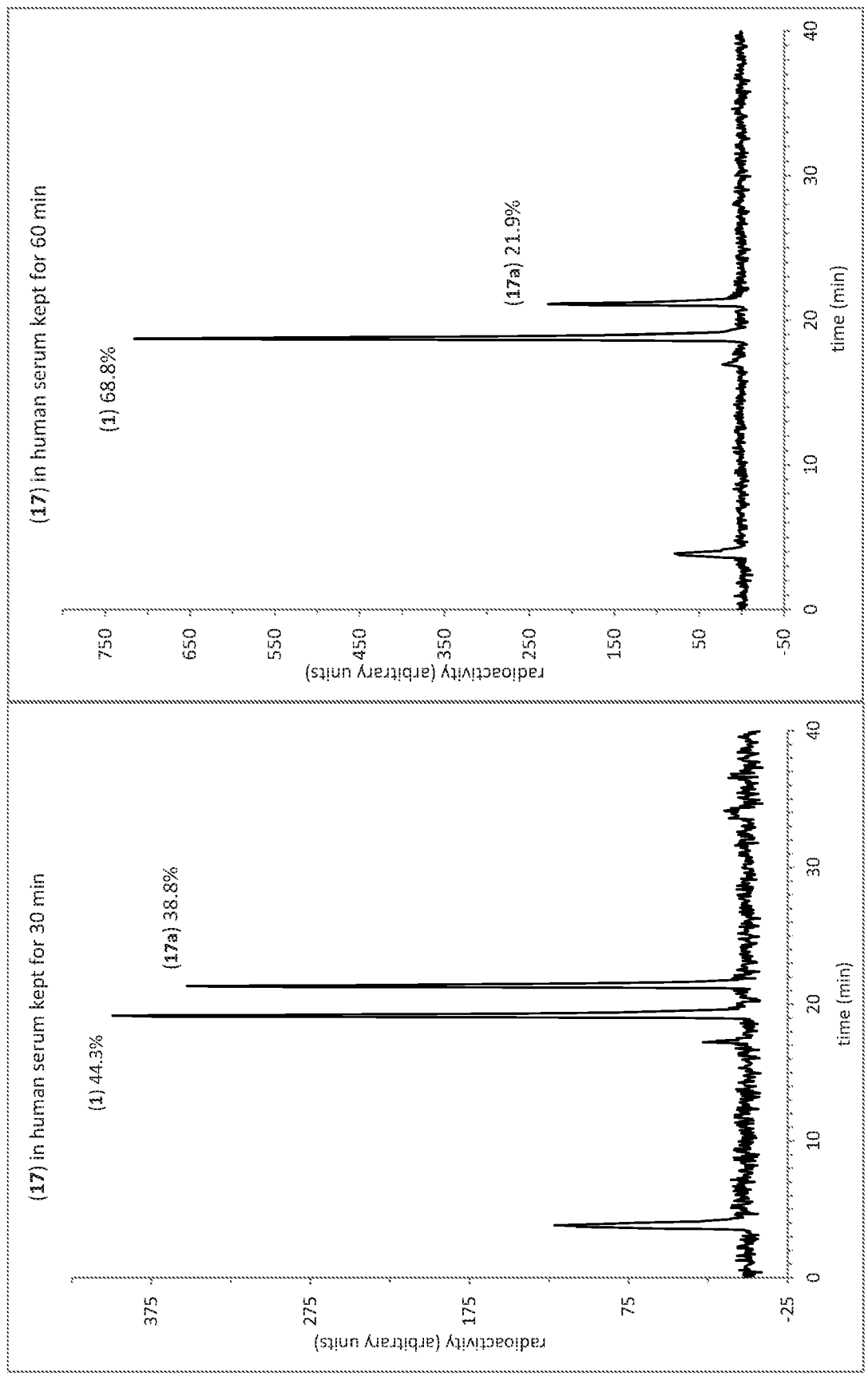
Figures 8A, 8B:
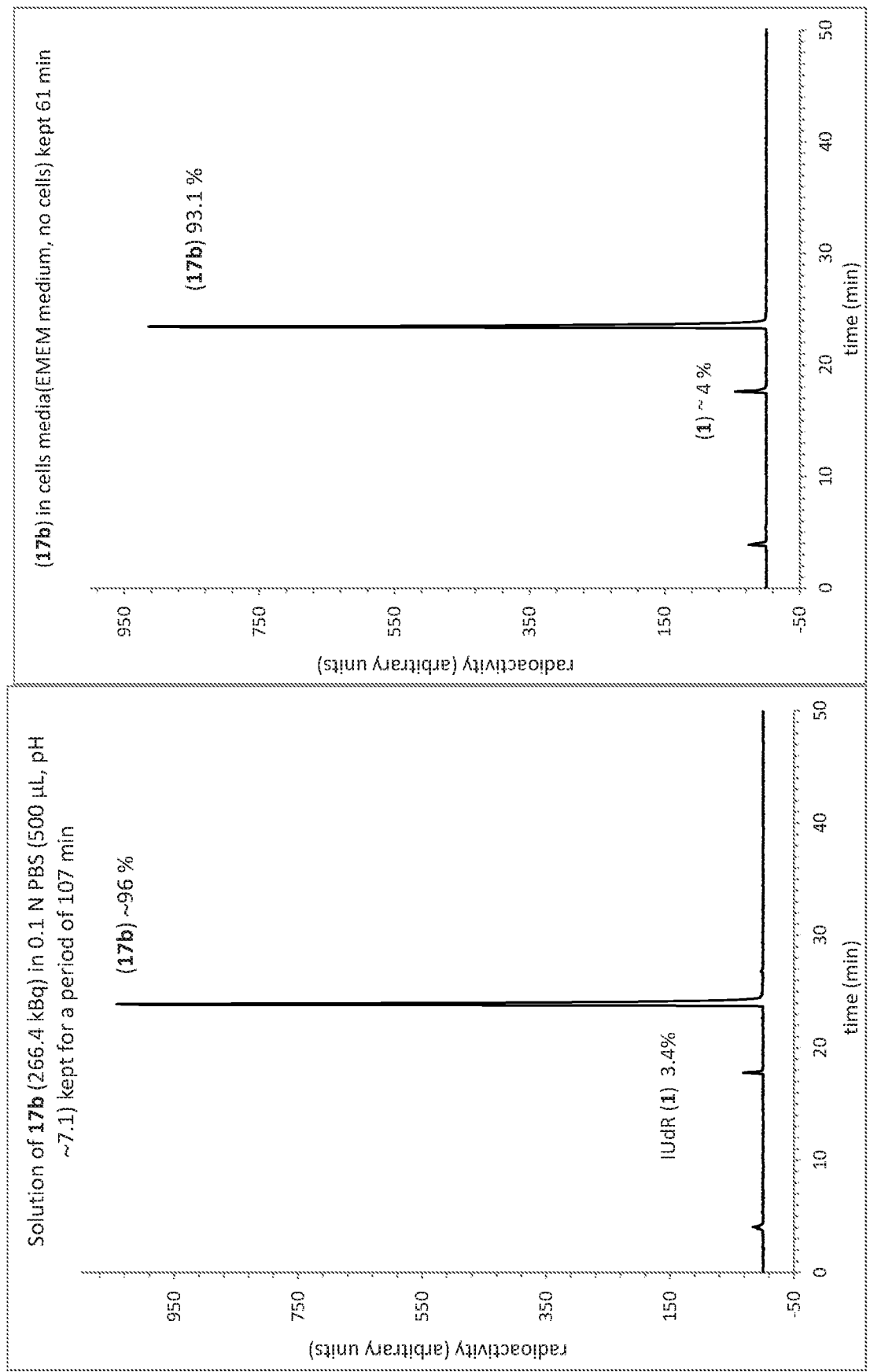
Figures 8C, 8D:
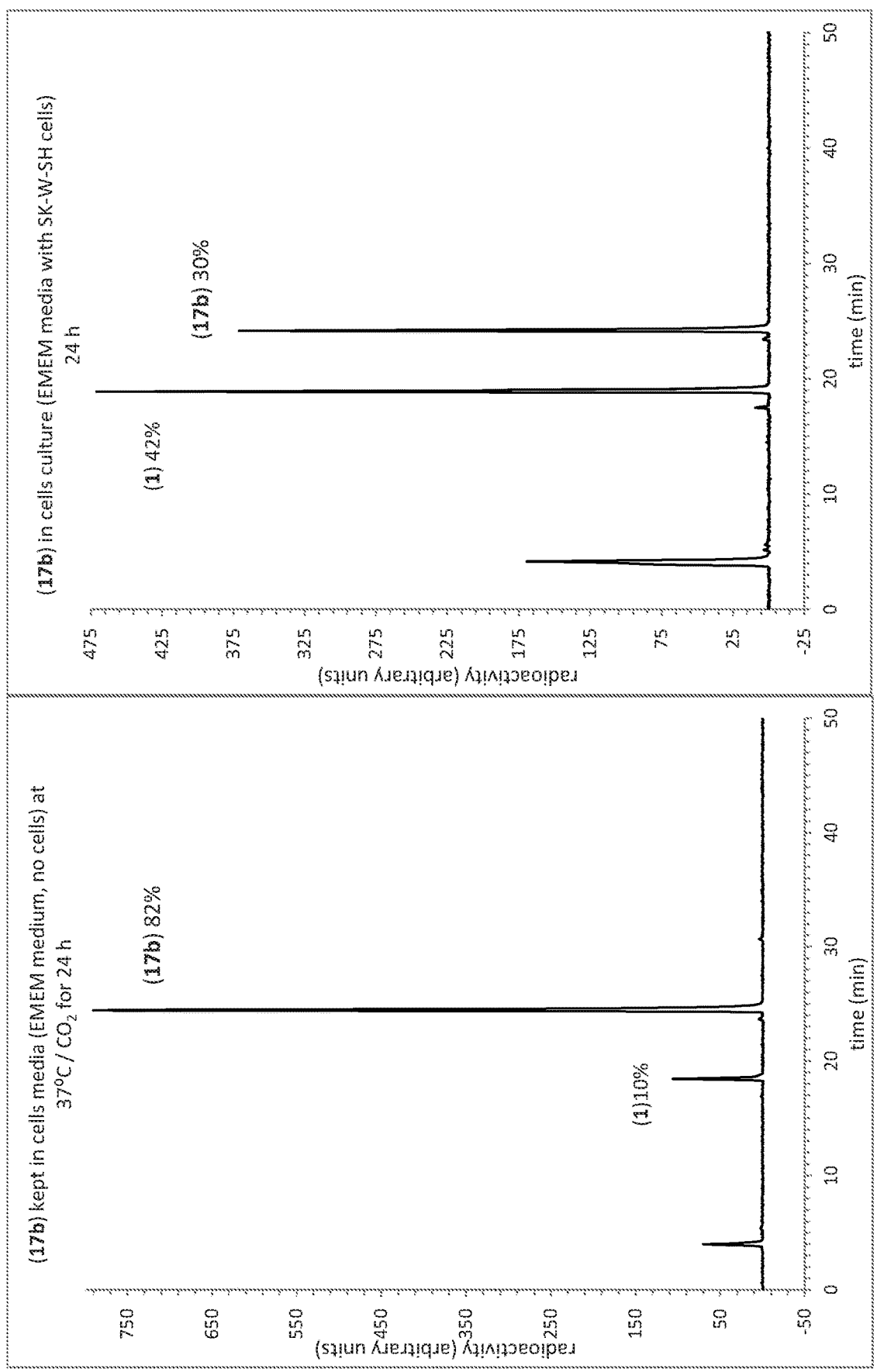
Figures 8K, 8L:
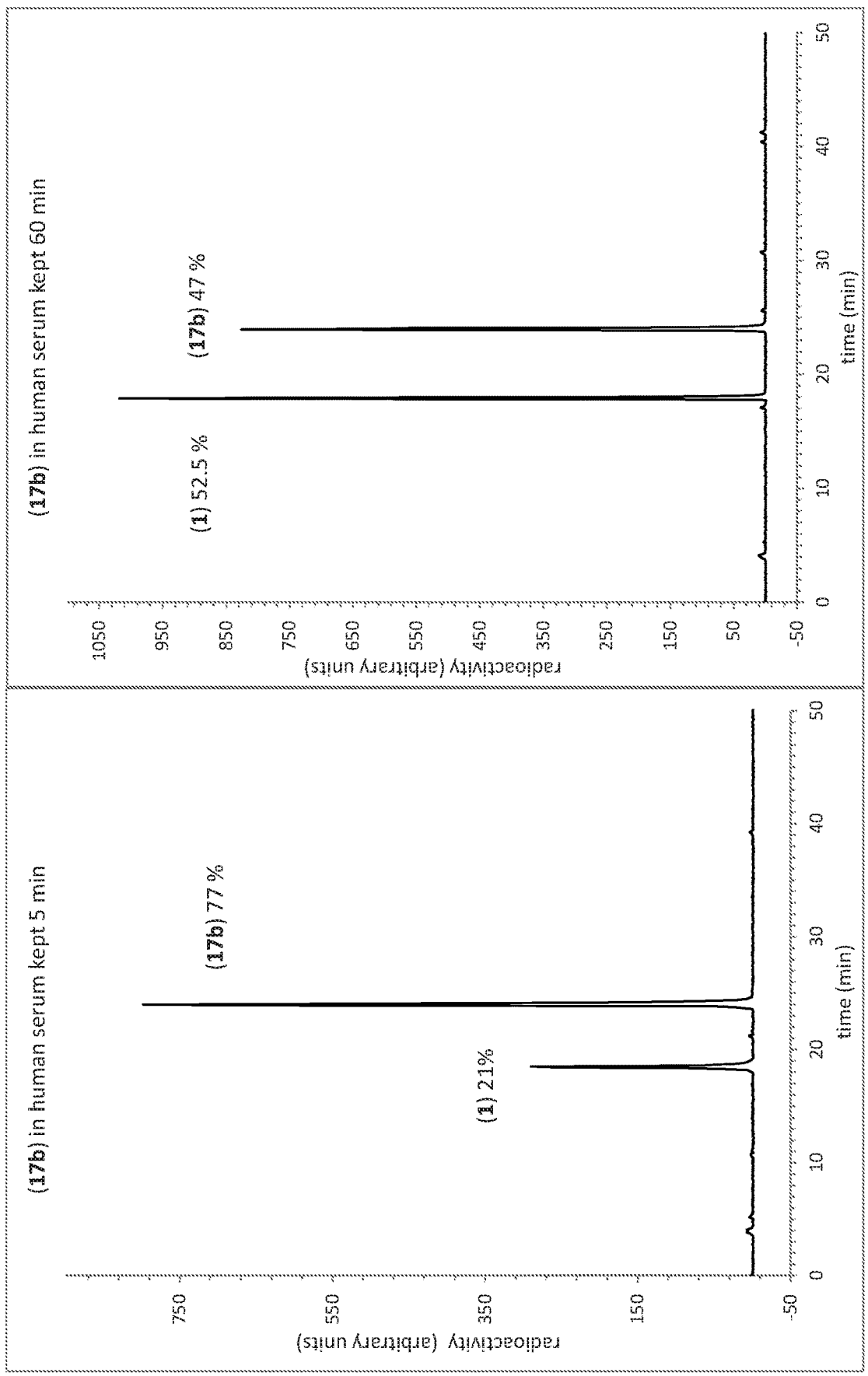
Figure 8M:
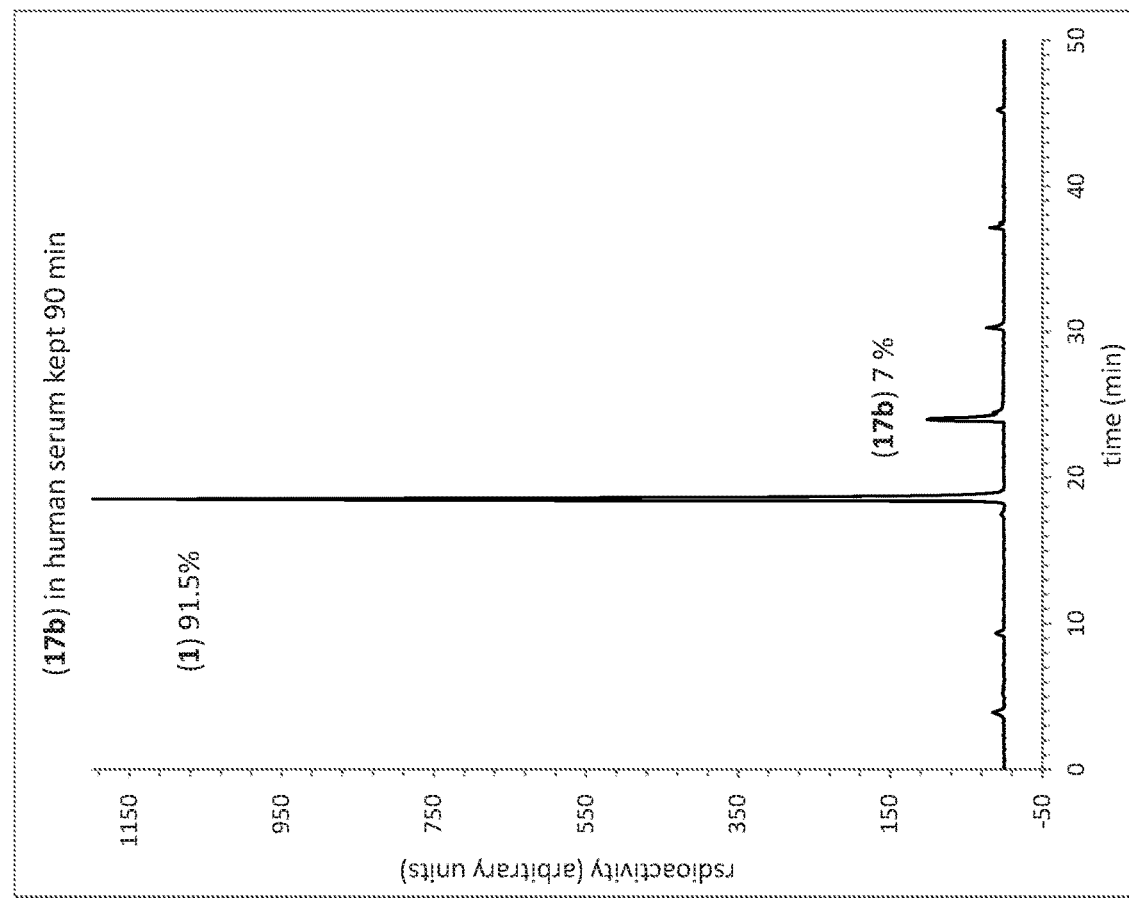
Figures 9A, 9B:
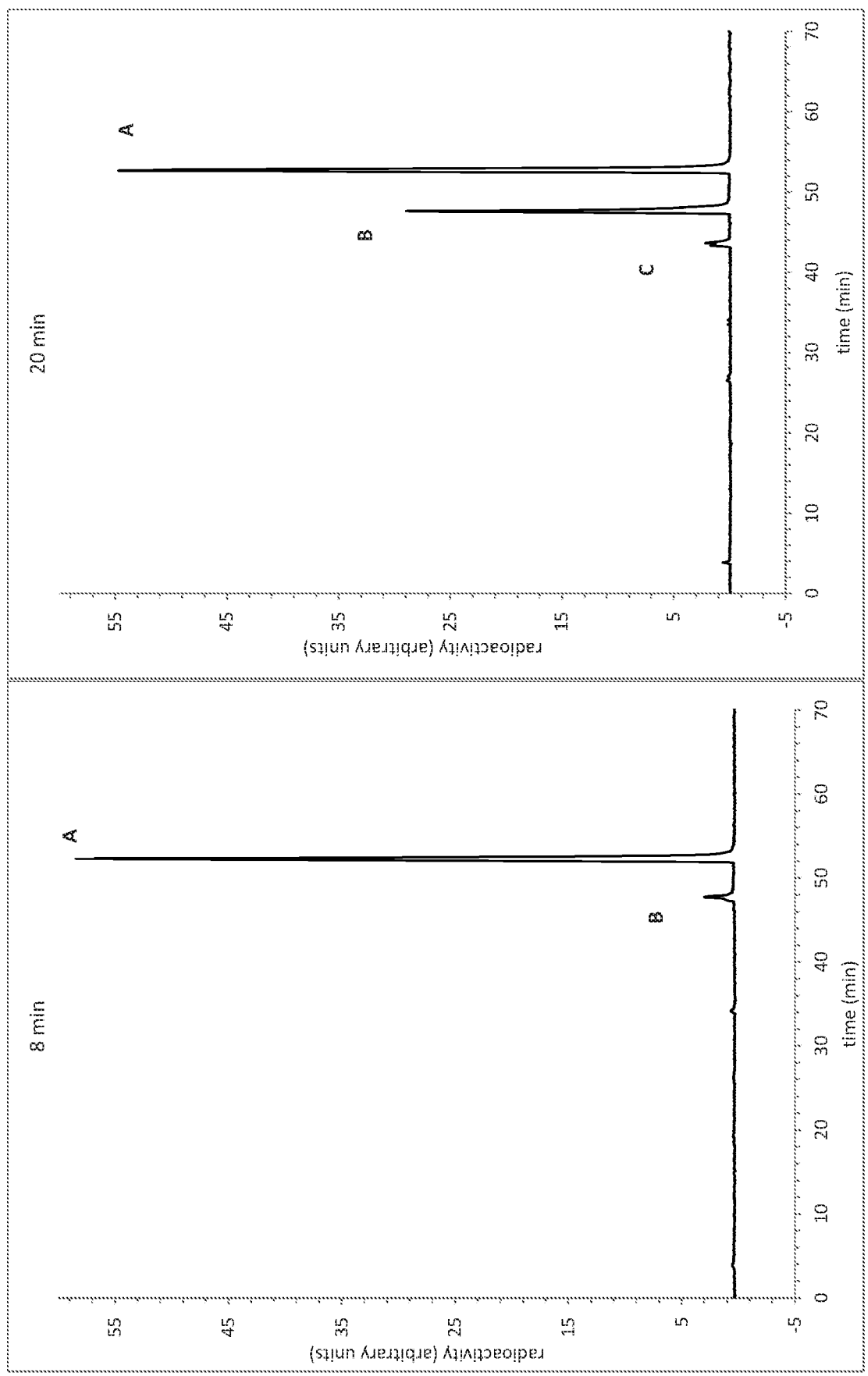
FIG. 9A-FIG. 9D are a set of graphs showing HPLC analysis demonstrating the deprotection of 5-[$^{125}$I]-Iodo-5'-O-[cyclo-3,5-di(tert-butyl)-6-fluorosaligenyl]-3'-O—[(N, N'-bis(tert-(butyloxycarbonyl)-N''-hexanoyl)guanidino]-2'-deoxyuridine Monophosphate (20)
Figures 9C, 9D:
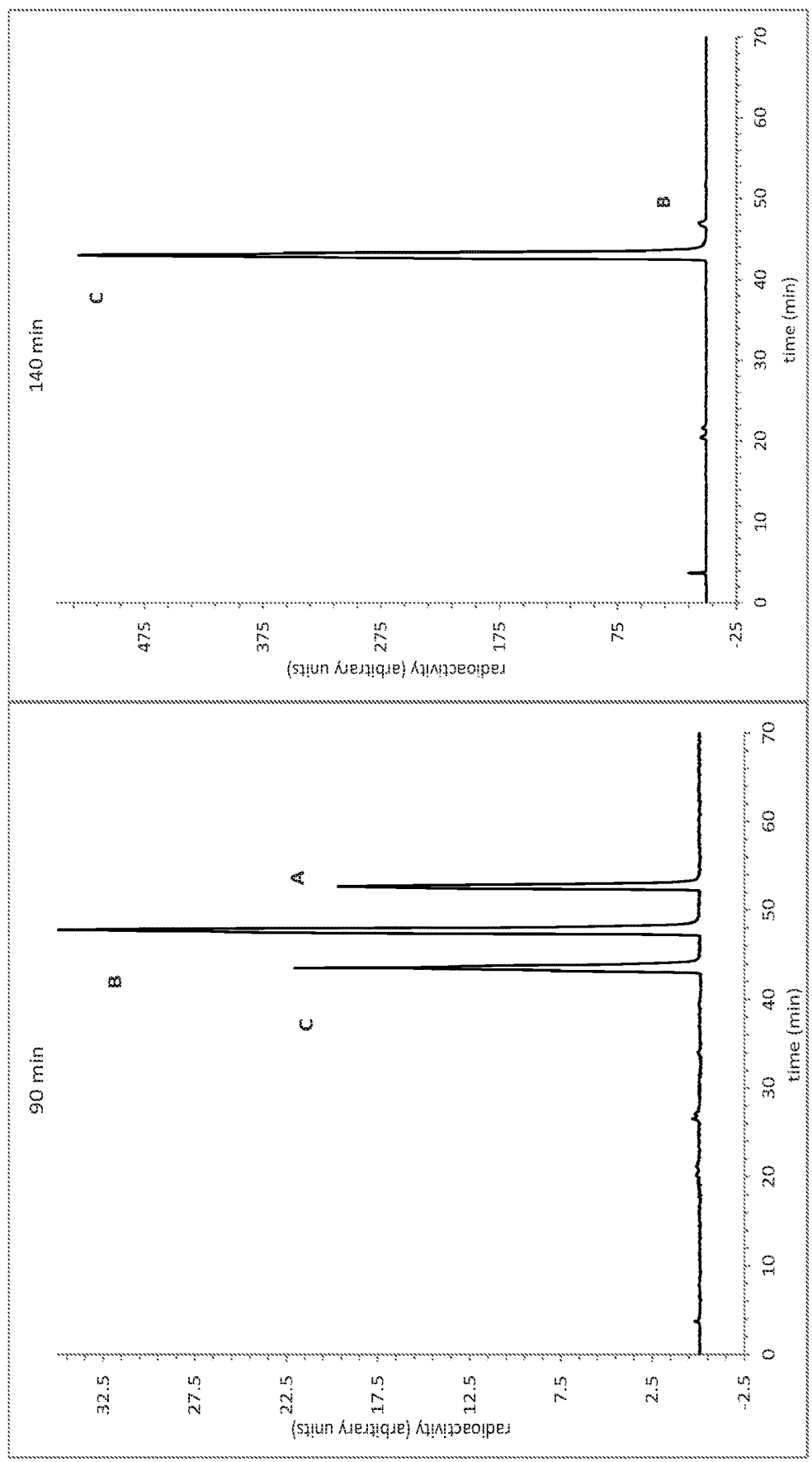
Figures 10A, 10B:
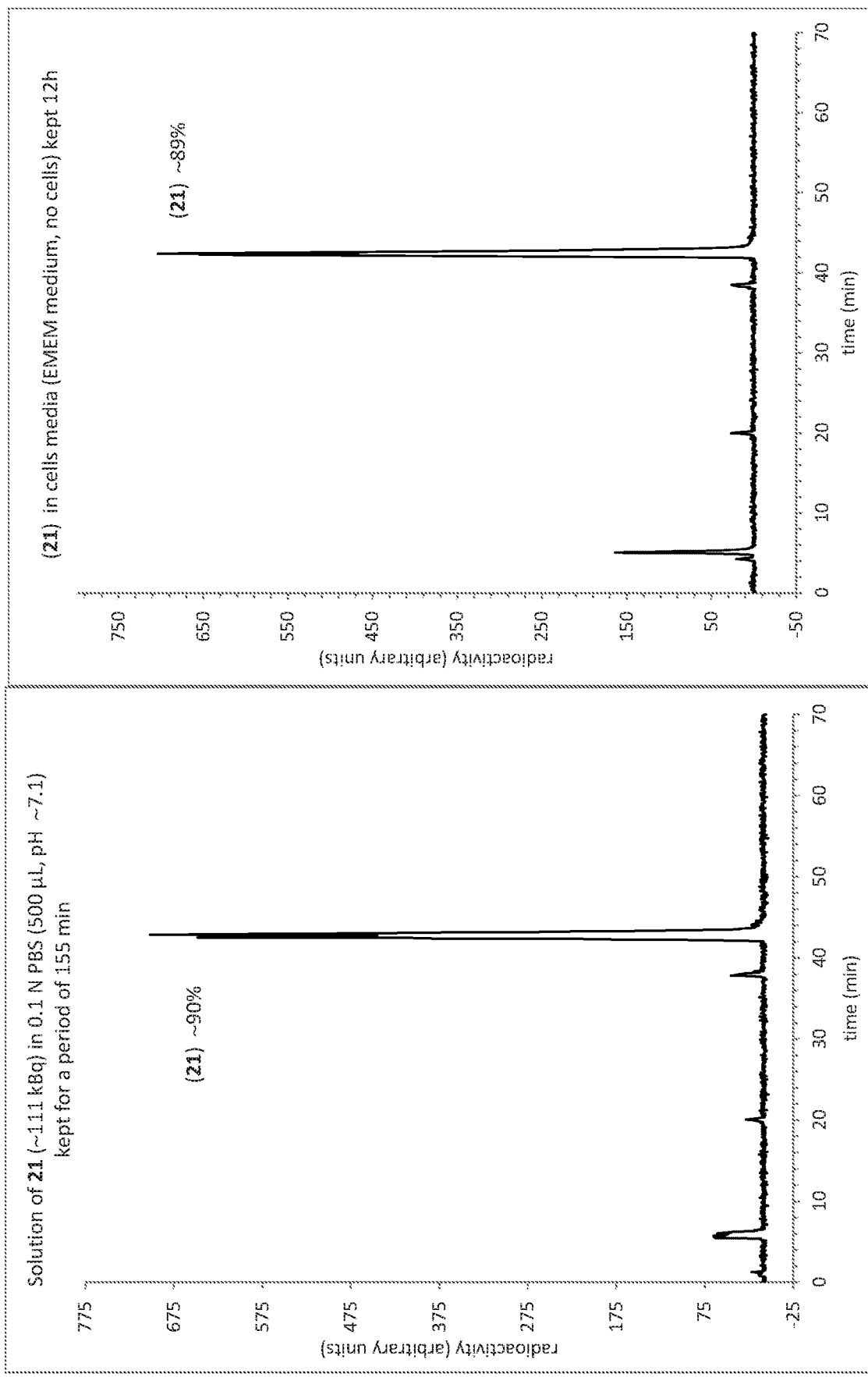
FIG. 10A-FIG. 10G are a set of graphs showing HPLC analysis demonstrating the stability of 5-[125I]-Iodo-5'-O-[cyclo-3,5-di(tert-butyl)-6-fluorosaligenyl]-3'-O-hexanoylguanidino]-2'-deoxyuridine Monophosphate (21)
Figures 10C, 10D:
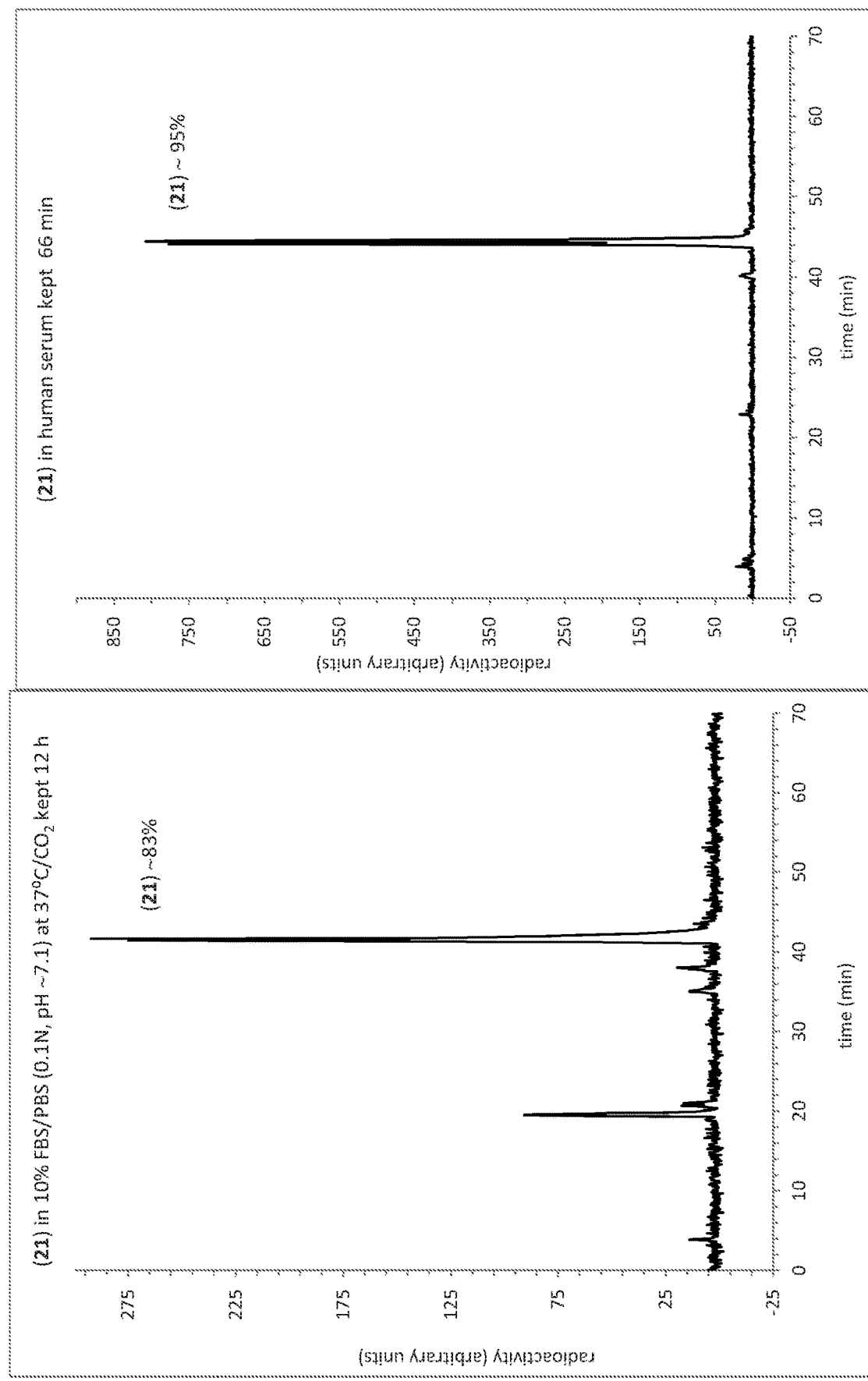
Figures 10E, 10F:
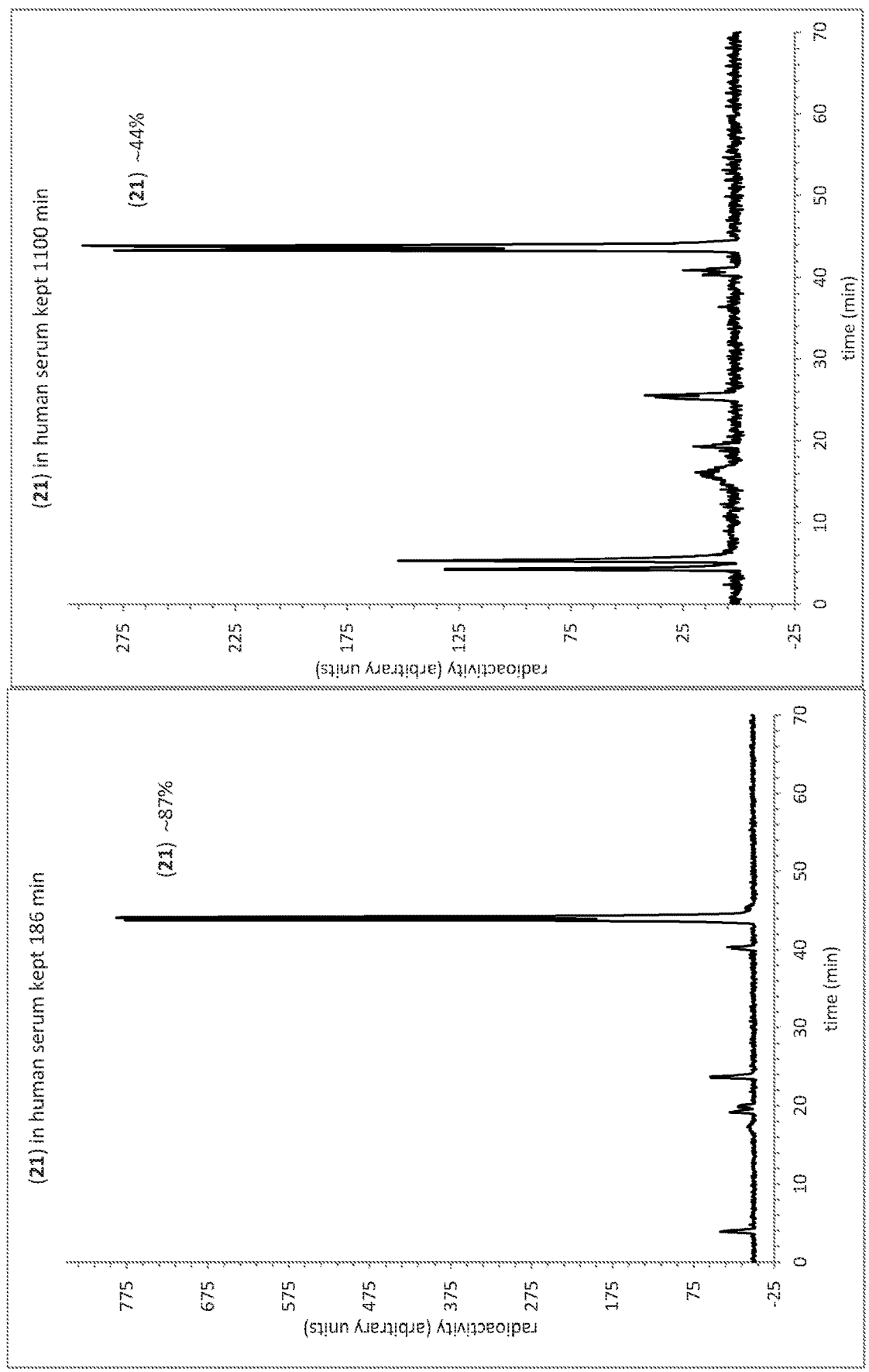
Figure 10G:
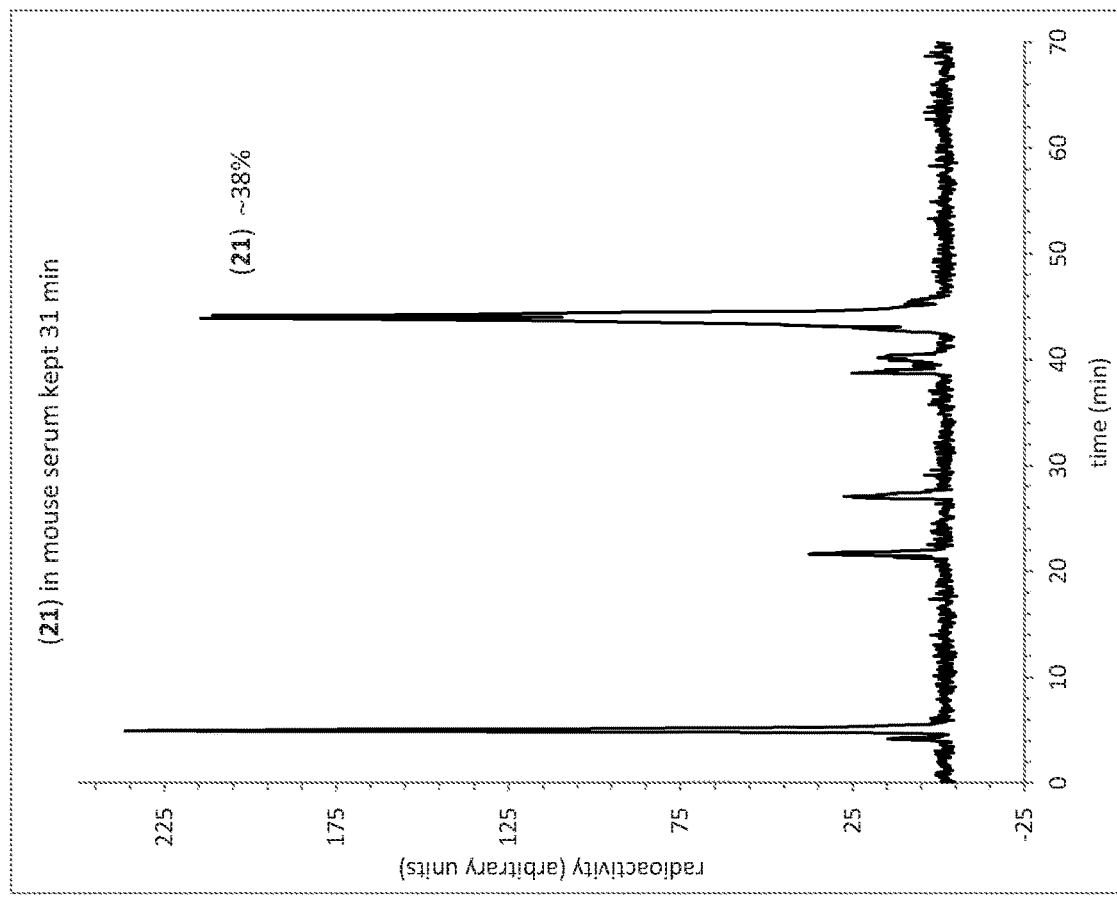
Figures 11A, 11B:
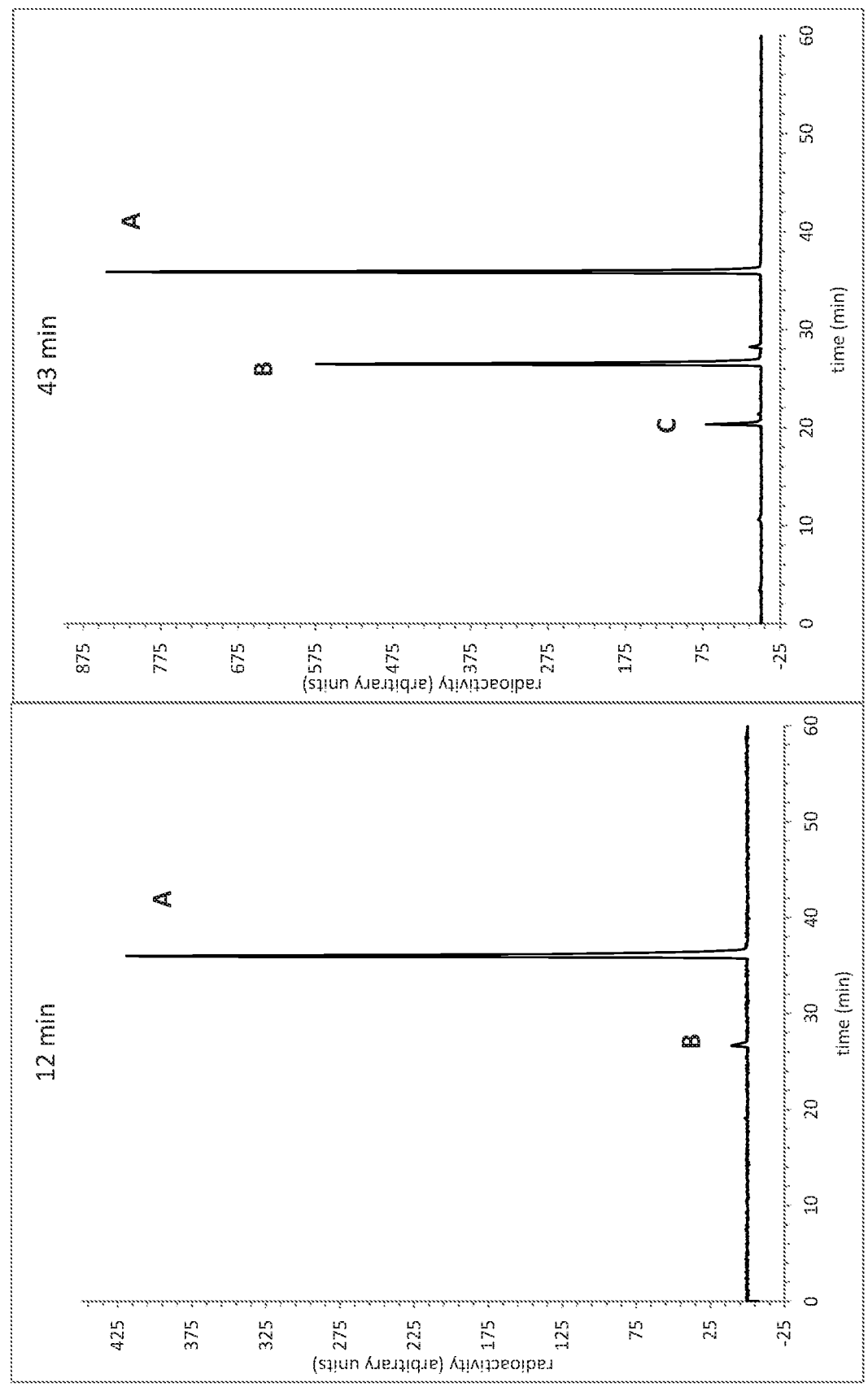
FIG. 11A-FIG. 11D are a set of graphs showing HPLC analysis demonstrating the deprotection of 5-[$^{125}$I]-Iodo-5'-O—[(N,N'-bis(tert-(butyloxycarbonyl)-N''-methyl-4-benzoyl)-guanidino]-2'-deoxyuridine (24)
Figures 11C, 11D:
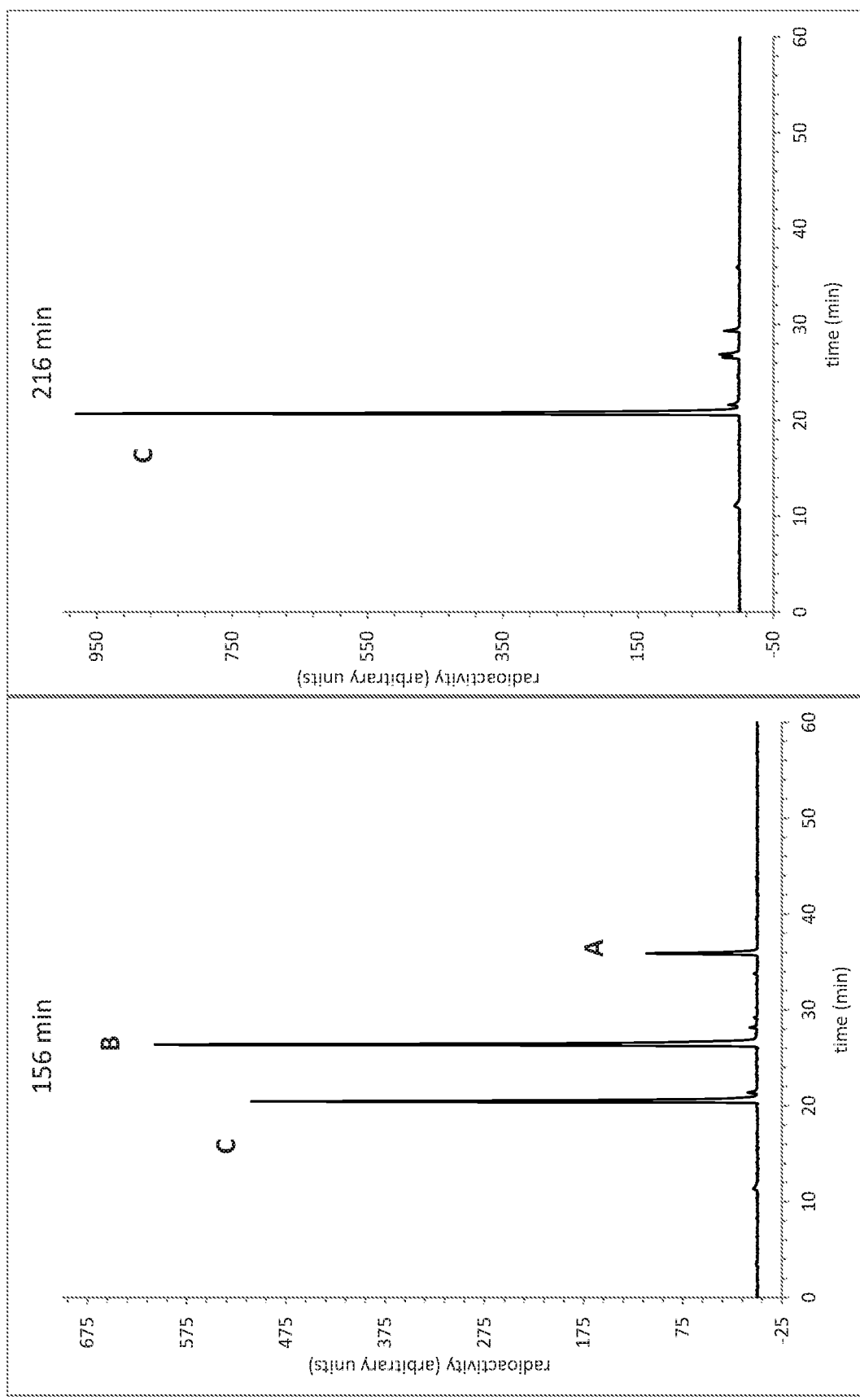
Figures 12A, 12B:
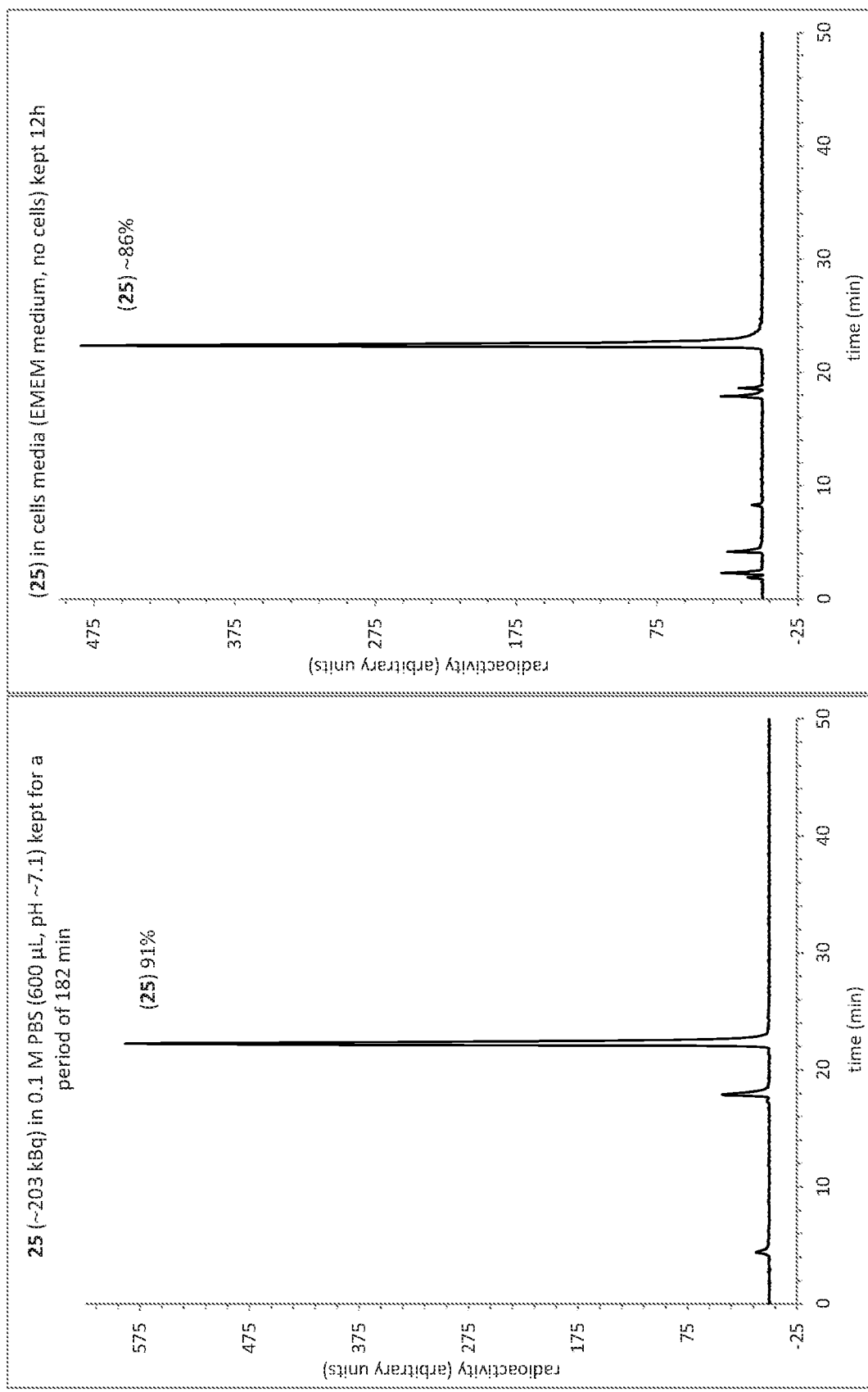
FIG. 12A-FIG. 12G are a set of graphs showing HPLC analysis demonstrating the stability of 5-[$^{125}$I]-Iodo-5'-O-methyl-4-benzoylguanidino-2'-deoxyuridine (25)
Figures 12C, 12D:
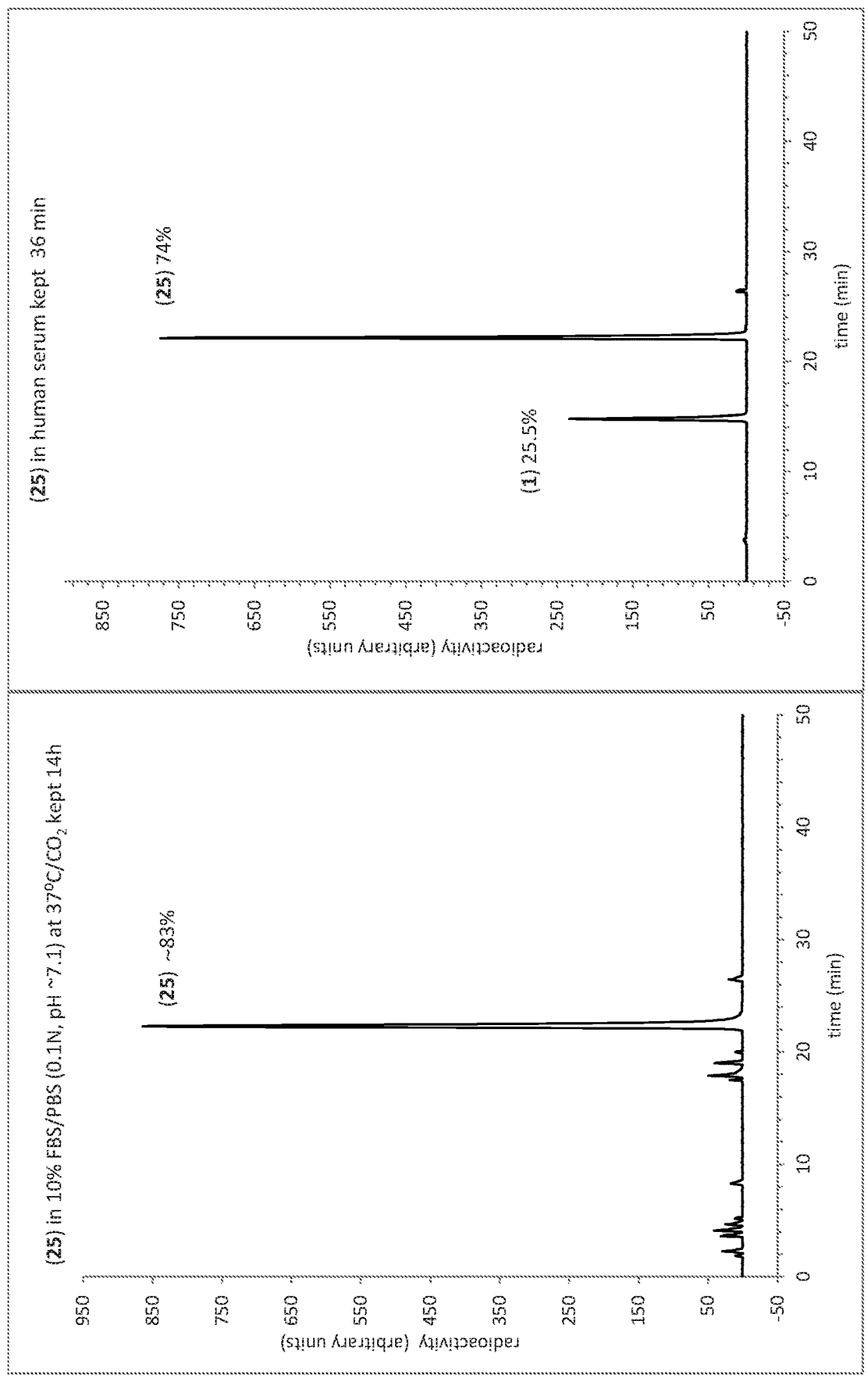
Figures 12E, 12F:
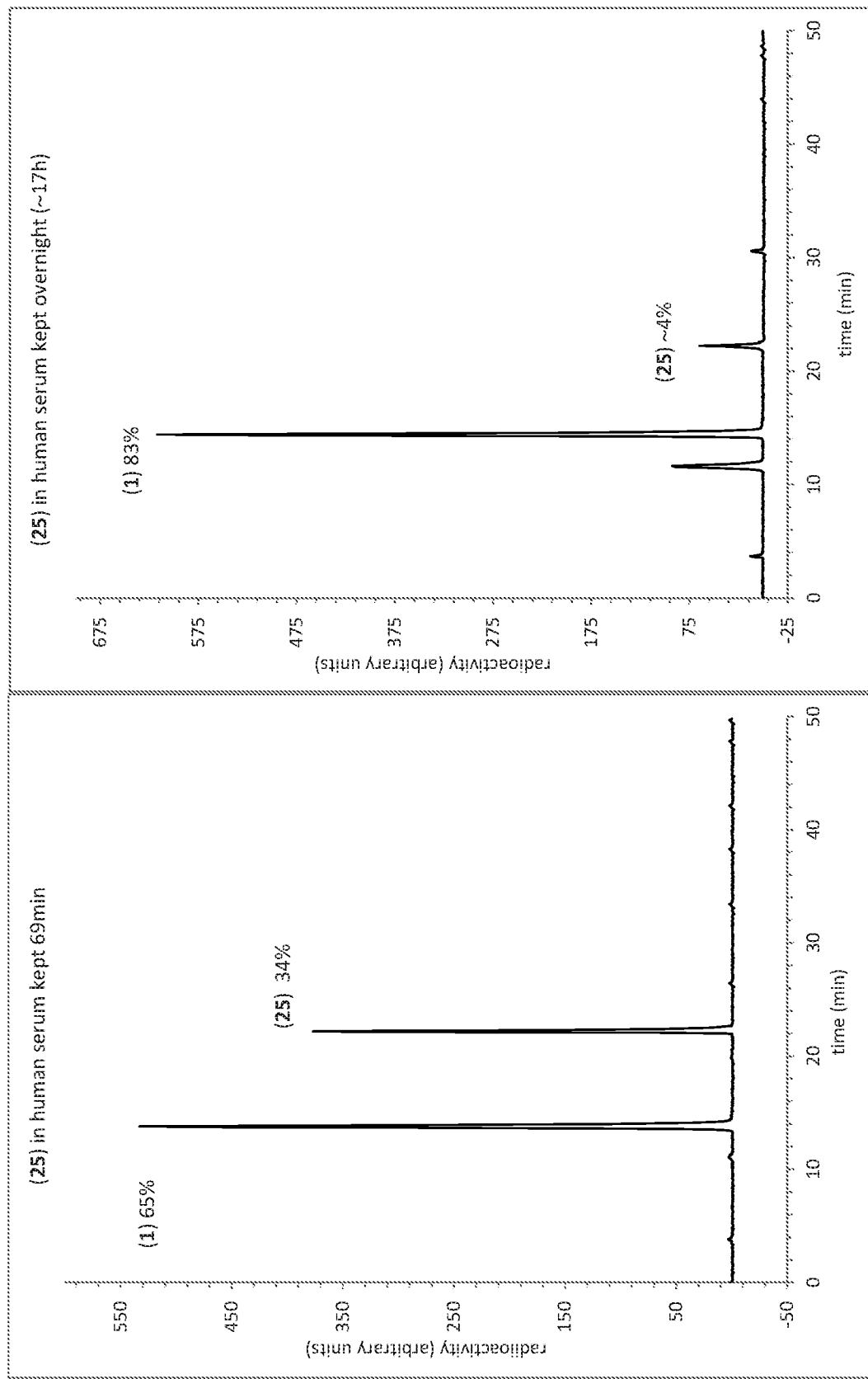
Figure 12G:
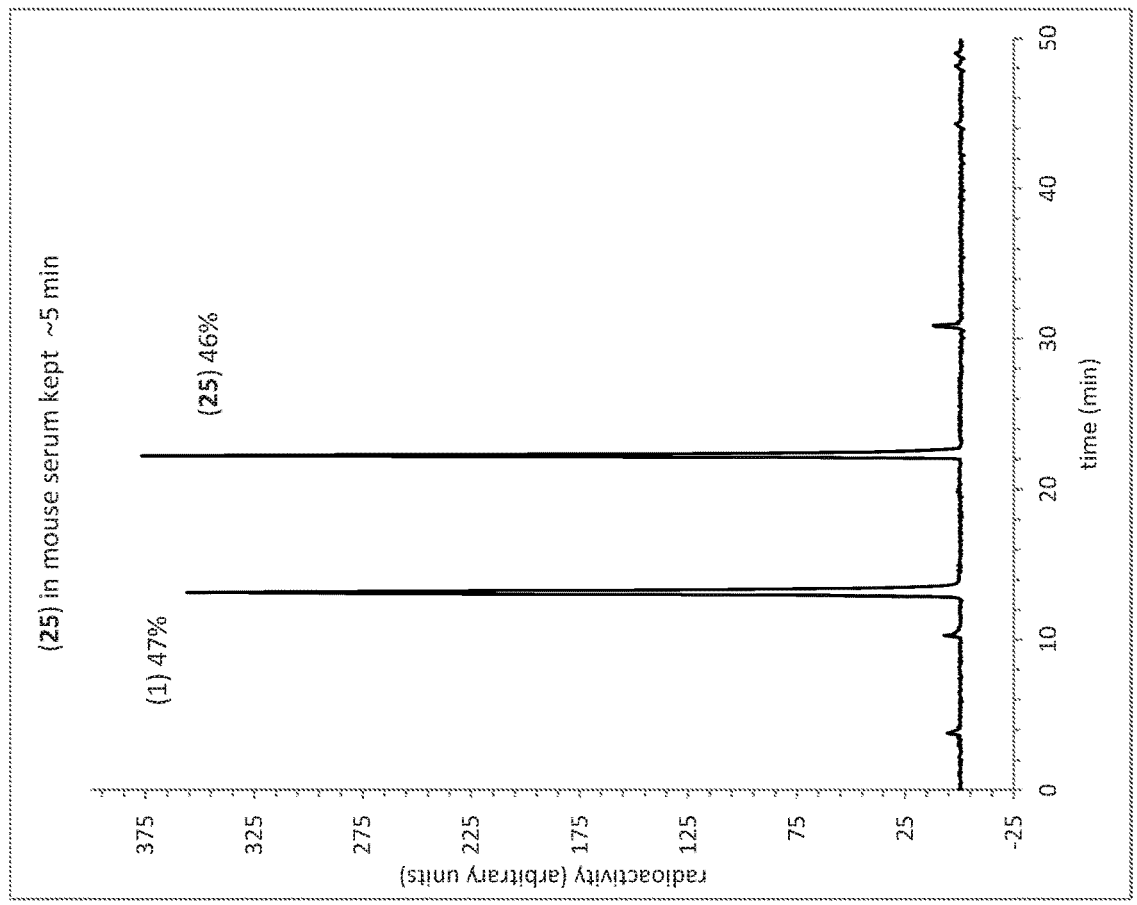

The examples of the results from the stability studies of (13) are depicted in FIGS. 6A-6N.

5-Iodo-5'-O—[(N,N'-bis(tert-(butyloxycarbonyl)-N"-propionyl)-guanidino]-2'-deoxyuridine (14a)

The preparation of (14a) began with 5-iodo-3'-O-levulinyl-2'-deoxyuridine (3), attained via esterification of 4-oxopentanoic acid with 5-iodo-5'-O-trityl-2'-deoxyuridine, using the DCC/DMAP activation method, and the subsequent cleavage of the trityl group by ZrCl$_4$ in CH$_3$CN. The 3'-O-protected uridine (3) was then reacted with Boc-β-alanine (DCC/DMPA activation) to yield 5-iodo-5'-O-(3-N-Boc-aminopropionyl)-3'-O-levulinyl-2'-deoxyuridine, which after elimination of the N-Boc protecting group in 15% TFA/MeCN, guanidinylation with N,N'-bis(tert-butyloxycarbonyl)-N"-trifluoro-methane-sulfonyl guanidine and the final deprotection of 3'-O-Lev group, led to the target guanidinoalkyl ester (14a) in 73% yield (detailed below). The first two required initial preparations were carried out as follows:

5-Iodo-3'-O-levulinyl-2'-deoxyuridine (3)

To a stirred solution of 5-iodo-5'-O-trityl-2'-deoxyuridine (5.02 g, 8.42 mmol) and levulinic acid (1.05 mL, 10.15 mmol) in 80 mL of DCM/DMF (200/1, v/v), DCC (2.1 g, 10.17 mmol) and DMAP (260 mg, 2.13 mmol) were added. Upon completion of the reaction (~4 h, TLC monitoring) the mixture was filtered and the filtrate evaporated under reduced pressure. An oily residue was treated with EtOAc/hexanes (3/1, v/v), filtered again, evaporated, and a crude product separated by chromatography on a silica gel column using a gradient of MeOH in DCM (0.2-0.4:10) to give 5.54 g (94%) of the 5-iodo-5'-O-trityl-3'-O-levulinyl-2'-deoxyuridine (R value 0.65 in DCM/MeOH 10:0.4); 5.05 g (7.27 mmol) of which was dissolved in MeCN (60 mL) with stirring and ZrCl$_4$ (1.71 g, 7.29 mmol) added. Cleavage of the trityl group was completed after ~1 h (TLC monitoring, EtOAc/MeOH, 10/0.1). The solvent was evaporated under reduced pressure, and to a solid residue, 100 mL of EtOAc and water (30 mL) added. The organic phase was washed with brine and dried over MgSO$_4$. The solvent was partially evaporated (to 50 mL) and 20 mL of n-hexane added. The solution was kept at 4° C. overnight. A formed solid (2.57 g, 78%) was filtered off and dried in a high vacuum; $R_f$ value 0.40 in DCM/MeOH 10:0.4. $^1$H NMR (DMSO-d$_6$, 500 MHz) δ: 11.41 (s, 1H, NH), 7.98 (s, 1H, H6-uridine), 6.22 (dd, H1', $^3J_{1',2'}$=6.45 Hz, $^3J_{1',2''}$=4.60 Hz), 4.93-4.72 (m, 1H, H-3'), 4.51-4.36 (m, 3H, H5', OH), 4.27-4.18 (m, 1H, H4'), 2.84-2.76 (m, 2H, H2-Lev), 2.63-2.55 (m, 2H, H3-Lev), 2.51-2.38 (m, 1H, H2'), 2.33-2.19 (m, 2H, H2"), 2.17 (s, 1H, H5-Lev) ppm.

5-Iodo-5'-O-(3-N-Boc-aminopropionyl)-3'-O-levulinyl-2'-deoxyuridine

A solution of 5-iodo-3'-O-levulinyl-2'-deoxyuridine (3) (2.20 g, 4.87 mmol), Boc-β-alanine (1.10 g, 5.84 mmol), DCC (1.26 g, 6.08 mmol) and DMAP (0.149 g, 1.22 mmol) in DCM/DMF (30/5 mL) was stirred at room temperature overnight. The reaction mixture was filtered and the solvent evaporated under reduced pressure. To the remaining residue, EtOAc (80 mL) was added and the mixture filtered again, washed with the solution of citric acid, $NaHCO_3$, brine, dried over $MgSO_4$, and evaporated. A crude product was separated and purified by column chromatography on a silica gel (DCM/MeOH, 10/0.4) to yield 2.15 g (71%) of the title compound; $R_f$ value 0.47 in DCM/MeOH 10:0.5. $^1$H NMR ($CDCl_3$, 500 MHz) δ: 11.12 (s, 1H, NH), 8.62 (t, 1H, NH, J=4.5 Hz), 7.94 (s, 1H, H6-uridine), 6.18 (t, 1H, H1', J=5.54 Hz), 4.62-4.53 (m, 1H, H3'), 4.34-4.27 (m, 1H, H4'), 3.75-3.55 (m, 4H, H5', H3-Prop), 2.85-2.74 (m, 4H, H2-Prop, H3-Lev), 2.65-2.58 (m, 2H, H2-Lev), 2.52-2.43 (m, 1H, H2'), 2.28-2.17 (m, 1H, H2"), 2.19 (s, 3H, H5-Lev), 1.45 (s, 9H, H3-Boc) ppm.

The Boc protecting group of the 5-iodo-5'-O-(6-N-Boc-aminopropionyl)-3'-O-levulinyl-2'-deoxyuridine (1.51 g, 2.42 mmol) was cleaved in MeCN (22 mL) containing 3.5 mL of TFA and the separated TFA salt was reacted immediately with 0.95 g (2.45 mmol) of N,N'-bis(tert-butoxycarbonyl)-N"-trifluoro-methanesulfonyl guanidine in the presence of TEA (720 µL) as described in General Procedure A. The residue was purified by chromatography on a silica gel column using a gradient of MeOH in DCM (0.3-0.5:10) to give 1.57 g (74%) of the product ($R_f$ value 0.67 in DCM/MeOH 10:0.3). The 3'-O-Lev group was cleaved with a mixture of $N_2H_4.H_2O$/pyridine/AcOH (0.3/9.5/2.4 mL) and a crude product purified again on a silica gel column (DCM/MeOH, 10:0.35), to give 1.01 g (73% yield) of 14a as colorless foam; $R_f$ value 0.60 (DCM/MeOH, 10:0.5).

HPLC Analysis of 5-Iodo-5'-O—[N,N'-bis(tert-(butyloxycarbonyl)-N"-propionyl)-guanidino]-2'-deoxyuridine (14a)

HPLC analysis: 1) $t_R$=35.6 min (≥98.81% pure at 280 nm) on Columbus C18 100 Å, (5 µm, 4.6×250 mm) column, eluent: solvent A water, solvent B $CH_3CN$; eluted at the rate of 0.8 mL/min with a linear gradient of B from 10 to 90% over 40 min, 90-95% within 40-45 min and 95% B kept over 15 min. On ACE C18 100 Å, (5 µm, 4.6×250 mm) column; 2) $t_R$=34.5 min, (≥98.35% pure at 220 nm); eluent: solvent A water, solvent B $CH_3CN$; eluted at the rate of 0.8 mL/min with a linear gradient of B from 40 to 80% over 65 min, then 95% of B kept over 25 min. $^1$H NMR ($CDCl_3$, 500 MHz) δ: 11.46 (s, 1H, NH-uridine), 8.71 (bs, 1H, NH), 8.66 (t, 1H, NH, J=4.52 Hz), 7.96 (s, 1H, H6-uridine), 6.21 (t, 1H, H1', J=5.55 Hz), 4.48-4.42 (m, 2H, H3', OH), 4.37-4.31 (m, 1H, H4'), 3.75-3.53 (m, 4H, H5', H2-Prop), 2.85-2.74 (m, 2H, H3-Prop), 2.58-2.48 (m, 1H, H2'), 2.24-2.19 (m, 1H, H2"), 1.49 (s, 9H, H3-BocN'), 1.46 (s, 9H, H3-BocN") ppm. $^{13}$C NMR ($CDCl_3$, 100 MHz) δ: 171.71 (C1-Prop), 163.33 (C4), 160.01 (C1-Boc-N'), 156.18 (C1-Boc-N"), 153.88 (C2), 149.95 (C-guanidine), 143.44 (C6), 111.67 (C5), 85.74 (C1'), 84.29 (C4'), 77.23 (C2-Boc-N'), 77.12 (C2-Boc-N"), 74.34 (C3'), 67.52 (C5'), 44.20 (C2-Prop), 42.37 (C3-Prop), 38.74 (C2'), 28.26 (C3-Boc-N'), 28.05 (C3-Boc-N") ppm.

HPLC Purification and Analysis of 5-Trimethylstannyl-5'-O—[(N,N'-bis(tert-(butyloxycarbonyl)-N"-propionyl)guanidino]-2'-deoxyuridine (15a)

General Procedure B was carried out with 336 mg (0.504 mmol) of 5-Iodo-5'-O—[(N,N'-bis(tert-(butyloxycarbonyl)-N"-propionyl)guanidino]-2'-deoxyuridine (14a) in EtOAc containing TEA (300 µL, 2.15 mmol) in the presence of the palladium catalyst (35 mg, 0.05 mmol). A crude product was initially purified on a silica gel column (EtOAc/n-hexanes, 3:1) to give this stannane as colorless foam in 41% yield, $R_f$ value 0.69 (DCM/MeOH, 10:0.5) but the product was only ~91.3% pure by HPLC analysis (at 254/280 nm), eluent: solvent A water, solvent B $CH_3CN$; eluted at the rate of 0.8 mL/min with a linear gradient of B from 10 to 90% over 40 min, then 90-95% within 40-45 min, and then 95% of B kept over 25 min. Further HPLC purification (177 mg, ~8 mg per injection) was performed on a Columbus C18, 100 Å, (5 µm, 10×250 mm) column eluted with a solution of 65% MeCN in water for 28 min, then with a linear gradient of MeCN from 65 to 95% over 7 min and 95% MeCN for a further 25 min, at the rate of 2.4 mL/min. Subsequent HPLC analysis (ACE 100 Å, 5 µm, 4.6×250 mm) confirmed high (99.6% purity at 220/280 nm) of a final product: $t_R$=40.85 min, eluent; solvent A water, solvent B $CH_3CN$; eluted with a linear gradient of B from 5 to 95% over 45 min and then 95% B for 15 min, at the rate of 0.8 mL/min. $^1$H NMR ($CDCl_3$, 500 MHz) δ: 11.51 (s, 1H, NH-uridine), 8.64 (bs, 1H, NH), 8.49 (t, 1H, NH, J=5.50 Hz), 7.16 (s, 1H, H6-uridine, $^3J_{Sn,H}$=18.6 Hz), 6.19 (t, 1H, H1', J=6.56 Hz), 4.49-4.38 (m, 2H, H3', OH), 4.34-4.29 (m, 1H, H4'), 4.07-3.78 (m, 2H, H5'), 3.26-3.14 (m, 2H, H3-Prop), 2.68-2.57 (m, 2H, H2-Prop), 2.46-2.40 (m, 1H, H2'), 2.27-2.18 (m, 1H, H2"), 1.50 (s, 9H, H3-BocN'), 1.49 (s, 9H, H3-BocN"), 0.28 (s, 9H, 3×$SnCH_3$, $^2J_{Sn,H}$=27.9 Hz) ppm. $^{13}$C NMR ($CDCl_3$, 100 MHz) δ: 171.71 (C1-Prop), 166.07 (C4), 163.42 (C-guanidine), 156.14 (C1-Boc-N'), 153.17 (C1-Boc-N"), 150.86 (C2), 143.41 (C6), 113.33 (C5), 86.20 (C1'), 84.03 (C4',), 83.40 (C2-Boc-N'), 79.51 (C2-Boc-N"), 71.62 (C3'), 64.02 (C5'), 39.96 (C2'), 36.05 (C3-Prop), 33.97 (C2-Prop), 28.27 (C3-Boc-N'), 28.06 (C3-Boc-N"), −9.28 (3×$CH_3$—Sn) ppm. $^{119}$Sn NMR ($CDCl_3$, 100 MHz) δ: −1.47 ppm.

Purified, anhydrous samples of (15a) (~100 µg each) were stored for extended period of time (up to six months) with the exclusion of the light, under nitrogen at −20° C. and were suitable for instantaneous radioiodinations.

5-[$^{125}$I]-Iodo-5'-O—[(N,N'-bis(tert-(butyloxycarbonyl)-N"-propionyl)guanidino]-2'-deoxyuridine (16a Radioiodination (General Procedure C) of stannane (15a) (~100 µg) was done twice, with 40.1 and 34.4 MBq of $Na^{125}I$/NaOH, to give overall 67.8 MBq of (16a). An average yield of the isolated product was 91%. The reaction mixture was separated and purified by HPLC using Columbus C18 100 Å (5 µm, 4.6×250 mm) column, eluted at the rate of 0.8 mL/min with a linear gradient of MeCN in water from 0-95% over 60 min, then 95% MeCN was held further 30 min. The product was collected in three fractions (within 39-41 min after the injection) and an excess of unreacted stannane (15a) was sufficiently separated, eluting ~4.5 min later. HPLC analysis: $t_R$=39.95 min, (≥98% radiochemical purity, Bioscan NI(T)/UV 280 nm).

Removal of Boc Protecting Groups of 5-[$^{125}$I]-
Iodo-5'-O—[(N,N'-bis(tert-(butyloxycarbonyl)-N"-
propionyl)guanidino]-2'-deoxyuridine (16a).
5-[$^{125}$I]-Iodo-5'-O-propionylguanidino-2'-deoxyuridine (17a)

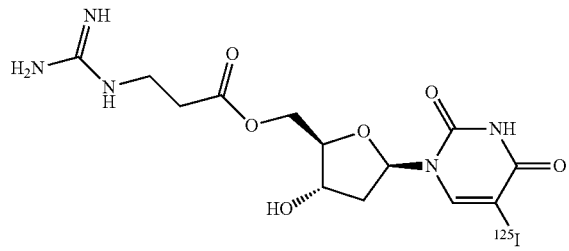

[17a]

The cleavage process of N-Boc guanidine protecting groups of (16a) was conducted initially (monitored by HPLC) in a solution of (16a) (~3.7 MBq in 500 μL of 40% TFA/MeCN) at room temperature and required ~190 min. To complete the N-Boc cleavage faster (General Procedure C), to a dried residue of (16a) (31.45 MBq) under nitrogen, TFA (30 μL) was added, and the solution was kept in a tightly covered vial at 75° C. for 20 min. An average yield of the purified (17a) was 83%. The product (26.1 MBq) was separated on Columbus C18 100 Å (5 μm, 4.6×250 mm) column, eluted at 0.8 mL/min with a linear gradient of MeCN in water from 0 to 95% over 60 min and 95% MeCN held 10 min longer. Both solvents contained 0.07% TFA (v/v); $t_R$ 21.2 min (≥98% radiochemical purity, Bioscan NI/UV 280 nm). The product eluting within 20.8-22.0 min after the injection was collected in three fractions, which were combined and evaporated. To the portion of the product dry residue (17.95 MBq) ethanol (80 μL) was added, followed by potassium phosphate buffer (100 μL, 100 mM, pH 6.1). The resulted solution was injected again on HPLC system equipped with Luna CN (5μ, 4.5×250 mm) column eluted at the rate of 0.8 mL/min with 15% EtOH in potassium phosphate buffer (100 mM PB, pH 6.1) for a period of 10 min and then with a linear gradient of EtOH in PB, from 15 to 70% over 30 min. The product (16.1 MBq, 89%) was collected within 16.5-20.5 min after the injection ($t_R$=16.8 min, ≥97% radiochemical purity Bioscan NI(T)/UV 280 nm).

Stability of 5-[$^{125}$I]-Iodo-3'-O-(hexanoylguanidino)-2'-deoxyuridine (17a)

Incubations: into a solution (1980 μL) of serum (mouse, human), buffer or cells media, a sample of (17a), (185-390 kBq) in 15-20 μL of 25% EtOH/PB (100 mM, pH 6.1) was added; the resulting mixture was briefly vortexed and kept (up to 24 h) at ambient temperature or inside the incubator (37° C./~5% $CO_2$). At each time point, a volume of 1 mL was withdrawn, the extract of sample prepared and analyzed by HPLC.

Preparation of extracts: a sample (1 mL) from each incubated mixture with compound (17a) was treated with MeCN (1 mL), vortexed, and centrifuged (2,000 rpm, 15 min). The supernatant was removed and the radioactivity measured. Aliquots of supernatant (250-500 μL) were acidified to pH~6 with 0.05 N TFA (2-8 μL). The excess of MeCN was evaporated with a stream of nitrogen and water (100 μL) added. A mixture was passed through a 0.2μ filter and each sample (~100 μL, 95-185 kBq) injected on HPLC system.

HPLC analysis of extracts: continued on Columbus C18 100 Å (5 μm, 4.6×250 mm) column; eluted at 0.8 mL/min with a linear gradient of MeCN from 0 to 95% over 60 min and 95% MeCN was kept for a period of further 20 min, detecting the radioactivity (Bioscan NaI(T)). Both solvents contained 0.07% TFA (v/v).

The stability of 17a in mouse and human serum was limited. The results obtained after incubations in human serum and cells media at room temperature are depicted in FIGS. 7A-7D.

5-Iodo-5'-O—[(N,N'-bis(tert-(butyloxycarbonyl)-N"-hexanoyl)-guanidino]-2'-deoxyuridine (14b)

As in the previous preparation of (14a), the synthesis of (14b), began with 5-iodo-3'-O-levulinyl-2'-deoxyuridine (3), obtained via esterification of 4-oxopentanoic acid with 5-iodo-5'-O-trityl-2'-deoxyuridine, using the DCC/DMAP activation method, and the subsequent trityl group cleavage by $ZrCl_4$ in $CH_3CN$. The 3'-O-protected uridine (3) was then reacted with 6-(Boc-amino)caproic acid (DCC/DMPA activation) to yield 5-iodo-5'-O-(6-N-Boc-aminohexanonyl)-3'-O-levulinyl-2'-deoxyuridine, which after elimination of the N-Boc protecting group in ~15% TFA/MeCN, the following guanidinylation with N,N'-bis(tert-butyloxycarbonyl)-N"-trifluoro-methane-sulfonyl guanidine, and the final deprotection of 3'-O-Lev group, produced the target guanidinoalkyl ester (14b) in 69% yield (further details below). The first two preliminary preparations were carried out as follows:

5-Iodo-3'-O-levulinyl-2'-deoxyuridine (3)

To a stirred solution of 5-iodo-5'-O-trityl-2'-deoxyuridine (5.02 g, 8.42 mmol) and levulinic acid (1.05 mL, 10.15 mmol) in 80 mL of DCM/DMF (200/1, v/v), DCC (2.1 g, 10.17 mmol) and DMAP (260 mg, 2.13 mmol) were added. Upon completion of the reaction (~4 h, TLC monitoring), the mixture was filtered and the filtrate evaporated under reduced pressure. An oily residue was treated with EtOAc/hexanes (3/1, v/v), filtered again, evaporated and a crude product separated by chromatography on a silica gel column using a gradient of MeOH in DCM (0.2-0.4:10) to give 5.54 g (94%) of the 5-iodo-5'-O-trityl-3'-O-levulinyl-2'-deoxyuridine ($R_f$ value 0.65 in DCM/MeOH 10:0.4); 5.05 g (7.27 mmol) of which was dissolved in MeCN (60 mL) with stirring and $ZrCl_4$ (1.71 g, 7.29 mmol) added. Cleavage of trityl group was completed after ~1 h (TLC monitoring, EtOAc/MeOH, 10/0.1). The solvent was evaporated under reduced pressure, and to a solid residue, 100 mL of EtOAc and water (30 mL) were added. The organic phase was washed with brine and dried over $MgSO_4$. The solvent was partially evaporated (to 50 mL) and 20 mL of n-hexane added. The solution was kept at 4° C. overnight. A formed solid (2.57 g, 78%) was filtered off and dried in a high vacuum; $R_f$ value 0.40 in DCM/MeOH 10:0.4. $^1$H NMR (DMSO-$d_6$, 500 MHz) δ: 11.41 (s, 1H, NH), 7.98 (s, 1H, H6-uridine), 6.22 (dd, H1', $^3J_{1',2'}$=6.45 Hz, $^3J_{1',2''}$=4.60 Hz), 4.93-4.72 (m, 1H, H-3'), 4.51-4.36 (m, 3H, H5', OH), 4.27-4.18 (m, 1H, H4'), 2.84-2.76 (m, 2H, H2-Lev), 2.63-2.55 (m, 2H, H3-Lev), 2.51-2.38 (m, 1H, H2'), 2.33-2.19 (m, 2H, H2"), 2.17 (s, 1H, H5-Lev) ppm.

5-Iodo-5'-O-(3-N-Boc-aminohexanoyl)-3'-O-levulinyl-2'-deoxyuridine

A solution of 5-iodo-3'-O-levulinyl-2'-deoxyuridine (3) (3.21 g, 7.10 mmol), Boc-6-aminohexanoic acid (1.65 g, 7.13 mmol), DCC (1.54 g, 7.46 mmol) and DMAP (0.217 g, 1.78 mmol) in DCM/DMF (30/0.8 mL) was stirred at room temperature overnight. The reaction mixture was filtered and the solvent evaporated under reduced pressure. To the remaining residue, EtOAc (80 mL) was added and the mixture filtered again, washed with the solution of citric acid, NaHCO$_3$, brine, dried over MgSO$_4$, and evaporated. A crude product was separated and purified by column chromatography on a silica gel (EtOAc/n-hexane, 2/1) to yield 3.26 g (83%) of the expected compound; R$_f$ value 0.56 in DCM/MeOH 10:0.5. $^1$H NMR (CDCl$_3$, 500 MHz) δ: 10.84 (s, 1H, NH), 8.55 (t, 1H, NH, J=4.4 Hz), 8.11 (s, 1H, H6-uridine), 6.14 (t, 1H, H1', J=5.5 Hz), 5.22-5.18 (m, 1H, H3'), 4.08-3.98 (m, 1H, H4'), 3.68-3.59 (m, 4H, H5', H6-Hex), 2.84-2.76 (m, 2H, H3-Lev), 2.67-2.60 (m, 2H, H2-Lev), 2.54-2.47 (m, 1H, H2'), 2.38-2.27 (m, 3H, H2", H2-Hex), 2.15 (s, 3H, H5-Lev), 1.64-1.56 (m, 2H, H3-Hex), 1.54-1.50 (m, 2H, H5-Hex), 1.44 (s, 9H, H3-Boc), 1.37-1.28 (m, 2H, H4-Hex) ppm.

General Procedure A was implemented, starting with 5-iodo-5'-O-(6-N-Boc-aminohexanoyl)-3'-levulinyl-2'-deoxyuridine (2.25 g, 3.38 mmol). The Boc protecting group was cleaved and the separated TFA salt was reacted without delay with 1.36 g (3.47 mmol) of N,N'-bis(tert-butoxycarbonyl)-N"-trifluoromethanesulfonyl guanidine in presence of TEA (970 µL, 695 mmol). The product residue dissolved in 60 mL of EtOAc was washed with solution of citric acid and brine, organic phase was dried over MgSO4, evaporated, and the residue purified on silica gel column (EtOAc/n-hexane, 2:1). The 3'-O-Lev group was cleaved with a mixture of N2H4.H2O (0.5 M, 0.26 mL) in pyridine/AcOH (4:1, 5 mL) and a crude product was purified again on a silica gel column (DCM/MeOH, 10:0.6) to give 1.65 g (69% overall yield) of (14b) as colorless foam, Rf value 0.35 (DCM/MeOH, 10:0.6) and was 93.7% pure by HPLC analysis (at 254/280 nm). Further HPLC purification of this product (106 mg, ~5 mg per injection) was performed on a Columbus C18, 100 Å, (5 µm, 10×250 mm) column eluted with a linear gradient of MeCN in water from 50 to 95% over 30 min at the rate of 2.7 mL/min. Subsequent HPLC analysis on ACE C18 100 Å, (5 µm, 4.6×250 mm) column, confirmed an acceptable purity (≥95.4% at 280 nm) of a final product: tR=40.6 min, eluent: solvent A 10% CH3CN in water, solvent B CH3CN; run with a linear gradient of B from 10 to 95% over 45 min, then 95% B for 25 min, elution rate 0.8 mL/min. 1H NMR (CDCl3, 500 MHz) δ: 11.48 (s, 1H, NH-uridine), 8.45 (bs, 1H, NH), 8.29 (t, 1H, NH, J=4.54 Hz), 7.95 (s, 1H, H6-uridine), 6.23 (t, 1H, H1', J=5.50 Hz), 4.47-4.39 (m, 2H, H3', OH), 4.30-4.18 (m, 1H, H4'), 3.42-3.38 (m, 2H, H5'), 2.85-2.74 (m, 2H, H2-Hex), 2.54-2.47 (m, 3H, H2', H6-Hex), 2.20-2.15 (m, 1H, H2"), 1.75-1.69 (m, 2H, H3-Hex), 1.63-1.58 (m, 2H, H5-Hex), 1.51 (s, 9H, H3-BocN'), 1.49 (s, 9H, H3-BocN"), 1.44-1.36 (m, 2H, H4-Hex) ppm. 13C NMR (CDCl3, 100 MHz) δ: 173.13 (C1-Hex), 163.46 (C4), 159.65 (C1-Boc-N'), 156.16 (C1-Boc-N"), 153.34 (C2), 149.62 (C-guanidine), 144.18 (C6), 111.67 (C5), 85.83 (C1'), 84.54 (C4'), 81.03 (C2-Boc-N'), 79.50 (C2-Boc-N"), 70.87 (C3'), 68.41 (C5'), 41.14 (C2-hex), 40.64 (C6-Hex), 38.74 (C2'), 31.21 (C5-Hex), 28.29 (C3-Boc-N'), 28.08 (C3-Boc-N"), 26.28 (C4-Hex), 24.53 (C3-Hex) ppm.

5-Trimethylstannyl 5'-O—[(N,N'-bis(tert-(butyloxycarbonyl)-N"-hexanoyl)-guanidino]-2'-deoxyuridine (15b)

Stannylation of the iodide (14b) (0.386 g, 0.54 mmol) was conducted with hexamethylditin 267 mg (0.820 mmol) in the presence of the palladium catalyst (38 mg, 0.05 mmol) and TEA (150 µL, ~1.0 mmol) in EtOAc (15 mL). A crude product was purified on a silica gel column using EtOAc/n-hexanes (2:1) to give 134 mg of (15b) in 29% yield as yellow foam, R$_f$ value 0.56 (DCM/MeOH, 10:0.4) and was 91.4% pure by HPLC analysis (at 220/280 nm). Further HPLC purification of this product (96 mg, ~4 mg per injection) was performed on a Columbus C18, 100 Å, (5 µm, 10×250 mm) semi preparative column, eluted with a solution of 65% MeCN in water for 25 min, followed by a linear gradient of MeCN from 65 to 95% over 15 min and finally, 95% MeCN for the last 15 min, at the rate of 2.5 mL/min. Subsequent HPLC analysis confirmed its high purity: t$_R$=31.1 min (≥98.2% pure, UV at 220/280 nm); ACE 100 Å, 5 µm, 4.6×250 mm), eluted at the rate of 0.8 mL/min with a linear gradient of MeCN in water, from 40 to 95% over 40 min and 95% for 15 min. $^1$H NMR (DMSO-d$_6$, 500 MHz) δ: 11.16 (s, 1H, NH-uridine), 8.44 (bs, 1H, NH), 8.14 (t, 1H, NH, J=5.50 Hz), 7.81 (s, 1H, H6-uridine, $^3$J$_{Sn,H}$=19.4 Hz), 6.32 (dd, 1H, H1', $^3$J$_{1',2'}$=6.45 Hz, $^3$J$_{1',2"}$=4.64 Hz), 4.92-4.84 (m, 1H, H4'), 4.35-4.12 (m, 2H H5'), 3.59-3.54 (m, 3H, H3',OH), 2.87-2.74 (m, 2H, H6-Hex), 2.39-2.32 (m, 3H, H2', H2-Hex), 2.18-2.09 (m, 1H, H2"), 1.74-1.66 (m, 2H, H3-Hex), 1.57-1.51 (m, 2H, H5-Hex), 1.40 (s, 9H, H3-BocN'), 1.38 (s, 9H, H3-BocN"), 1.33-1.26 (m, 2H, H4-Hex), 0.29 (s, 9H, 3×SnCH$_3$, $^2$J$_{Sn,H}$=29.8 Hz) ppm. $^{13}$C NMR (DMSO-d$_6$, 100 MHz) δ: 173.42 (C1-Hex), 163.55 (C4), 158.88 (C1-Boc-N'), 156.49 (C1-Boc-N"), 152.71 (C2), 149.77 (C-guanidine), 143.23 (C6), 110.37 (C5), 87.32 (C1'), 85.17 (C4'), 83.55 (C2-Boc-N'), 79.73 (C2-Boc-N"), 71.27 (C3'), 62.29 (C5'), 41.96 (C6-hex), 40.51 (C2-Hex), 38.58 (C2'), 30.34 (C5-Hex), 28.57 (C3-Boc-N'), 27.32 (C3-Boc-N"), 26.12 (C4-Hex), 24.33 (C3-Hex), -7.34 (3×CH$_3$—Sn) ppm. $^{119}$Sn NMR (CDCl$_3$, 100 MHz) δ: -1.84 ppm.

5-[$^{125}$I]-Iodo-5'-O—[(N,N'-bis(tert-(butyloxycarbonyl)-N"-hexanoyl)-guanidino]-2'-deoxyuridine (16b)

Radioiodination (General Procedure C) of stannane (15b) (~100 µg) was completed with ~34.1 MBq of Na$^{125}$I/NaOH, ending overall with 28.3 MBq of the isolated product, in 83% yield. The reaction mixture was separated and purified by HPLC on Jupiter C18 100 Å (5 µm, 4.6×250 mm) column, eluted at the rate of 0.8 mL/min with a linear gradient of MeCN in water from 40-95% over 40 min, then 95% MeCN was held additional 20 min. The product was collected in two fractions (within 25.1-26.5 min after the injection) and an excess of unreacted tin precursor was fully separated, eluting ~4.5 min later. Further HPLC analysis of the product confirmed its high purity: t$_R$=36.4 min, (≥98% radiochemical purity, Bioscan NI(T)/UV 280 nm), C18 100 Å (5 µm, 4.6×250 mm) column, eluted at 0.8 mL/min with a linear gradient of MeCN in water (0-95% over 50 min, then 95% MeCN was held further 10 min).

Cleavage of Boc Protecting Groups of 5-[$^{125}$I]-Iodo-5'-O—[(N,N'-bis(tert-(butyloxycarbonyl)-N"-hexanoyl)guanidino]-2'-deoxyuridine (16b)

The cleavage progress of N-Boc guanidine protecting groups of (16b) was examined at room temperature. From a solution of (16b) (~3.7 MBq in 500 µL of 40% TFA/MeCN), 10 µL samples (~74 kBq) were injected periodically on the HPLC system. The deprotection progress was monitored on HPLC (Bioscan NaI(T) detector), using Columbus C18 100 Å (5 µm, 4.6×250 mm) column, eluted at 0.8 mL/min with a linear gradient of MeCN in water (0-95% over 60 min). Both solvents contained 0.07% TFA (v/v). Deprotection was completed within ~196 min.

5-[$^{125}$I]-Iodo-5'-O-hexanoylguanidino-2'-deoxyuridine (17b)

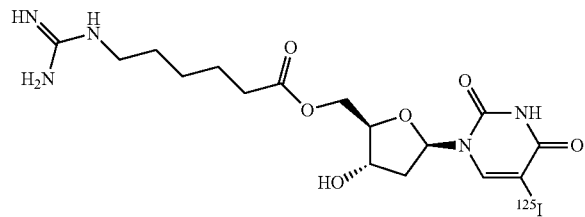

[17b]

The intermediate separation of Boc-protected product (16b) was omitted. The standard radioiodination (General Procedure C) of stannane (15b) (~100 µg) carried out three times with 30.7, 47.5 and 50.5 MBq of Na$^{125}$I/NaOH, gave overall 87.5 MBq of (17b) in an average yield of 68%. The crude reaction mixtures, quenched with a solution of Na$_2$S$_2$O$_3$, were evaporated with a stream of dried nitrogen, kept under high vacuum, and to the resulting dried residues, TFA (100 µL) was added and the mixtures heated in a sealed vial at 70° C. for ~25 min. After cooling, the mixtures were diluted with CH$_3$CN (200 µL) and evaporated with a stream of nitrogen, leaving ~20 µL of the liquid in the reaction vial. To the tube containing the reaction mixture residue, ethanol (80 µL) was added followed by potassium phosphate buffer (100 µL, 100 mM PB, pH 6.1), and the resulting mixture was injected on HPLC reverse phase column eluted with a linear gradient of EtOH in potassium phosphate buffer. The reaction mixture was separated and purified by HPLC on Luna CN 100 Å (5 µm, 4.6×250 mm) column eluted at the rate of 0.8 mL/min, with a linear gradient of EtOH in potassium phosphate buffer (100 mM PB, pH 6.1) from 15 to 70% over 60 min, then 70% EtOH in PB was kept for further 10 min. The product was collected within 17.5-20.5 min after the injection. The HPLC analysis of the product (17b) (t$_R$=20.1 min) showed its satisfactory ≥98% radiochemical purity (Bioscan NI(T)/UV 280 nm), Luna CN 100 Å (5 µm, 4.6×250 mm) column eluted at the rate of 0.8 mL/min, with a linear gradient of EtOH in potassium phosphate buffer (100 mM PB, pH 6.1) from 15 to 70% over 60 min, then 70% EtOH in PB was kept for further 10 min.

Additional HPLC analysis showed (t$_R$=23.8 min) and satisfactory ≥98% radiochemical purity (Bioscan NI(T)/UV 280 nm) Columbus C18 (5 µm, 4.5×250 mm) column eluted at the rate of 0.8 mL/min, with a linear gradient of MeCN from 0 to 95% over 50 min, then 95% MeCN for an additional 10 min, both solvents contained 0.07% TFA (v/v).

Stability Evaluation of 5-[$^{125}$I]-Iodo-5'-O-hexanoylguanidino-2'-deoxyuridine (17b)

Incubations: into a solution (1980 µL) of serum (mouse, human), buffer or cells media, a sample of (17b), (259-370 kBq) in 15-20 µL of 25% EtOH/PB (100 mM, pH 6.1) was added; the resulted mixture was briefly vortexed and kept (up to 24 h) at ambient temperature or inside the incubator (37° C., ~5% CO$_2$). At each time point, a volume of 1 mL was withdrawn, the extract of sample prepared and analyzed by HPLC.

Preparation of extracts: a sample (1 mL) from each incubated mixture with compound (17b) was treated with MeCN (1 mL), vortexed, and centrifuged (2,000 rpm, 15 min). The supernatant was removed and the radioactivity measured. Aliquots of supernatant (250-500 µL) were acidified to pH~6 with 0.05 N TFA (2-8 µL). The excess of MeCN was evaporated with a stream of nitrogen and water (100 µL) added. A mixture was passed through a 0.2µ filter and each sample (~100 µL, 111-185 kBq) injected on HPLC system.

HPLC analysis of extracts: proceeded on Columbus C18 100 Å (5 µm, 4.6×250 mm) column; eluted at 0.8 mL/min with a linear gradient of MeCN from 0 to 95% over 50 min and 95% MeCN was kept for a period of further 20 min, detecting the radioactivity (Bioscan NaI(T)). Both solvents contained 0.07% TFA (v/v). The selected analyses are depicted in FIGS. 8A-8M.

5-Iodo-5'-O-[cyclo-3,5-di(tert-butyl)-6-fluorosaligenyl]-3'-O—[(N,N'-bis(tert-(butyloxycarbonyl)-N''-hexanoyl)guanidino]-2'-deoxyuridine Monophosphate (18)

In the preparation of (18), the required starting 5-iodo-5'-O-[cyclo-3,5-di(tert-butyl)-6-fluorosaligenyl]-2'-deoxyuridine monophosphate, was attained via phosphorus(III) route in two steps: the 5-iodo-3'-levulinyl-2'-deoxyuridine was first coupled with cyclo-3,5-di(tert-butyl)-6-fluoro chlorophosphite in the presence of N,N-diisopropylethylamine, and the generated phosphite was directly oxidized with tert-butyl hydroperoxide to give the expected cyclosaligenyl product, which after deprotection (a cleavage of 3'-O-Lev group) was reacted with 6-(Boc-amino)caproic acid, using DCC/DMPA activation, to yield 5-iodo-5'-O-[cyclo-3,5-di(tert-butyl)-6-fluorosaligenyl]-3'-O-(6-N-Boc-amino-hexanonyl)-2'-deoxyuridine mono-phosphate. The subsequent elimination of the N-Boc protecting group in ~15% TFA/MeCN and the following guanidinylation with N,N'-bis(tert-butyloxycarbonyl)-N'''-trifluoro-methane-sulfonyl guanidine led to the target guanidinoalkyl ester (18) in 79% yield (further details are below).

To prepare 5-iodo-5'-O-[cyclo-3,5-di(tert-butyl)-6-fluoro-saligenyl]-3'-O-(6-N-Boc-aminohexanonyl)-2'-deoxyuridine monophosphate, a solution of 5-iodo-5'-O-[cyclo-3,5-di(tert-butyl)-6-fluorosaligenyl]-2'-deoxyuridine monophosphate (1.30 g, 2.0 mmol), Boc-6-amino-hexanoic acid (0.49 g, 2.12 mmol), DCC (0.45 g, 2.18 mmol) and DMAP (0.065 g, 0.53 mmol) in Et$_2$O/DCM (40/2 mL) was stirred at room temperature for 3 h (TLC monitoring). The reaction mixture was filtered and the solvent evaporated under reduced pressure. To the remaining residue, EtOAc/n-hexane (80/20 mL) was added and the mixture filtered again, then washed with the solution of citric acid, NaHCO$_3$, brine, dried over MgSO$_4$, and evaporated. A crude product was separated and purified by column chromatography on a silica gel (DCM/MeOH, 10/0.6) to yield 1.67 g (97%) of the product; R$_f$ value 0.64 in DCM/MeOH 10:0.5. As expected, the HPLC and NMR analysis revealed the mixture of diastereomers. HPLC: t$_{R1}$=27.63 and t$_{R2}$=27.95 min, (≥96% pure, UV at 280 nm) on ACE C18 column 100 Å (5 µm, 4.6×250 mm); eluted at the rate of 0.8 mL/min with a linear gradient of MeCN in water, from 50 to 95% MeCN over 30 min, then 95% B kept for 30 min. $^1$H NMR (DMSO-d$_6$, 500 MHz) δ: 11.19, 11.12 (2 s, 1H, HN-6 uridine), 8.24 (bs, 1H, NH), 7.46, 7.42 (2s, 1H, H6-uridine), 7.33-7.23 (m, 1H, aryl-H4), 6.06-5.87 (m, 1H, H1'), 5.35-5.31 (m, 2H, benzyl), 4.65-4.36 (m, 2H, H3', H4'), 3.75-3.68 (m, 2H, H5'), 3.30-3.26 (m, 2H, H2-Hex), 2.64-2.34 (m, 3H, H2', H6-Hex), 2.29-2.21 (m, 1H, H2''), 1.70-1.67 (m, 2H, H3-Hex), 1.57-1.52 (m, 2H, H5-Hex), 1.42 (s, 9H, H3-BocN''), 1.38 (s, 9H, 3×CH₃-t-Bu'), 1.34-1.29 (s, 9H, 3×CH₃-t-Bu; m, 2H, H4-Hex) ppm.

General Procedure A was carried out with the 5-iodo-5'-O-[cyclo-3,5-di(tert-butyl)-6-fluorosaligenyl]-3'-O-(6-N-Boc-aminohexanoyl)-2'-deoxyuridine monophosphate (1.20 g, 1.39 mmol), the Boc protecting group was cleaved, and the separated TFA salt reacted directly with 0.60 g (1.53 mmol) of N,N'-bis(tert-butoxycarbonyl)-N''-trifluoromethanesulfonyl guanidine in DCM (35 mL) in the presence of Et₃N (390 μL, 2.80 mmol). A crude product, purified twice on a silica gel column (DCM/MeOH, 10:0.3-0.5), was obtained as colorless rigid foam: 1.11 g (79% yield), $R_f$ value 0.52 (DCM/MeOH, 10:0.5). The HPLC analysis showed a mixture of diastereomers: $t_{R1}$=42.74 and $t_{R2}$=43.40 min (≥96% pure, UV at 254/280 nm); ACE C18 column 100 Å (5 μm, 4.6×250 mm); eluted at the rate of 0.8 mL/min with a linear gradient of MeCN in water, from 70 to 95% MeCN over 60 min, then 95% kept for 30 min. ¹H NMR (DMSO-d₆, 500 MHz) δ: 11.39, 11.31 (2s, 1H, NH-uridine), 8.56 (bs, 1H, NH), 8.23 (t, 1H, NH, J=4.4 Hz), 7.96, 7.94 (2s, 1H, H6-uridine), 7.30-7.24 (m, 1H, aryl-H4), 6.26-6.20 (m, 1H, H1'), 5.54-5.37 (m, 2H, benzyl), 4.45-4.21 (m, 2H, H3', H4'), 3.55-3.41 (m, 2H, H5'), 2.90-2.82 (m, 2H, H2-Hex), 2.44-2.34 (m, 3H, H2', H6-Hex), 2.22-2.16 (m, 1H, H2''), 1.76-1.68 (m, 2H, H3-Hex), 1.64-1.57 (m, 2H, H5-Hex), 1.54 (s, 9H, H3-BocN'), 1.49 (s, 9H, H3-BocN''), 1.46 (s, 9H, 3×CH₃-t-Bu), 1.39-1.36 (s, 9H, 3×CH₃-t-Bu; m, 2H, H4-Hex) ppm. ¹³C NMR (DMSO-d₆, 100 MHz) δ: 173.18 (C1-Hex), 163.37 (C4), 160.15 (C1-Boc-N'), 158.29 (C1-Boc-N''), 155.33 (C6-aryl), 154.16 (C2), 149.62 (C-guanidine), 148.56 (C2-aryl), 144.18 (C6), 133.42 (C5-aryl), 130.48 (C3-aryl), 127.17 (C4-aryl), 111.67 (C5), 110.62 (C1-aryl), 88.65 (C1'), 84.56, (C4'), 81.56 (C2-Boc-N'), 80.10 (C2-Boc-N''), 71.22 (C3'), 69.34 (C-benzyl), 68.41 (C5'), 41.35 (C2-Hex), 40.82 (C6-Hex), 38.91 (C2'), 34.64, 34.57 (2×C2 t-Bu), 31.21 (C5-Hex), 29.91, 29.87 (CH₃-t-Bu), 28.29 (C3-Boc-N'), 28.08 (C3-Boc-N''), 26.28 (C4-Hex), 24.53 (C3-Hex) ppm. ³¹P NMR (DMSO-d₆) δ: −8.69, −8.89 (2s, diastereomers) ppm.

5-Trimethylstannyl-5'-O-[cyclo-3,5-di(tert-butyl)-6-fluorosaligenyl]-3'-O—[(N,N'-bis(tert-(butyloxycarbonyl)-N''-hexanoyl)guanidino]-2'-deoxyuridine Monophosphate (19)

The iodide (18) (1.26 g, 1.25 mmol) was reacted with hexamethylditin (0.69 g, 2.19 mmol) in the presence of the palladium catalyst (90 mg, 0.13 mmol) and TEA (950 μL, 6.82 mmol) in C₆H₆ (32 mL). A crude product purified twice on a silica gel column EtOAc/n-hexanes (1:1) was separated as yellow foam (390 mg, 30% yield), $R_f$ value 0.71 (DCM/MeOH, 10:0.5) and was ≥93.7% pure by HPLC analysis (at 220/280 nm). The following HPLC purification of this product (168 mg, ~11 mg per injection) was performed on a Columbus C18, 100 Å, (5 μm, 10×250 mm) semi preparative column, eluted with a linear gradient of MeCN in water, from 65 to 95% over 60 min at the rate of 2.4 mL/min. Following HPLC analysis confirmed acceptable purity of the product, a mixture of diastereomers: $t_{R1}$=57.8 and $t_{R2}$=58.17 min (≥98% pure, UV at 220/280 nm); ACE C18 column 100 Å (5 μm, 4.6×250 mm); eluted with a linear gradient of MeCN in water, from 70 to 95% MeCN over 60 min, then 95% B for 30 min, at the rate of 0.8 mL/min. ¹H NMR (DMSO-d₆, 500 MHz) δ: 11.27, 11.19 (2s, 1H, HN-uridine), 8.23 (bs, 1H, NH), 8.12 (t, 1H, NH, J=4.35 Hz), 7.79, 7.74 (2s, 1H, H6-uridine, $^3J_{Sn,H}$=19.47 Hz), 7.35-7.29 (m, 1H, aryl-H4), 5.91-5.84 (m, 1H, H1'), 5.44-5.39 (m, 2H, benzyl), 4.95-4.81 (m, 1H, H4'), 4.29-4.15 (m, 3H, H5', H3'), 2.90-2.84 (m, 2H, H6-Hex), 2.49-2.30 (m, 3H, H2', H2-Hex), 2.26-2.10 (m, 1H, H2''), 1.72-1.63 (m, 2H, H3-Hex), 1.61-1.55 (m, 2H, H5-Hex), 1.48 (s, 9H, H3-BocN'), 1.40 (s, 9H, H3-BocN''), 1.39 (s, 9H, 3×CH₃-t-Bu), 1.37-1.28 (s, 9H, 3×CH₃-t-Bu; m, 2H, H4-Hex), 0.29 (s, 9H, 3×CH₃—Sn, $^2J_{Sn,H}$=29.7 ppm. ¹³C NMR (DMSO-d₆, 100 MHz) δ: 173.45 (C1-Hex), 163.56 (C4), 160.32 (C1-Boc-N'), 158.63 (C1-Boc-N''), 155.83 (C2-aryl), 153.42 (C2), 149.81 (C-guanidine), 143.85 (C6-aryl), 143.32 (C6), 137.32 (C5-aryl), 130.54 (C3-aryl), 127.42 (C4-aryl), 111.22 (C5), 110.17 (C1-aryl), 89.45 (C1'), 85.24, (C4'), 82.57 (C2-Boc-N'), 79.84 (C2-Boc-N''), 73.72 (C3'), 68.44 (C-benzyl), 67.81 (C5'), 41.51 (C2-Hex), 40.72 (C6-Hex), 37.98 (C2'), 34.71, 34.57 (2×C1 t-Bu), 30.83 (C5-Hex), 29.90, 29.77 (C2 t-Bu), 28.87 (C3-Boc-N'), 28.45 (C3-Boc-N''), 26.57 (C4-Hex), 24.57 (C3-Hex), −7.62 (3×CH₃—Sn) ppm. ³¹P NMR (DMSO-d₆) δ: −8.73, −8.81 (2s, diastereomers) ppm.

5-[¹²⁵I]-Iodo-5'-O-[cyclo-3,5-di(tert-butyl)-6-fluorosaligenyl]-3'-O—[(N,N'-bis(tert-(butyloxycarbonyl)-N''-hexanoyl)guanidino]-2'-deoxyuridine Monophosphate (20)

Radioiodination (General Procedure C) of stannane (19) (~100 μg) was conducted twice with 59.2 and 42.6 MBq of Na¹²⁵I/NaOH and gave 89.6 MBq of (20) with an average yield of 88%. The reaction mixture was separated and purified by HPLC using ACE-100 C18 100 Å (5 μm, 4.6×250 mm) column, eluted at the rate of 0.8 mL/min with a linear gradient of MeCN in water, from 80-95% over 60 min, and 95% MeCN was held constant for an additional 30 min. The product was collected in three fractions (within 35-38 min after the injection). An excess of unreacted tin precursor (19) was separated sufficiently, eluting ~14.5 min later. The HPLC analysis of the product showed the diastereomeric mixture: $t_{R1}$=34.62 min, $t_{R2}$=35.35 min (≥98% radiochemical purity, Bioscan NI(T)/UV 280 nm).

5-[¹²⁵I]-Iodo-5'-O-[cyclo-3,5-di(tert-butyl)-6-fluorosaligenyl]-3'-O-hexanoylguanidino]-2'-deoxyuridine Monophosphate (21)

[21]

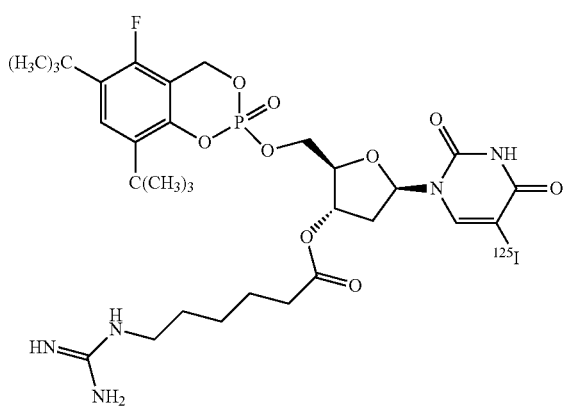

The removal of guanidine N-Boc protecting groups of compound (20) was tested initially in a solution of 50% TFA in MeCN at room temperature, and the reaction progress was monitored on HPLC (Bioscan NaI(T) detector), using ACE C18 100 Å (5 µm, 4.6×250 mm) column, eluted at 0.8 mL/min with a linear gradient of MeCN in water (0-95% over 60 min), with both solvents contained 0.07% TFA (v/v). The cleavage was completed after ~140 min (FIG. 9A-D).

To complete the N-Boc cleavage faster (General Procedure C), to a dried residue of 20 (three preparations conducted with: 24.15, 31.5 and 16.65 MBq) under nitrogen, TFA (40 µL) was added and the solution was kept in a tightly covered vial, at 75° C. for 20 min. An excess of TFA was evaporated with a stream of dry nitrogen. The product was separated on ACE-100 C18 100 Å (5 µm, 4.6×250 mm) column, eluted at 0.8 mL/min with a linear gradient of MeCN in water from 0 to 95% over 60 min and 95% MeCN was kept for an additional 10 min; both solvents contained 0.07% TFA (v/v). The product eluted within 43.2-44.5 min after the injection. An average yield of the purified (21) was 83%; diastereomeric mixture: $t_{R-1}$=42.1, $t_{R-2}$=42.4 min (≥98% radiochemical purity, Bioscan/UV 280 nm). To eliminate an excess of TFA, the solution containing the product was evaporated again, and to the dry residue of (21) (64.4 MBq), 80 µL of ethanol was added, followed by potassium phosphate buffer (100 µL, 100 mM, pH 6.1). The resulting solution was injected on HPLC system equipped with Luna CN (5µ, 4.5×250 mm) column and was eluted with: phosphate buffer (100 mM PB, pH 6.1) and EtOH; at the rate of 0.8 mL/min with a linear gradient of EtOH from 50 to 80% over 30 min, then 80% EtOH was kept for 10 min. The product (57.3 MBq, 89%) collected within 23.3-24.6 min after the injection was analyzed on HPLC: $t_R$=23.5 min, ≥97% radiochemical purity Bioscan NI(T)/UV 280 nm.

Stability Evaluation of 5-[$^{125}$I]-Iodo-5'-O-[cyclo-3,5-di(tert-butyl)-6-fluorosaligenyl]-3'-O-hexanoylguanidino]-2'-deoxyuridine Monophosphate (21)

Incubations: into a solution (1980 µL) of serum (mouse, human), buffer or cells media, a sample of (21), (296-370 kBq) in 15-20 µL of 25% EtOH/PB (100 mM, pH 6.1) was added; the resulting mixture was briefly vortexed and kept (up to 24 h) at ambient temperature or inside the incubator (37° C., ~5% $CO_2$). At each time point, a volume of 1 mL was withdrawn, the extract of sample prepared and analyzed by HPLC.

Preparation of extracts: a sample (1 mL) from each incubated mixture with compound (21) was treated with MeCN (1 mL), vortexed, and centrifuged (2,000 rpm, 15 min). The supernatant was removed and the radioactivity measured. Aliquots of supernatant (250-500 µL) were acidified to pH~6 with 0.05 N TFA (2-8 µL). The excess of MeCN was evaporated with a stream of nitrogen and water (100 µL) added. A mixture was passed through a 0.2µ filter and each sample (~100 µL, 148-222 kBq) analyzed on HPLC system.

HPLC analysis of extracts: proceeded on ACE-100, C18 100 Å (5 µm, 4.6×250 mm) column; eluted at 0.8 mL/min with a linear gradient of MeCN from 0 to 95% over 50 min and 95% MeCN was kept for a period of further 10 min, detecting the radioactivity (Bioscan NaI(T)). Both solvents contained 0.07% TFA (v/v).

The HPLC results are depicted in FIGS. 10A-10G.

5-Iodo-5'-O—[(N,N'-bis(tert-(butyloxycarbonyl)-N"-methyl-4-benzoyl)-guanidino]-2'-deoxyuridine (22)

In the preparation of (22), the required starting 5-iodo-5'-O-[4-(N-Boc-aminomethyl)-benzoyl]-3'-levulinyl-2'-deoxyuridine was obtained as follows: a solution of 5-iodo-3'-levulinyl]-2'-deoxyuridine (2.93 g, 6.48 mmol), 4-(Boc-aminomethyl)benzoic acid (1.71 g, 6.80 mmol), DCC (1.41 g, 6.83 mmol) and DMAP (0.20 g, 1.64 mmol) in DCM/DMF (20/4 mL) was stirred at room temperature for 4 h (TLC monitoring). The reaction mixture was filtered and the solvent evaporated under reduced pressure. To the remaining residue, EtOAc/n-hexane (80/20 mL) was added, and the stirred mixture was filtered again, then washed with the solution of citric acid, $NaHCO_3$, brine, dried over $MgSO_4$, and evaporated. A crude product was separated and purified twice by column chromatography on a silica gel (DCM/MeOH, 10/0.3-0.5) to yield 2.93 g (66%) of the product; $R_f$ value 0.62 in DCM/MeOH 10:0.5. HPLC analysis: $t_R$=31.4 (≥95% pure, UV at 280 nm) on ACE C18 column 100 Å (5 µm, 4.6×250 mm); eluted at the rate of 0.8 mL/min with a linear gradient of MeCN in water, from 10 to 95% MeCN over 45 min, then 95% B kept for 15 min. $^1$H NMR (DMSO-$d_6$, 500 MHz) δ: 11.14 (Is, H, HN-6 uridine), 8.17 (bs, 1H, NH), 8.05 (is, 1H, H6-uridine), 7.91-7.84 (m, 2H, aryl-H2, aryl-H6), 7.61-7.41 (m, 2H, aryl-H3, aryl-H5), 6.09-5.96 (m, 1H, H1'), 5.25-5.19 (m, 2H, benzyl), 4.68-4.46 (m, 2H, H3', H4'), 4.51-4.38 (m, 3H, H5', H3'), 3.05-2.87 (m, 2H, H3-Lev), 2.54-2.27 (m, 4H, H2', H2", H2-Lev), 2.11 (s, 1H, H5-Lev), 1.48 (s, 9H, H3-BocN) ppm.

The subsequent elimination of the N-Boc protecting group in ~15% TFA/MeCN and the following guanidinylation with N,N'-bis(tert-butyloxycarbonyl)-N'''-trifluoromethane-sulfonyl guanidine led to the target guanidinobenzoyll ester (22) in 67% yield, after the 3'-O-Lev group was removed (further details are below).

Starting with 5-iodo-5'-O-[4-(N-Boc-aminomethyl)-benzoyl]-3'-levulinyl-2'-deoxyuridine (2.76 g, 4.03 mmol), General Procedure A was carried out: the Boc protecting group was cleaved, and the separated crude TFA salt was reacted immediately with 1.23 g (4.89 mmol) of N,N'-bis(tert-butoxycarbonyl)-N'''-trifluoromethanesulfonyl guanidine in the presence of TEA added in two portions (2×685 µL, 9.75 mmol). The crude product dissolved in 60 mL of EtOAc was washed with solution of citric acid and brine, organic phase was dried over $MgSO_4$, evaporated, and the remaining residue purified on a silica gel column (EtOAc/n-hexane, 2:1) to give 2.57 g of white foam. This was treated with a mixture of $N_2H_4.H_2O$ (0.5 M, 0.26 mL) in pyridine/AcOH (4:1, 5 mL) to cleave the 3'-O-Lev group. A crude product purified on a silica gel column (DCM/MeOH, 10:0.4) was obtained as a white amorphous solid: 1.52 g, 67% yield, $R_f$ value 0.54 (DCM/MeOH, 10:0.5). HPLC analysis: $t_R$=41.39 (≥96% pure, UV at 280 nm) on ACE C18 column 100 Å (5 µm, 4.6×250 mm); eluted at the rate of 0.8 mL/min with a linear gradient of MeCN in water, from 10 to 95% MeCN over 45 min, then 95% B kept for 15 min. $^1$H NMR (DMSO-$d_6$, 500 MHz) δ: 11.46 (s, 1H, NH-uridine), 8.63 (bs, 1H, NH), 8.21 (t, 1H, NH, J=4.5 Hz), 7.97 (s, 1H, H6-uridine), 7.87-7.74 (m, 2H, aryl-H2, aryl-H6), 7.53-7.48 (m, 2H, aryl-H3, aryl-H5), 6.19-6.12 (m, 1H, H1'), 4.34-4.27 (m, 1H, H4'), 4.24-4.19 (m, 1H, H3', OH), 3.94-3.87 (m, 2H, benzyl), 3.76-3.68 (m, 2H, H5'), 2.34-2.26 (m, 1H, H2'), 2.20-2.15 (m, 1H, H2"), 1.50 (s, 9H, H3-BocN'), 1.46 (s, 9H, H3-BocN") ppm. $^{13}$C NMR (DMSO-$d_6$, 100 MHz) δ: 171.37 (C1-benzoyl), 163.42 (C4), 160.32 (C1-Boc-N'), 158.37 (C1-Boc-N"), 154.44 (C2), 149.68 (C-guanidine), 144.21 (C4-aryl), 139.26 (C2-aryl), 134.48 (C6), 127.32 (C3-aryl), 126.86 (C5-aryl), 111.62 (C1-aryl), 110.25 (C5), 89.85 (C1'), 86.46, (C4'), 82.26 (C2-Boc-N'), 81.32 (C2-Boc-N"), 71.72 (C3'), 69.34 (C-benzyl), 68.41 (C5'), 38.91 (C2'), 28.29 (C3-Boc-N'), 28.08 (C3-Boc-N") ppm.

5-Trimethylstannyl-5'-O—[(N,N'-bis(tert-(butyloxycarbonyl)-N"-methyl-4-benzoyl)-guanidino]-2'-deoxyuridine (23)

Stannylation of the iodide (22) (0.748 g, 1.025 mmol) was done with hexamethylditin 605 mg (1.846 mmol) in the presence of the palladium catalyst (72 mg, 0.01 mmol) and TEA (700 µL, 5.0 mmol) in EtOAc (20 mL). A crude product stannane (23) (286 mg, 36% yield) separated on a silica gel column using EtOAc/n-hexanes (2:0.5-1), $R_f$ value 0.62 (DCM/MeOH, 10:0.5) was ~92% pure by HPLC analysis (at 220/280 nm) and was further purified on a Columbus C18, 100 Å, (5 µm, 10×250 mm) semi preparative column (166 mg, ~7 mg per injection), eluted at the rate of 2.4 mL/min with a linear gradient of MeCN from 50 to 67% over 30 min, then from 67 to 95% over 10 min and 95% MeCN kept for 20 min. Following HPLC analysis confirmed high purity of the product: $t_R$=24.6 min (97.7% pure at 220/280 nm) on Columbus C18 100 Å, (5 µm, 4.6×250 mm) column, eluent: solvent A water, solvent B $CH_3CN$; eluted with a linear gradient of B from 50 to 95% over 30 min and then 95% B for 30 min and the elution rate 0.8 mL/min. $^1H$ NMR (DMSO-$d_6$, 500 MHz) δ: 11.14 (s, 1H, NH-uridine), 8.24 (bs, 1H, NH), 8.12 (t, 1H, NH, J=4.46 Hz), 7.94 (s, 1H, H6-uridine, $^3J_{Sn,H}$=19.42 Hz), 7.84-7.72 (m, 2H, aryl-H2, aryl-H6), 7.48-7.36 (m, 2H, aryl-H3, aryl-H5), 6.10-5.89 (m, 1H, H1'), 4.87-4.62 (m, 1H, H4'), 4.49-4.27 (m, 1H, H3', OH), 3.97-3.87 (m, 2H, benzyl), 3.68-3.53 (m, 2H, H5'), 2.38-2.29 (m, 1H, H2'), 2.16-2.08 (m, 1H, H2"), 1.47 (s, 9H, H3-BocN'), 1.44 (s, 9H, H3-BocN"), 0.29 (s, 9H, 3×$CH_3$—Sn, $^2J_{Sn,H}$=29.5 ppm. $^{13}C$ NMR (DMSO-$d_6$, 100 MHz) δ: 170.25 (C1-benzoyl), 163.39 (C4), 159.82 (C1-Boc-N'), 158.46 (C1-Boc-N"), 153.66 (C2), 149.56 (C-guanidine), 144.56 (C4-aryl), 143.78 (C6), 139.66 (C2-aryl), 127.51 (C5-aryl), 126.73 (C1-aryl), 111.91 (C3-aryl), 110.34 (C5), 90.37 (C1'), 86.22 (C4'), 84.17 (C2-Boc-N'), 81.85 (C2-Boc-N"), 70.65 (C3'), 69.12 (C-benzyl), 68.82 (C5'), 39.46 (C2'), 28.54 (C3-Boc-N'), 28.12 (C3-Boc-N"), -7.74 (3×$CH_3$—Sn) ppm. $^{119}Sn$ NMR (CDCl$_3$, 100 MHz) δ: -1.76 ppm.

Additional HPLC analysis confirmed high purity of the product: $t_R$=43.56 min (≥96% pure at 220 nm) on ACE C18 100 Å, (5 µm, 4.6×250 mm) column, eluted at the rate of 0.8 mL/min with a linear gradient of MeCN in water, from 10 to 95% MeCN over 45 min, then 95% MeCN kept for 15 min.

5-[$^{125}$I]-Iodo-5'-O—[(N,N'-bis(tert-(butyloxycarbonyl)-N"-methyl-4-benzoyl)-guanidino]-2'-deoxyuridine (24)

Stannane (23) (~100 µg) was radioiodinated twice (General Procedure C) with 20.3 and 37.6 MBq of Na$^{125}$I/NaOH and gave ~47 MBq of the product (24) with an average yield 81%. The reaction mixture was separated on HPLC using ACE-100 C18 100 Å (5 µm, 4.6×250 mm) column, eluted at the rate of 0.8 mL/min with a linear gradient of MeCN in water from 50 to 85% over 50 min, then from 85 to 95% in 10 min and 95% MeCN was held for further 10 min. The product was collected in three fractions within 19-21 min after the injection. An excess of unreacted stannane 23 was well separated, eluting ~10 min later. The HPLC analysis of the separated product ($t_R$=18.8 min) confirmed its high (≥98%) radiochemical purity, Bioscan NI(T)/UV 280 nm).

5-[$^{125}$I]-Iodo-5'-O-methyl-4-benzoylguanidino-2'-deoxyuridine (25)

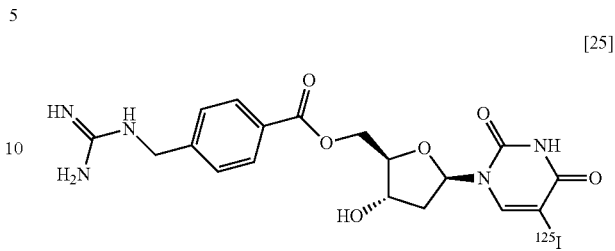

[25]

The cleavage of guanidine N-Boc protecting groups of compound (24) was carried out in a solution of 40% TFA in MeCN at room temperature and was completed after ~220 min. The reaction progress was monitored on HPLC (Bioscan NaI(T) detector), using ACE C18 100 Å (5 µm, 4.6×250 mm) column, eluted at 0.8 mL/min with a linear gradient of MeCN in water (5-95% over 45 min), with both solvents contained 0.07% TFA (v/v). See FIGS. 11A-11D, where A=5-[$^{125}$I]-Iodo-5'-O—[(N,N'-bis(tert-(butyloxycarbonyl)-N"-methyl-4-benzoyl)-guanidino]-2'-deoxyuridine (24), B=5-[$^{125}$I]-Iodo-5'-O—[(N-(tert-(butyloxycarbonyl)-N"-methyl-4-benzoyl)-guanidino]-2'-deoxyuridine, and C=5-[$^{125}$I]-Iodo-5'-O-methyl-4-benzoylguanidino-2'-deoxyuridine (25).

A faster cleavage rate (General Procedure C) was achieved when a dried residue of (24) (conducted twice with 13.2 and 30.7 MBq) was treated with neat TFA (40 µL) under nitrogen and kept in a tightly covered vial at 75° C. After 30 min the reaction was completed (checked by HPLC). An excess of TFA was evaporated with a stream of dry nitrogen and the product was separated on HPLC using ACE-100 C18 100 Å (5 µm, 4.6×250 mm) column, eluted at 0.8 mL/min with a linear gradient of MeCN in water from 0 to 95% over 45 min and with 95% MeCN was held for an additional 25 min; both solvents contained 0.07% TFA (v/v). The product eluted within 18-24 min after the injection and an average yield of separated 25 was 76%. The HPLC analysis: $t_R$=22.3 min, ≥98% radiochemical purity, Bioscan NI(T)/UV 280 nm). To finish, the purified (25) was evaporated again with a stream of nitrogen and to the dry residue (~33.0 MBq) ethanol (80 µL) was added, followed by potassium phosphate buffer (100 µL, 100 mM, pH 6.1). The resulted solution was injected on HPLC system equipped with Luna CN (5µ, 4.5×250 mm) column and was eluted at the rate of 0.8 mL/min with a linear gradient of EtOH in potassium phosphate buffer (100 mM PB, pH 6.1); from 10 to 15% over 10 min, next 15 to 60% over a period of 30 min and 60% EtOH for further 30 min. The product freed from an excess of TFA (28.4 MBq, 86% yield) was collected within 28.5-30.0 min after the injection and analyzed on HPLC: $t_R$=28.1 min, ≥98% radiochemical purity Bioscan NI(T)/UV 280 nm.

Stability Evaluation of 5-[$^{125}$I]-Iodo-5'-O-methyl-4-benzoylguanidino-2'-deoxyuridine (25)

Incubations: into a solution (1980 µL) of serum (mouse, human), buffer or cells media, a sample of (25), (296-370 kBq) in 15-20 µL of 25% EtOH/PB (100 mM, pH 6.1) was added; the resulting mixture was briefly vortexed and kept (up to 24 h) at ambient temperature or inside the incubator (37° C., ~5% $CO_2$). At each time point, a volume of 1 mL was withdrawn, the extract of sample prepared and analyzed by HPLC.

Preparation of extracts: a sample (1 mL) from each incubated mixture with compound (25) was treated with MeCN (1 mL), vortexed, and centrifuged (2,000 rpm, 15 min). The supernatant was removed and the radioactivity measured. Aliquots of supernatant (250-500 µL) were acidified to pH~6 with 0.05 N TFA (2-8 µL). The excess of MeCN was evaporated with a stream of nitrogen and water (100 µL) added. A mixture was passed through a 0.2µ filter and each sample (~100 µL, 148-222 kBq) analyzed on HPLC system.

HPLC analysis of extracts: proceeded on ACE-100, C18 100 Å (5 µm, 4.6×250 mm) column; eluted at 0.8 mL/min with a linear gradient of MeCN from 5 to 95% over 45 min and 95% MeCN was kept for a period of further 15 min, detecting the radioactivity (Bioscan NaI(T)). Both solvents contained 0.07% TFA (v/v). The HPLC results are depicted in FIGS. 12A-12G.

N,N'-bis(tert-butyloxycarbonyl)-3-iodobenzylguanidine (26)

This non-radioactive analog of radiolabelled bis-Boc-[$^{125}$I]mIBG (29), necessary in preparation of stannane 28 and [$^{125}$I]mIBG (30), was attained as follows: to a stirred solution of 3-iodobenzylamine (0.81 g, 3.47 mmol) in DCM (40 mL), placed in an ice bath, TEA (485 µL, 3.47 mmol) and N,N'-bis(tert-butoxycarbonyl)-N"-trifluoromethanesulfonyl guanidine (3.35 g, 3.32 mmol) were added, and the mixture was stirred at room temperature for ~4 h (TLC monitoring), at that time was filtered and the solvent evaporated under reduced pressure. To the remaining residue, 100 mL of EtOAc/n-hexane (4/1) was added and an excess of amines and triflic amide were removed by means of aqueous workup with 5% citric acid and saturated brine. The organic phase was dried over $MgSO_4$, filtered and evaporated. A crude product was separated and purified twice by column chromatography on a silica gel (DCM/hexanes, 2/0.5-1) to yield 1.26 g (76%) of the guanidine (26); $R_f$ value 0.62 in DCM/MeOH 10:0.5. HPLC analysis: $t_R$=23.39 (≥97% pure, UV at 280 nm) on ACE C18 column 100 Å (5 µm, 4.6×250 mm); eluted at the rate of 0.8 mL/min with a linear gradient of MeCN in water, from 70 to 95% MeCN over 45 min, then 95% MeCN was kept for 15 min. $^1$H NMR ($CDCl_3$, 500 MHz) δ: 11.47 (bs, 1H, NH-Boc), 8.58 (bs, 1H, NH-benzyl), 7.69-7.61 (m, 2H, aryl-H4, aryl-H2), 7.29-7.09 (m, aryl-H5, aryl-H6), 4.58 (s, 2H, benzyl), 1.53 (s, 9H, H3-BocN), 1.48 (s, 9H, H3-BocN') ppm. $^{13}$C NMR (DMSO-$d_6$, 100 MHz) δ: 163.5 (C1-BocN), 156.2 (C1-BocNH), 153.1 (C-guanidine), 140.4 (C1-aryl), 139.8 (C2-aryl), 136.9 (C4-aryl), 130.4 (C5-aryl), 127.1 (C6-aryl), 94.5 (C3-aryl), 83.4 (C2-BocNH), 79.5 (C2-BocN), 44.1 (C-benzyl), 28.3 (C3-BocNH), 28.1 (C3-BocN) ppm.

Additional HPLC analysis: $t_R$=46.81 (≥98% pure, UV at 254 nm) on Columbus C18 column 100 Å (5 µm, 4.6×250 mm); eluted at the rate of 0.8 mL/min with a linear gradient of MeCN in water, from 00 to 95% MeCN over 60 min.

3-iodobenzylguanidine (27)

The cleavage of guanidine N-Boc protecting groups of compound (26) carried out in a solution of 50% TFA in MeCN at room temperature was exceedingly slow and still not completed after 18 h. Deprotection performed in neat TFA (250 g of (26) in 100 µL of TFA) required ~120 min at room temperature and only 32 min when run at 60° C. The reaction progress was monitored on HPLC, using ACE C18 100 Å (5 µm, 4.6×250 mm) column, eluted at 0.8 mL/min with a 10% MeCN in water (isocratic) for 10 min, followed by a linear gradient of MeCN, from 10 to 95% over 40 min and 95% MeCN kept for next 20 min. Both solvents contained 0.07% TFA (v/v).

N,N'-bis(tert-butyloxycarbonyl)-3-trimethylstannyl-benzylguanidine (28)

A mixture of N,N'-bis(tert-butyloxycarbonyl)-3-iodobenzylguanidine (26) (0.206 g, 0.433 mmol), hexamethylditin 295 mg (0.90 mmol), palladium catalyst (30 mg, 0.043 mmol), and TEA (150 µL, 1.8 mmol) was refluxed in EtOAc (17 mL) under argon atmosphere, until the starting iodide was detectable (~3 h, checked often by TLC). After cooling to a room temperature and evaporation of the mixture, a crude product (28) was separated (98 mg, 44% yield) on a silica gel column using EtOAc/n-hexanes (0.5-1:4), $R_f$ value 0.65 (DCM/MeOH, 10:0.4), ~93% pure by HPLC analysis (at 220/280 nm) and was further purified on the Columbus C18, 100 Å, (5 µm, 10×250 mm) semi preparative column: (60 mg, ~5 mg per injection), eluted at the rate of 2.4 mL/min with a linear gradient of MeCN from 50 to 85% over 45 min, then from 85 to 95% over 15 min and 95% MeCN kept for another 10 min. Subsequent HPLC analysis confirmed higher purity of the stannylated product essential in radioiododestannylations: $t_R$=35.4 min (≥98.5% pure at 220/280 nm) on a Columbus C18 100 Å, (5 µm, 4.6×250 mm) column eluted at the rate of 0.8 mL/min with a linear gradient of MeCN in water from 70 to 95% over 45 min and then 95% MeCN kept for another 15 min. $^1$H NMR ($CDCl_3$, 500 MHz) δ: 11.53 (bs, 1H, NH-Boc), 8.62 (bs, 1H, NH-benzyl), 7.40-7.19 (m, 4H, aryl), 5.12 (s, 2H, benzyl), 1.52 (s, 9H, H3-BocN), 1.49 (s, 9H, H3-BocN'), 0.27 (s, 9H, 3×$CH_3$—Sn) ppm. $^{119}$Sn NMR ($CDCl_3$, 100 MHz) δ: −1.57 ppm.

N,N'-bis(tert-butyloxycarbonyl)-3-[$^{125}$I]-Iodobenzylguanidine (29)

Radioiodination (General Procedure C) of stannane (28) (~100 µg) was done twice with 59.2 and 58.1 MBq of Na$^{125}$I/NaOH, to give overall 104.4 MBq (89% average yield) of the isolated product. The reaction mixture was separated and purified by HPLC on Columbus C8 100 Å (5 µm, 4.6×250 mm) column, eluted at the rate of 0.8 mL/min with a linear gradient of MeCN in water from 50-95% over 45 min, then 95% MeCN was held for further 35 min. The product was collected in three fractions (within 40.5-42.5 min after the injection) and an excess of unreacted tin precursor was fully separated, eluting ~7.5 min later. HPLC analysis of the product confirmed its high purity: $t_R$=40.7 min, (≥98% radiochemical purity, Bioscan NI(T)/UV 280 nm).

3-[$^{125}$I]-Iodobenzylguanidine (30)

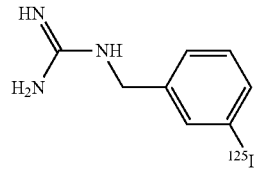

Method A:

A dried residue of (29), treated with neat TFA (60 μL) under nitrogen was kept in a tightly covered vial at ~65° C. After 30 min, the reaction (monitored by HPLC) was completed. An excess of TFA was evaporated with a stream of dry nitrogen and 100 μL of 50% MeCN in water added. The mixture was injected on HPLC fitted with ACE-100 C18 100 Å (5 μm, 4.6×250 mm) column and eluted at 0.8 mL/min with a 10% MeCN in water for 10 min, then by a linear gradient of MeCN in water from 10 to 95% over 40 min and 95% MeCN held for an additional 50 min; both solvents contained 0.07% TFA (v/v). The product was collected within 26-31 min after the injection. An average yield of (30) (from three preparations carried out with: 31.8, 44.4 and 50.3 MBq of (29)) was 86%. The subsequent HPLC analysis showed: $t_R$=28.7 min, ≥97% radiochemical purity, Bioscan NI(T)/UV 280 nm). To eliminate the presence of TFA, the solution of separated product (30) (~20.7 MBq) was evaporated and ethanol (80 μL) added, followed by potassium phosphate buffer (100 μL, 100 mM, pH 6.1). The resulting solution was again injected on HPLC system equipped with Luna CN (5μ, 4.5×250 mm) column and eluted at the rate of 0.8 mL/min with a linear gradient of EtOH in potassium phosphate buffer (100 mM PB, pH 6.1); from 30 to 70% over 60 min and 70% EtOH kept for further 10 min. The product freed from an excess of TFA (18.3 MBq, 88% yield) was collected within 24.0-33.0 min after the injection and was analyzed on HPLC: $t_R$=24.8 min, ≥98% radiochemical purity Bioscan NI(T)/UV 280 nm.

Method B:

Alternatively, the typical radioiodination (General Procedure C) of stannane (28) (~100 μg) was carried out, but the separation of Boc-protected guanidine (29) was omitted. A crude radioiodination mixture, quenched with a solution of $Na_2S_2O_3$, was evaporated with a stream of dried nitrogen and kept under a high vacuum. To the resulting dried residue, neat TFA (100 μL) was added, and the mixture remained in a sealed vial at 65° C. for ~35 min. After cooling, the mixture was diluted with $CH_3CN$ (200 μL) and evaporated with a stream of nitrogen, leaving ~20 μL of the liquid. This process was repeated twice. To the final residue, ethanol (80 μL) was added, followed by potassium phosphate buffer (100 μL, 100 mM PB, pH 6.1) and the solution injected on HPLC equipped with Luna CN 100 Å (5 μm, 4.6×250 mm) column eluted with a linear gradient of EtOH in potassium phosphate buffer as applied in Method A. Using this direct preparation three times; starting with 40.7, 38.9 and 24.1 MBq of $Na^{125}I$/NaOH, the guanidine 30 was attained with an average yield of 87%. HPLC analysis: $t_R$=24.7 min, ≥98% radiochemical purity Bioscan NI(T)/UV 280 nm.

Example 3

Figure 13:
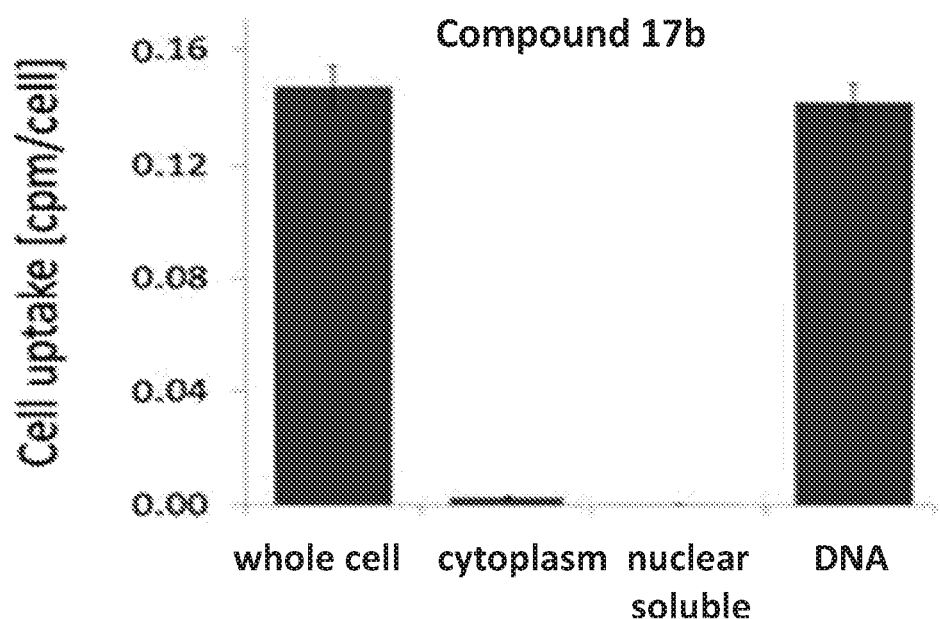
FIG. 13 is a graph showing the subcellular distribution of I in SK-N-SH NB cells exposed to conjugate 17b (radiolabeled with $^{125}$I) at 80 kBq/mL for 1 h, and harvested 24 h later.

Conjugate 17b was used for further testing. FIG. 13 shows the subcellular distribution of I in SK-N-SH NB cells exposed to conjugate 17b (radiolabeled with $^{125}$I) at 80 kBq/mL for 1 h, and harvested 24 h later. All $^{125}$I is associated with the DNA fraction indicating that after the initial localization of $^{125}$I-4 in the cytoplasm, the intracellular processing releases a metabolite that participates in the DNA synthesis. All drugs were designed so that they produce either 5-radioiodo-2'-deoxyuridine [RIUdR] or its 5'-monophosphate. Both metabolites can participate in the DNA synthesis allowing deposits of high LET radiation directly within the DNA structure. RIUdR, incorporated into the DNA of cancer cells in place of thymidine, is retained there for the life of the cell. It is extraordinarily lethal when labeled with Auger-electron-emitting radioiodines, which produce a cascade of monoenergetic electrons known as conversion and Auger electrons. These electrons deposit their energy within a tiny sphere around the decaying atom, i.e., the effective distance of Auger electrons is less than the diameter of the cancer cell nucleus. As a result, their cytotoxicity is dependent on the intranuclear localization, i.e., within the DNA or immediate vicinity of the DNA. Radiotoxicity of several reagents was tested in SK-N-SH cells. Tested drugs eradicate NB cells more efficiently than MIBG.

Figures 14A, 14B:
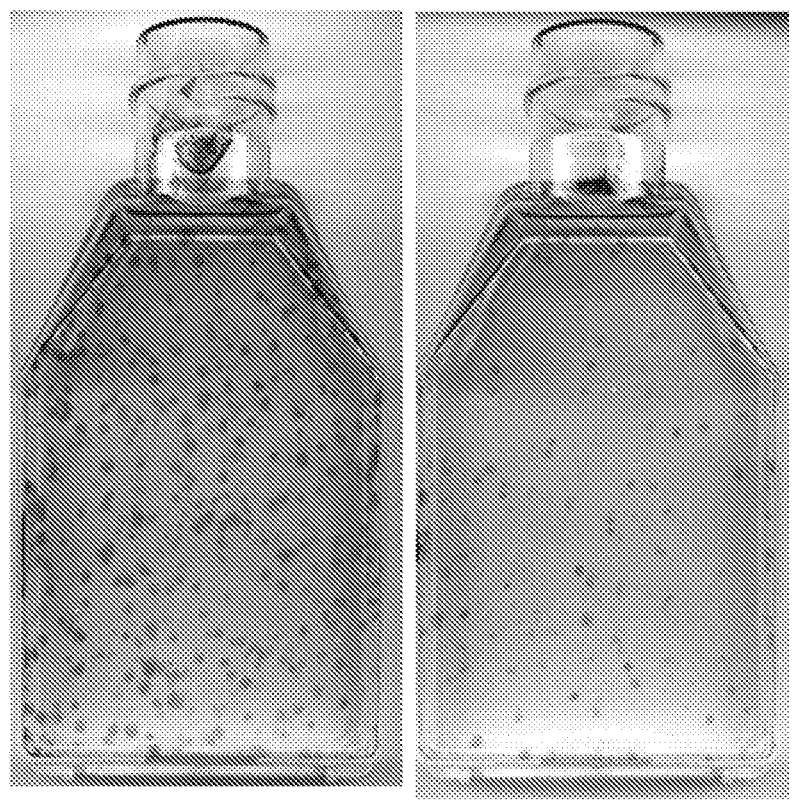
FIG. 14A is an image of colonies of SK-N-SH cells treated with 125IMIBG.
FIG. 14B is an image of colonies of SK-N-SH cells treated with compound 17b (radiolabeled with $^{125}$I)
Figure 14C:
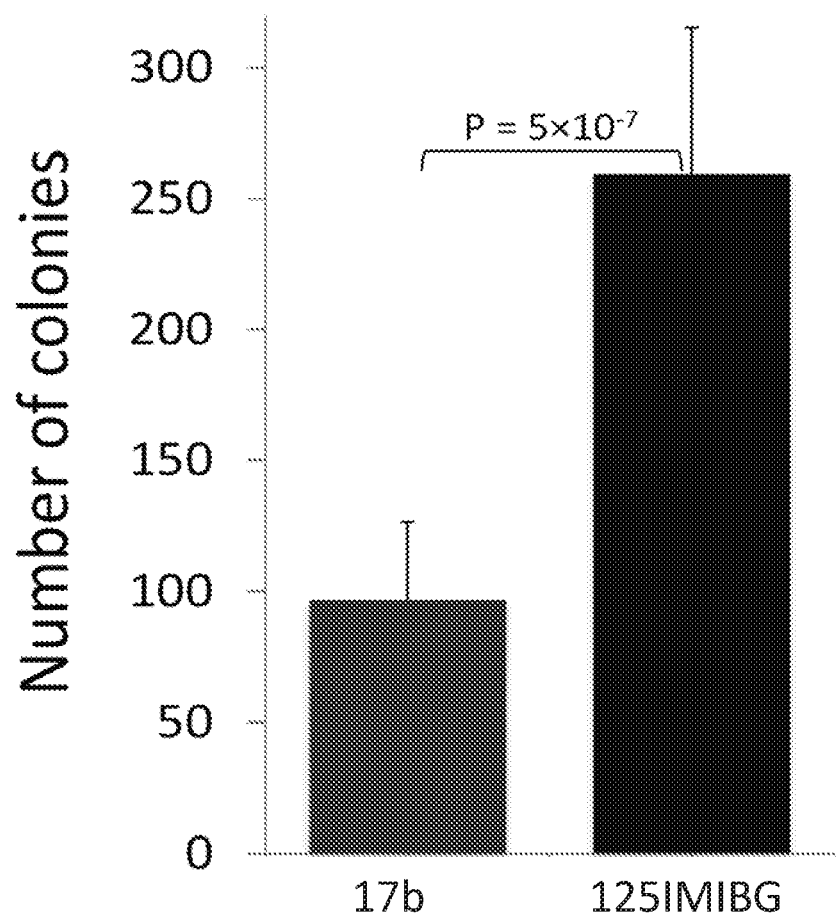
FIG. 14C is a graph of the colony count for each treatment for triplicate experiments.

FIG. 14A-C show results of a pilot radiotoxicity study comparing the reproductive integrity of colonies of human NB SK-N-SH cells treated with conjugate 17b (radiolabeled with $^{125}$I) and $^{125}$IMIBG at 37 kBq/mL, two weeks after treatment. FIG. 14A shows colonies of SK-N-SH cells treated with 125IMIBG, while FIG. 14B shows colonies of SK-N-SH cells treated with compound 17b. The DNA-incorporated conjugate 17b is far more radiotoxic. Even after just 1 h with the drug, more cells receive a lethal dose of radiation from conjugate 17b compared to $^{125}$IMIBG as measured in a clonogenic assay. Moreover, conjugate 17b (radiolabeled with $^{125}$I) is trapped within the cell assuring sustained availability throughout the cell cycle of the unsynchronized and heterogeneous cancer cell population.

Figure 15:
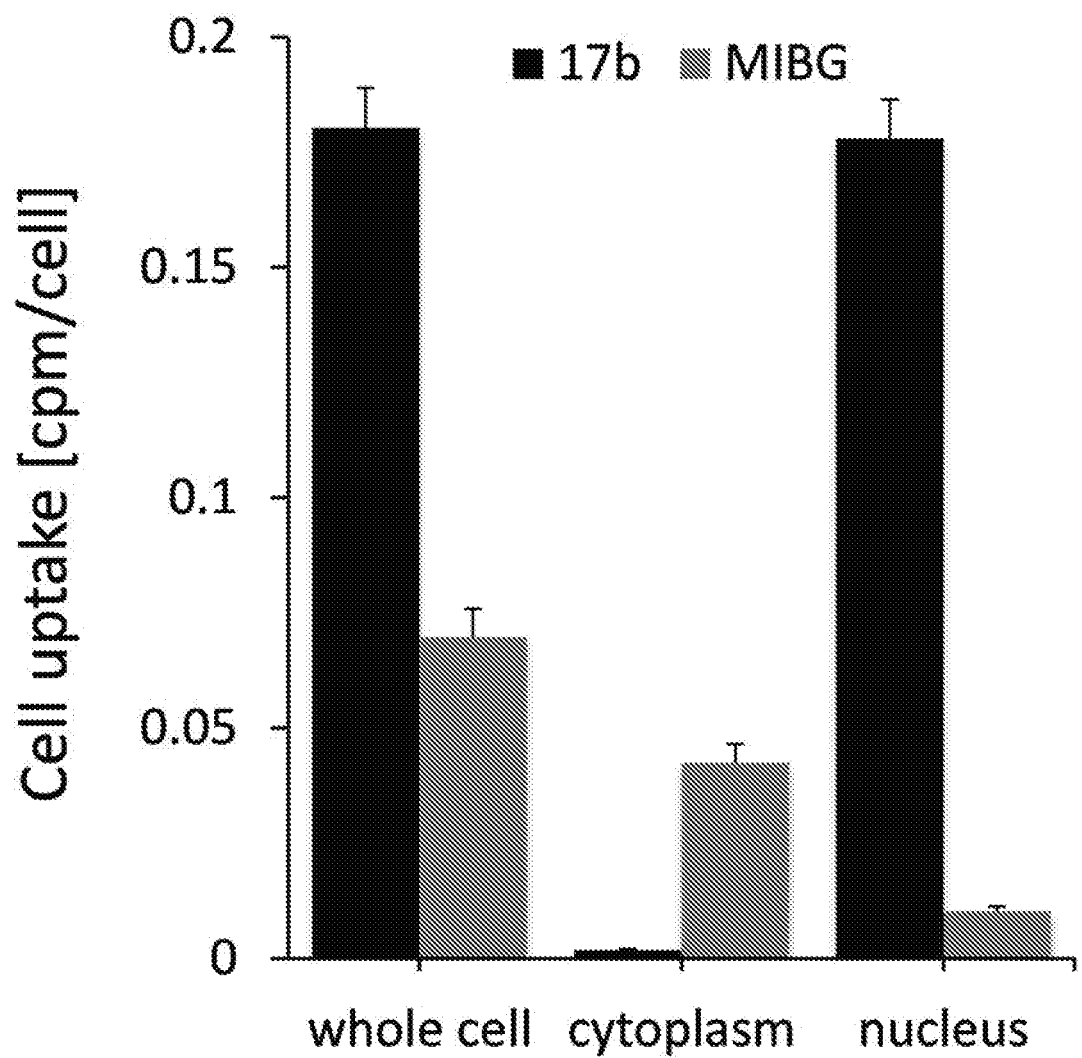
FIG. 15 is a graph showing cell uptake of conjugate 17b (radiolabeled with $^{125}$I) and subcellular distribution of 17b and MIBG in murine neuroblastoma cells N1E-115.
Figure 16:
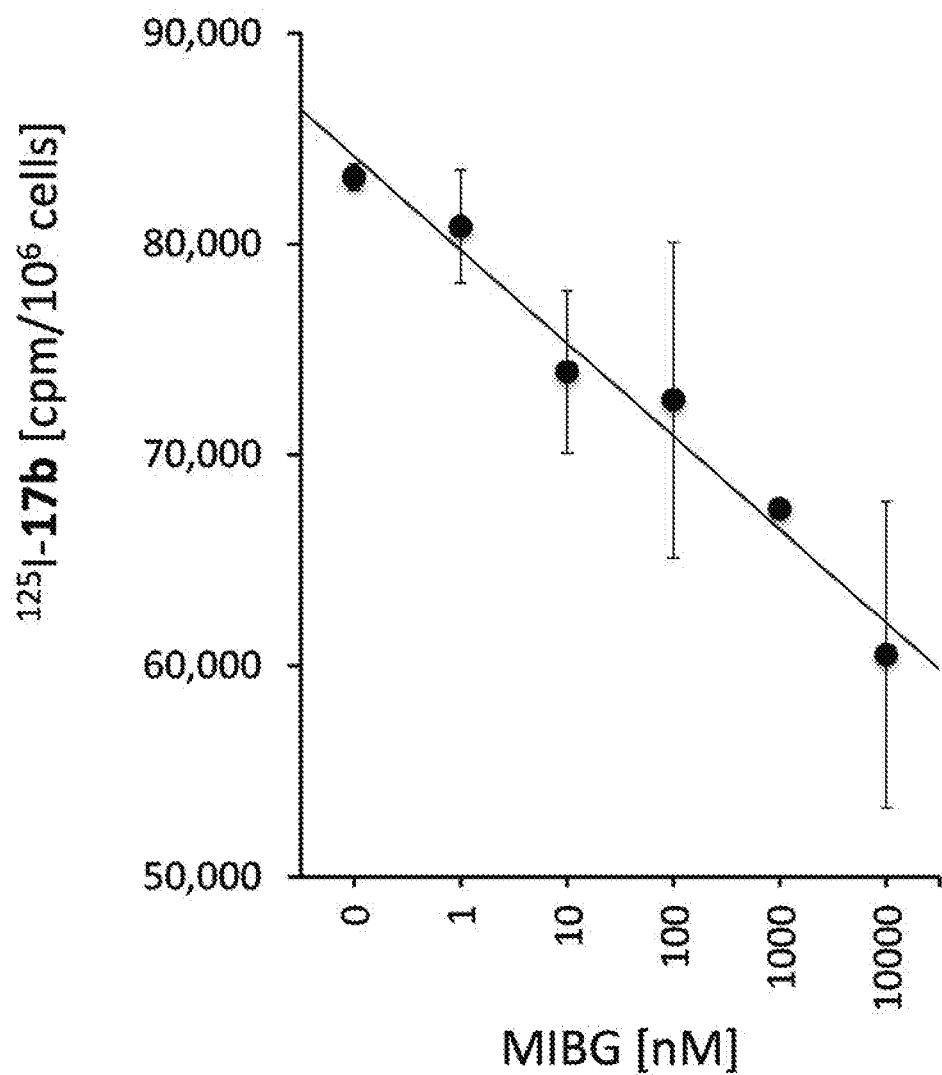
FIG. 16 shows uptake of 17b by SK-N-SH cells competed by MIBG.
Figure 17:
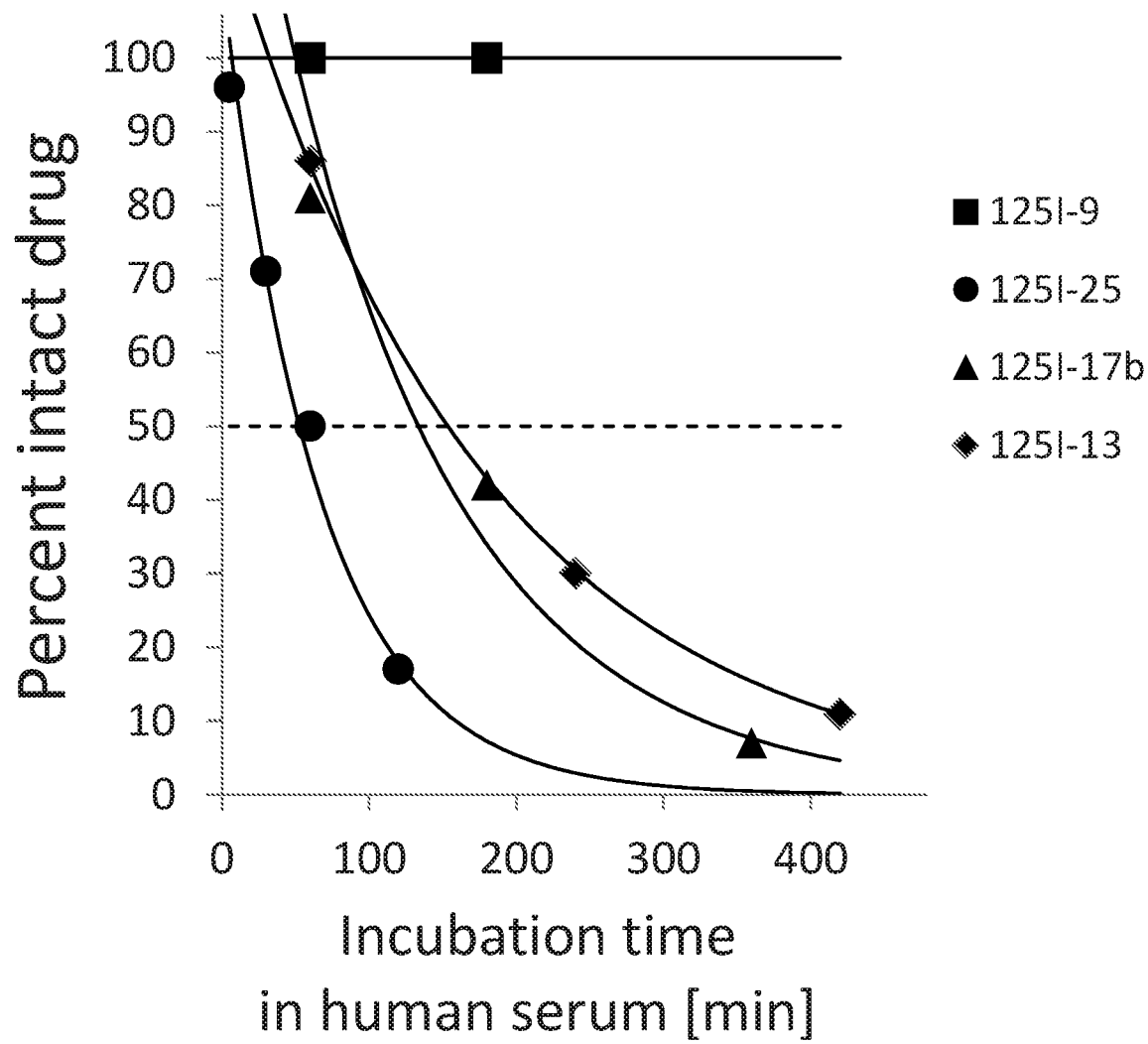
FIG. 17 is a graph of the stability of several of the guanidnine derivatives of 5-$^{125}$I-iodo-2'deoxyuridine in human serum.

FIG. 15 shows cell uptake of conjugate 17b (radiolabeled with $^{125}$I) and subcellular distribution of 17b and MIBG in murine neuroblastoma cells N1E-115. FIG. 16 shows uptake of 17b by SK-N-SH cells competed by MIBG. FIG. 17 provides an overview of stability of several of the guanidine derivatives of 5-$^{125}$I-iodo-2'deoxyuridine prepared herein in human serum.

The invention claimed is:

1. A therapeutic and/or diagnostic compound for selective targeting of norepinephrine transporter in a cell, comprising an MIBG analog conjugated to an active agent, said MIBG analog being selected from the group consisting of:

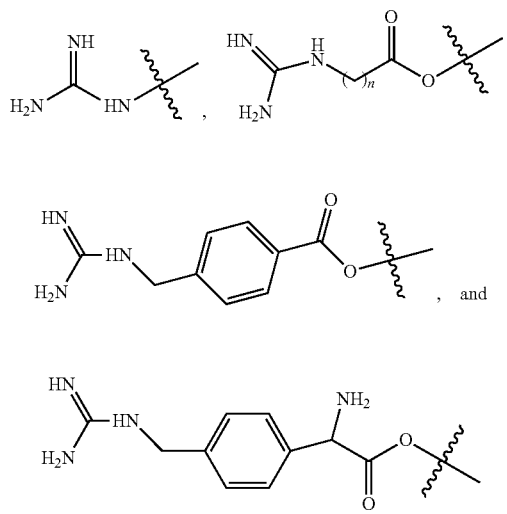

where n is 1-5, and the wavy line indicates the point of attachment to the active agent wherein said active agent is a radiolabeled thymidine analog of the formula:

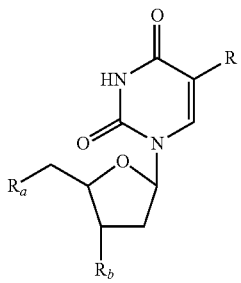

wherein:
R represents an Auger electron-emitting radionuclide;
$R_a$ represents —OH, a natural or unnatural L- or D-amino acid residue, a peptide comprising natural or unnatural L- or D-amino acid residues, cycloSaligenyl phosphotriester moiety, or said MIBG analog, and
$R_b$ represents a substituted or unsubstituted $C_1$-$C_6$ alkoxy, $C_1$-$C_8$ alkanoate group, —OH, a natural or unnatural L- or D-amino acid residue, a peptide comprising natural or unnatural L- or D-amino acid residues, cycloSaligenyl phosphotriester moiety, or said MIBG analog,
provided that at least one of the $R_a$ and $R_b$ substituents represents said MIBG analog.

2. The compound of claim 1, wherein said cycloSaligenyl phosphotriester moiety is a compound of the formula:

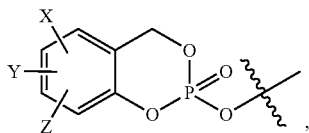

where:
X represents —H, —F, —Cl, or a substituted or unsubstituted $C_1$-$C_8$ alkyl, or $C_1$-$C_8$ alkoxy group;
Y represents —H, or a substituted or unsubstituted $C_1$-$C_8$ alkyl, $C_5$-$C_{14}$ aryl, or $C_5$-$C_{14}$ aryloxy group; and
Z represents —H, a substituted or unsubstituted $C_1$-$C_8$ alkyl, $C_5$-$C_{14}$ aryl, or $C_5$-$C_{14}$ aryloxy group.

3. The compound of claim 1, wherein said therapeutic and/or diagnostic compound is selected from the group consisting of:

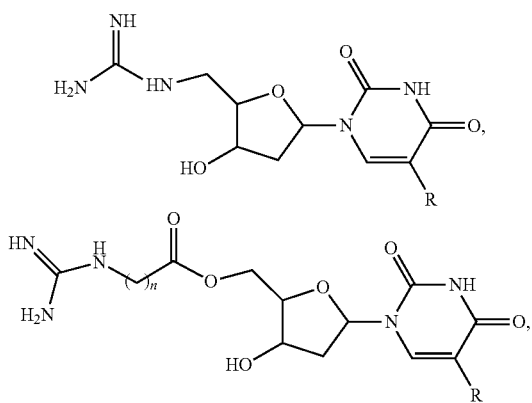

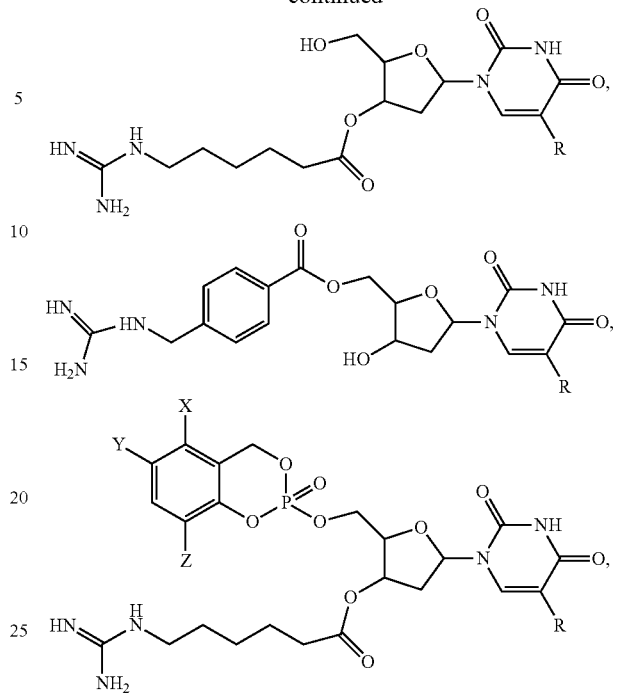

stereoisomeric forms thereof, and pharmaceutically acceptable salts thereof,
where: n is 1-5, R is an Auger electron-emitting radionuclide, X represents —H, —F, —Cl, or a substituted or unsubstituted $C_1$-$C_4$ alkyl, or $C_1$-$C_4$ alkoxy group, Y represents —H or a substituted or unsubstituted $C_1$-$C_4$ alkyl group, and Z represents —H or a substituted or unsubstituted $C_1$-$C_4$ alkyl group.

4. The compound of claim 3, wherein said Auger electron-emitting radionuclide is selected from the group consisting of $^{123}I$, $^{124}I$, $^{125}I$, $^{77}Br$, and $^{80m}Br$.

5. A therapeutic and/or diagnostic composition comprising at least one compound according to claim 1, said composition comprising a therapeutically- or diagnostically-effective amount of said compound, dispersed in a pharmaceutically-acceptable vehicle.

6. A method of treating neuroblastoma in a patient in need of such treatment, said neuroblastoma comprising cancer cells characterized by norepinephrine transporter expression, said method comprising administering to said patient a therapeutically effective amount of at least one therapeutic compound comprising an MIBG analog conjugated to an active agent according to claim 1.

7. The method of claim 6, wherein said at least one compound is administered by a method selected from the group consisting of intravenous, intraperitoneal, and intratumoral administration.

8. The method of claim 6, wherein said at least one compound is administered over a period of about 2 hours.

9. The method of claim 6, further comprising administering a sensitizing agent to said patient before administering said at least one therapeutic compound.

10. The method of claim 6, wherein said at least one therapeutic compound is administered so as to provide a dosage of from about 1 mCi/kg to about 100 mCi/kg to said patient.

11. A method of detecting cells expressing norepinephrine transporter in a subject, said method comprising:

administering to said patient an effective amount for imaging of at least one diagnostic compound comprising an MIBG analog conjugated to an active agent according to claim 1, wherein said active agent comprises a detectable label that generates a detectable signal; and detecting binding between said compound and said norepinephrine transporter expressed by said cells to thereby indicate a location of said cells in said subject.

12. The method of claim 11, wherein said cells are neuroblastoma cancer cells.

13. The method of claim 12, further comprising detecting the location of a primary neuroblastoma tumor in said patient.

14. The method of claim 12, further comprising detecting whether the cancer cells from said primary neuroblastoma have spread to other areas of the patient's body.

15. The method of claim 11, wherein said cells are cardiovascular cells.

16. The method of claim 11, wherein said detecting comprising detecting said detectable signal using scintigraphic imaging or magnetic resonance spectroscopy.

17. The method of claim 16, wherein said scinintigraphic imaging is selected from the group consisting of positron emission tomography and single photon emission computed tomography.

18. The method of claim 16, wherein said cells are neuroblastoma tumor cells, wherein said detecting yields a first image of said tumor to establish a baseline tumor size in said subject, said method further comprising re-administering said compound to said subject; and detecting binding between said compound and said norepinephrine transporter expressed by said cells to thereby yield a second image of said tumor, wherein differences between said second image and said first image are indicative of the tumor activity in said subject.

19. The method of claim 18, wherein said subject undergoes therapy for treatment of said tumor before said re-administering of said compound.

20. The method of claim 19, wherein said treatment is at least one of surgical excision, radiation therapy, and chemotherapy.

21. A kit for treating or detecting cells expressing norepinephrine transporter in a subject, said kit comprising a vessel containing a compound comprising an MIBG analog conjugated to an active agent according to claim 1; a pharmaceutically acceptable carrier medium; and instructions for use thereof.

* * * * *